United States Patent
Sinha et al.

(10) Patent No.: US 8,431,702 B2
(45) Date of Patent: Apr. 30, 2013

(54) THERAPEUTICALLY USEFUL SUBSTITUTED HYDROPYRIDO [3,2,1-IJ] QUINOLINE COMPOUNDS

(75) Inventors: Santosh C. Sinha, Ladera Ranch, CA (US); Smita S. Bhat, Irvine, CA (US); Ken Chow, Newport Coast, CA (US); Richard L. Beard, Newport Beach, CA (US); John E. Donello, Dana Point, CA (US); Michael E. Garst, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/569,418

(22) Filed: Aug. 8, 2012

(65) Prior Publication Data
US 2012/0309782 A1    Dec. 6, 2012

Related U.S. Application Data

(63) Continuation of application No. 13/461,398, filed on May 1, 2012, now Pat. No. 8,309,729, which is a continuation of application No. 13/150,751, filed on Jun. 1, 2011, now Pat. No. 8,188,279, which is a continuation of application No. 12/437,138, filed on May 7, 2009, now abandoned.

(60) Provisional application No. 61/051,533, filed on May 8, 2008.

(51) Int. Cl.
  *C07D 471/00* (2006.01)
  *C07D 451/00* (2006.01)
  *A61K 31/44* (2006.01)
(52) U.S. Cl.
  USPC .............. 546/81; 546/94; 514/292; 514/294
(58) Field of Classification Search .................. None
  See application file for complete search history.

(56) References Cited

U.S. PATENT DOCUMENTS

| 7,208,502 | B2 | 4/2007 | Solow-Cordero |
| 2007/0032459 | A1 | 2/2007 | Solow-Cordero |
| 2007/0232682 | A1 | 10/2007 | Beard et al. |

FOREIGN PATENT DOCUMENTS

| WO | WO03/062252 | 7/2003 |
| WO | WO 03/062392 | 7/2003 |
| WO | WO 2004/026864 | 4/2004 |
| WO | WO 2004/037213 | 5/2004 |
| WO | WO2004/096752 | 7/2004 |
| WO | WO2004/071442 | 8/2004 |
| WO | WO2004/096752 | 11/2004 |
| WO | WO2004/103279 | 12/2004 |
| WO | WO2004/103306 | 12/2004 |
| WO | WO 2007/056155 | 5/2007 |

OTHER PUBLICATIONS

"Prodrugs and Drug Delivery Systems," which is a chapter in Richard B. Silverman, Organic Chemistry of Drug Design Drug Action, 2d Ed., Elsevier Academic Press: Amsterdam, 2004, pp. 496-557.
John M. Mellor; et al; Tetrahedron, 1995, 6115.
Clemens, J.J. et al., Bioorg. Med. Chem. Lett, 2003, 13, 3401.
Hale, J.J. et al., Boorg. Med. Chem. Lett. 2004, 14, 3351.
Hale, J.J. et al., Boorg. Med. Chem. Lett. 2004, 14, 3495.
Yan, L. et al., Boorg. Med. Chem. Lett. 2004, 14, 4861.
Clemens, J.J. et al., Bioorg. Med. Chem. Lett, 2004, 14, 4903.
Hale, J.J. et al., Boorg. Med. Chem. Lett. 2004, 14, 3501.
Hale, J.J. et al., Boorg. Med. Chem. Lett. 2004, 47, 6662.
Tavora de Albuquerque Silva, Mini-Reviews in Med. Chem., 2005, vol. 5, pp. 893-914.
Brinkman, V. Phamacol. and Thera. 115 (2007) pp. 84-105.
Patani, G. et al., Chem. Rev. 1996, vol. 96, pp. 3147-3176.
Lewis, R., ed., Hawley's Condensed Chemical Dictionary, 15th ed.,2007, John Wiley & Sons excerpt pp. 1-3.
Vippagunta, S., et al., "Crystalline solids," in Adv. Drug Deliv. Rev. 48 (2001) pp. 3-26.
West, Anthony R., Solid State Chemistry and its Applications, Wiley, New York, 1988, pp. 358 & 365.
Database Chemcats [Online] Chemical Abstracts Service, Columbus, US; RN 773135-85-6 Jan. 1, 2009.XP002538092.
Database Chemcats [Online] Chemical Abstract Service, Columbus, US; RN 773874-23-0 Jan. 1, 2009.XP002538090.
Database Chemcats [Online] Chemical Abstracts Service, Columbus, US; RN 311324-17-1 Mar. 24, 2009.XP002538091.
Database Chemcats [Online] Chemical Abstracts Service, Columbus, US; RN 773129-68-31 Jan. 2009.XP002538093.

(Continued)

*Primary Examiner* — D M Seaman
*Assistant Examiner* — Heidi Reese
(74) *Attorney, Agent, or Firm* — John E. Wurst; Doina G. Ene; Allergan, Inc.

(57) ABSTRACT

Disclosed herein are compounds represented by the structural formula:

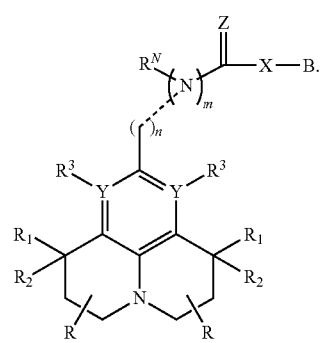

therapeutic methods, compositions, and medicaments related thereto are also disclosed.

8 Claims, No Drawings

OTHER PUBLICATIONS

Database Chemcats [Online] Chemical Abstracts Service, Columbus, US; RN 773869-60-6 Jan. 1, 2009.XP002538094.

Holt, Jason J.; et al.: A Microwave-Assisted Synthesis of Julolidine-9-carboxamide Derivatives and Their Conversion to Chalcogenoxanthones via Directed Metalation. J. Org. Chem. 2007, 72, 2690-2693.

Lee, Seokjoon; et al.: Synthesis and Anti-Angiogenesis Activity of Coumarin Derivatives. Bioorganic & Medicinal Chemist~Letters 16 (2006) 4596-4599.

THERAPEUTICALLY USEFUL SUBSTITUTED HYDROPYRIDO [3,2,1-IJ] QUINOLINE COMPOUNDS

RELATED APPLICATION

This application is a Continuation of U.S. patent application Ser. No. 13/461,398, filed May 1, 2012, is a Continuation of U.S. patent application Ser. No. 13/150,751, filed Jun. 1, 2011, which is a Continuation of U.S. patent application Ser. No. 12/437,138, filed May 7, 2009, to which claims priority to U.S. Provisional Application 61/051,533, filed May 8, 2008, the disclosure of which are incorporated by reference herein in their entirety

FIELD OF THE INVENTION

The present invention provides novel substituted hydropyrido[3,2,1-ij]quinoline compounds, and their uses in medicaments for the treatment of mammals with diseases and conditions that are alleviated by sphingosine-1-phosphate (S1P) receptors modulation.

BACKGROUND OF THE INVENTION

Sphingosine is a compound having the chemical structure shown in the general formula described below, in which $Y^1$ is hydrogen. It is known that various sphingolipids, having sphingosine as a constituent, are widely distributed in the living body including on the surface of cell membranes of cells in the nervous system.

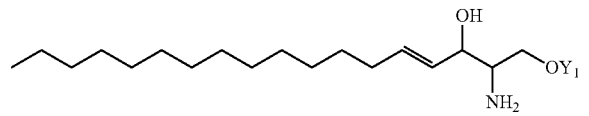

A sphingolipid is one of the lipids having important roles in the living body. A disease called lipidosis is caused by accumulation of a specified sphingolipid in the body. Sphingolipids present on cell membranes function to regulate cell growth; participate in the development and differentiation of cells; function in nerves; are involved in the infection and malignancy of cells; etc. Many of the physiological roles of sphingolipids remain to be solved. Recently the possibility that ceramide, a derivative of sphingosine, has an important role in the mechanism of cell signal transduction has been indicated, and studies about its effect on apoptosis and cell cycle have been reported.

Sphingosine-1-phosphate is an important cellular metabolite, derived from ceramide that is synthesized de novo or as part of the sphingomeyeline cycle (in animals cells). It has also been found in insects, yeasts and plants.

The enzyme, ceramidase, acts upon ceramides to release sphingosine, which is phosphorylated by sphingosine kinase, a ubiquitous enzyme in the cytosol and endoplasmic reticulum, to form sphingosine-1-phosphate. The reverse reaction can occur also by the action of sphingosine phosphatases, and the enzymes act in concert to control the cellular concentrations of the metabolite, which concentrations are always low. In plasma, such concentration can reach 0.2 to 0.9 µM, and the metabolite is found in association with the lipoproteins, especially the HDL. It should also be noted that sphingosine-1-phosphate formation is an essential step in the catabolism of sphingoid bases.

Like its precursors, sphingosine-1-phosphate is a potent messenger molecule that perhaps uniquely operates both intra- and inter-cellularly, but with very different functions from ceramides and sphingosine. The balance between these various sphingolipid metabolites may be important for health. For example, within the cell, sphingosine-1-phosphate promotes cellular division (mitosis) as opposed to cell death (apoptosis), which it inhibits. Intracellularly, it also functions to regulate calcium mobilization and cell growth in response to a variety of extracellular stimuli. Current opinion appears to suggest that the balance between sphingosine-1-phosphate and ceramide and/or sphingosine levels in cells is critical for their viability.

In common with the lysophospholipids, especially lyso-phosphatidic acid, with which it has some structural similarities, sphingosine-1-phosphate exerts many of its extra-cellular effects through interaction with five specific G protein-coupled receptors on cell surfaces, known as endothelium differentiation gene receptors ("Edg" or "S1P" receptors).

S1P3 receptor is one of the receptors interacting with sphingosine-1-phosphate. S1P3 receptor, alone or together with other S1P receptors, involves in many critical biological processes, such as the growth of new blood vessels, vascular maturation, cardiac development and immunity, as well as for directed cell movement. S1P3 receptor modulators are needed for therapeutic uses.

SUMMARY OF THE INVENTION

The compounds of the present invention can be represented by the structural formula:

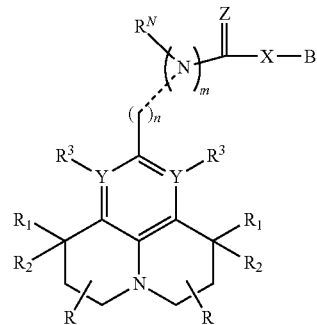

wherein m is an integer of 0, or 1; n is an integer of 0, 1, 2, or 3; each Y is independently carbon (C) or nitrogen (N); Z and X are each independently selected from the group of oxygen (O), sulfur (S), and amine moiety $NR^N$; B is selected from the group consisting of hydrogen, hydrocarbyl, heterohydrocarbyl, substituted or unsubstituted aryl, halohydrocarbyl, hydroxyl, alkoxyl, hydroxyalkyl, alkylcarbonyl, carbonylalkyl, formyl, oxycarbonyl, aminocarbonyl, alkyl carboxyl, alkyl amide, amino, alkylamino, cyano and X—B together being a heterocyclic ring or ring system; R and $R^3$ are each independently selected from the group consisting of hydrogen, hydrocarbyl, heterohydrocarbyl, substituted or unsubstituted aryl, halo, halohydrocarbyl, hydroxyl, alkoxyl, hydroxyalkyl, alkylcarbonyl, carbonylalkyl, formyl, oxycarbonyl, aminocarbonyl, alkyl carboxyl, alkyl amide, amino, alkylamino, and cyano; each $R^1$ is independently selected from the group consisting of hydrogen, hydrocarbyl, heterohydrocarbyl, substituted or unsubstituted aryl, halo, halohydrocarbyl, hydroxyl, alkoxyl, hydroxyalkyl, alkylcarbonyl, formyl, oxycarbonyl, aminocarbonyl, aminocarbonxyl, alkylcarboxyl, alkyl amide, amino, alkylamino, and cyano; each $R^2$ is independently selected from the group consisting of hydrocarbyl, heterohydrocarbyl, substituted or unsubstituted aryl, halo, halohydrocarbyl, hydroxyl, alkoxyl, hydroxyalkyl, alkylcarbonyl, formyl, oxo, oxycarbonyl, carboxyl, alkyl carboxylate, alkyl amide, aminocarbonyl, amino, alkylamino, and cyano; each $R^N$ is independently selected from the group consisting of hydrogen, hydrocarbyl, heterohydrocarbyl, substituted or unsubstituted aryl, halohydrocarbyl, hydroxyl, alkoxyl, hydroxyalkyl, alkylcarbonyl, carbonylalkyl, formyl, oxycarbonyl, aminocarbonyl, alkyl carboxyl, alkyl amide, amino, alkylamino, and cyano; including their alternate solid forms, tautomers, stereoisomers, enantiomers, diastereomers, prodrugs, and pharmaceutically acceptable salts, hydrates and solvates; and provided that when Y is carbon, and Z and X are both oxygen, $R^2$ is not oxo, or $R^1$ and $R^2$ are not both phenyl or both methyl at the same time.

Applicants have discovered that these compounds modulate sphingosine-1-phosphate (S1P) receptor activity, in particularly inhibit S1P3 receptor. These compounds are useful for the treatment of mammals, including human beings, with a range of conditions and diseases that are alleviated by S1P modulation, such as ocular diseases and conditions (glaucoma, elevated intraocular pressure, dry eye, and optical neurodegenerative diseases), cardiovascular diseases and conditions, pulmonary diseases and conditions, skin conditions, angiogenesis, inflammation, sepsis and pain.

DETAILED DESCRIPTION OF THE INVENTION

Disclosed herein are compounds represented by the structural formula:

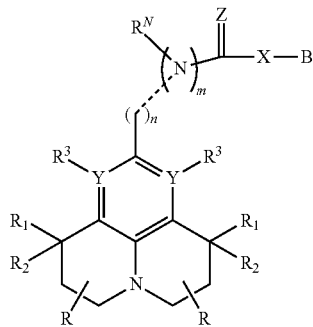

wherein m is an integer of 0 or 1; n is an integer of 0, 1, 2, or 3; each Y is independently carbon (C) or nitrogen (N); Z and X are each independently selected from the group of oxygen (O), sulfur (S), and amine moiety $NR^N$; B is selected from the group consisting of hydrogen, hydrocarbyl, heterohydrocarbyl, substituted or unsubstituted aryl, halohydrocarbyl, hydroxyl, alkoxyl, hydroxyalkyl, alkylcarbonyl, carbonylalkyl, formyl, oxycarbonyl, aminocarbonyl, alkyl carboxyl, alkyl amide, amino, alkylamino, cyano and X—B together being a heterocyclic ring/ring system.

R and $R^3$ are each independently selected from the group consisting of hydrogen, hydrocarbyl, heterohydrocarbyl, substituted or unsubstituted aryl, halo, halohydrocarbyl, hydroxyl, alkoxyl, hydroxyalkyl, alkylcarbonyl, carbonylalkyl, formyl, oxycarbonyl, aminocarbonyl, alkyl carboxyl, alkyl amide, amino, alkylamino, and cyano; each $R^1$ is independently selected from the group consisting of hydrogen, hydrocarbyl, heterohydrocarbyl, substituted or unsubstituted aryl, halo, halohydrocarbyl, hydroxyl, alkoxyl, hydroxyalkyl, alkylcarbonyl, formyl, oxycarbonyl, aminocarbonyl, aminocarbonxyl, alkylcarboxyl, alkyl amide, amino, alkylamino, and cyano; each $R^2$ is independently selected from the group consisting of hydrocarbyl, heterohydrocarbyl, substituted or unsubstituted aryl, halo, halohydrocarbyl, hydroxyl, alkoxyl, hydroxyalkyl, alkylcarbonyl, formyl, oxo, oxycarbonyl, carboxyl, alkyl carboxylate, alkyl amide, aminocarbonyl, amino, alkylamino, and cyano; each $R^N$ is independently selected from the group consisting of hydrogen, hydrocarbyl, heterohydrocarbyl, substituted or unsubstituted aryl, halohydrocarbyl, hydroxyl, alkoxyl, hydroxyalkyl, alkylcarbonyl, carbonylalkyl, formyl, oxycarbonyl, aminocarbonyl, alkyl carboxyl, alkyl amide, amino, alkylamino, and cyano; including their alternate solid forms, tautomers, stereoisomers, enantiomers, diastereomers, prodrugs, and pharmaceutically acceptable salts, hydrates and solvates; and optionally, provided that when Y is carbon, and Z and X are both oxygen, $R^2$ is not oxo, or $R^1$ and $R^2$ are not both phenyl or both methyl at the same time.

It has been discovered that the compounds of the present invention listed in this patent application modulate sphingosine-1-phosphate (S1P) receptor activity and in particular the S1P3 receptor. These compounds are useful for the treatment of mammals, including humans, with a range of conditions and diseases that are alleviated by S1P modulation: not limited to treating glaucoma, elevated intraocular pressure, ischemic neuropathies, optic neuropathy, pain, visceral pain, corneal pain, headache pain, migraine, cancer pain, back pain, irritable bowel syndrome pain, muscle pain and pain associated with diabetic neuropathy, the treatment of diabetic retinopathy, other retinal degenerative conditions, dry eye, angiogenesis and wounds. Other uses include:

Ocular Applications:
Retinopathy of prematurity, diabetic retinopathy, optic neuropathy, glaucomatous retinopathy, macular degeneration, choroidal neovascularization, ocular wound healing, and retinal edema;

Cardiovascular Applications:
Congestive heart failure, cardiac arrhythmia, atherosclerosis, and bradycardia;

Pulmonary Applications:
Asthma, chronic obstructive pulmonary disease, acute lung injury, acute respiratory distress syndrome, idiopathic pulmonary fibrosis, and ventilation-induced lung injury; and, Skin Applications:
Scar-less wound healing, scar-less skin-wound and cosmetic healing.

For the purposes of this disclosure, "treat," "treating," or "treatment" refer to the diagnosis, cure, mitigation, treatment, or prevention of disease or other undesirable condition.

The compounds of present invention may be identified either by their chemical structures and/or chemical names. If the chemical structure and the chemical name conflict, the chemical structure is determinative of the identity of the compound.

The compounds of the invention may contain one or more chiral centers and/or double bonds and therefore, may exist as stereoisomers, such as double-bond isomers, enantiomers or diastereomers. Accordingly, the chemical structures depicted herein encompass all possible enantiomers and stereoisomers, including the stereoisomerically pure form and enantiomeric and stereoisomeric mixtures. The compounds of the invention may also exist in several tautomeric forms, including but not limiting to, the enol form, the keto form and mixtures thereof. Accordingly, the chemical structures depicted herein encompass all possible tautomeric forms. The compounds of the invention also include isotopically labeled compounds where one or more atoms have an atomic mass different from the atomic mass conventionally found in nature.

Further, the compounds of the invention should be construed broadly to include their pharmaceutically acceptable salts, prodrugs, alternate solid forms, non-covalent complexes, and combinations thereof, unless otherwise indicated.

A pharmaceutically acceptable salt is any salt of the parent compound that is suitable for administration to a mammal, including human. A pharmaceutically acceptable salt also refers to any salt which may form in vivo as a result of administration of an acid, another salt, or a prodrug which is converted into an acid or salt. A salt comprises one or more ionic forms of the compound, such as a conjugate acid or base, associated with one or more corresponding counterions. Salts can form from or incorporate one or more deprotonated acidic groups (e.g. carboxylic acids), one or more protonated basic groups (e.g. amines), or both (e.g. zwitterions).

A prodrug is a compound which is converted to a therapeutically active compound after administration. For example, conversion may occur by hydrolysis of an ester group or some other biologically labile groups. Prodrug preparation is well known in the art. For example, "Prodrugs and Drug Delivery Systems," which is a chapter in Richard B. Silverman, *Organic Chemistry of Drug Design and Drug Action*, 2d Ed., Elsevier Academic Press: Amsterdam, 2004, pp. 496-557, provides further detail on this subject.

Alternate solid forms are different solid forms than those that may result from practicing the procedures described herein. For example, alternate solid forms may be polymorphs, different kinds of amorphous solid forms, glasses, and the like.

Non-covalent complexes are complexes that may form between the compound and one or more additional chemical species that do not involve a covalent bonding interaction between the compound and the additional chemical species. They may or may not have a specific ratio between the compound and the additional chemical species. Examples include solvates, hydrates, charge transfer complexes, and the like.

Hydrocarbyl consists of carbon and hydrogen, wherein each carbon has 4 covalent bonds and each hydrogen has a single bond to a carbon atom. "Hydrocarbyl fragments" has the same meaning as "hydrocarbyl," but is merely used for convenience for counting purposes. For example, one or more hydrocarbyl fragments means, 1, 2, or more distinct parts that each consists of hydrocarbyl, which may be interrupted by another moiety. For example, a functional group may be attached to 2 distinct hydrocarbyl fragments.

Hydrocarbyl includes alkyl, alkenyl, alkynyl, aryl containing only hydrogen and carbon, and combinations thereof. Hydrocarbyl may be linear, branched, cyclic (aromatic or non-aromatic), or combinations thereof, which can be further substituted.

Alkyl is a hydrocarbyl having no double bonds. Examples include methyl, ethyl, propyl isomers, butyl isomers, pentyl isomers, hexyl isomers, cyclopropyl, cyclobutyl, cyclopentyl, cyclohexyl, etc.

Alkenyl is a hydrocarbyl having one or more double bonds. Examples include ethenyl, propenyl, butenyl isomers, pentenyl isomers, hexenyl isomers, cyclopentenyl, cyclohexenyl, etc.

Alkynyl is a hydrocarbyl having one or more triple bonds. Examples include ethynyl, propynyl, butynyl isomers, pentynyl isomers, hexynyl isomers, cyclopentynyl, cyclohexynyl, etc.

Aryl is a substituted or unsubstituted aromatic ring or ring system. It can be hydrocarbon-aryl or heteroaryl. Examples of hydrocarbon-aryl include substituted and unsubstituted phenyl, naphthyl, and biphenyl. Such aryl group can be bonded to other moieties within the molecule at any position.

Each hydrogen atom has one covalent bond to carbon (C), nitrogen (N), oxygen (O), or sulfur (S).

Halo or halo atoms are fluorine (F), chlorine (Cl), bromine (Br), and iodine (I). Each halo atom forms a single bond to a carbon atom. Halohydrocarbyl is a hydrocarbyl having one or more F, Cl, Br, or I as substituents.

Heterohydrocarbyl refers to a hydrocarbyl as defined above with at least one non-carbon atom(s) presented at the backbone, including but not limiting to, oxygen (O), sulfur (S), nitrogen (N), phosphor (P), and halo atoms. Heterohydrocarbyl may be linear, branched, cyclic (aromatic or non-aromatic), or combinations thereof, which can be further substituted.

Examples of heterohydrocarbyl include: —$R^{10}$-$G^1$-$R^{11}$, $R^{10}$-HI, -$G^1$-$R^{10}$, -$G^1$-$R^{10}$-HI, $G^1$-$R^{10}$-$G^2$, and $G^1$-$R^{10}$-$G^2$-$R^{11}$, wherein $R^{10}$ and $R^{11}$ are independently hydrocarbyl or hydrogen (provided that hydrogen is attached to only one C, N, O, or S atom), $G^1$ and $G^2$ are independently functional groups, and HI is halo.

Additional examples of heterohydrocarbyl are depicted below, wherein $R^{10}$, $R^{11}$, $R^{12}$, and $R^{13}$ are independently hydrocarbyl or hydrogen. Other possibilities exist, but are not depicted here.

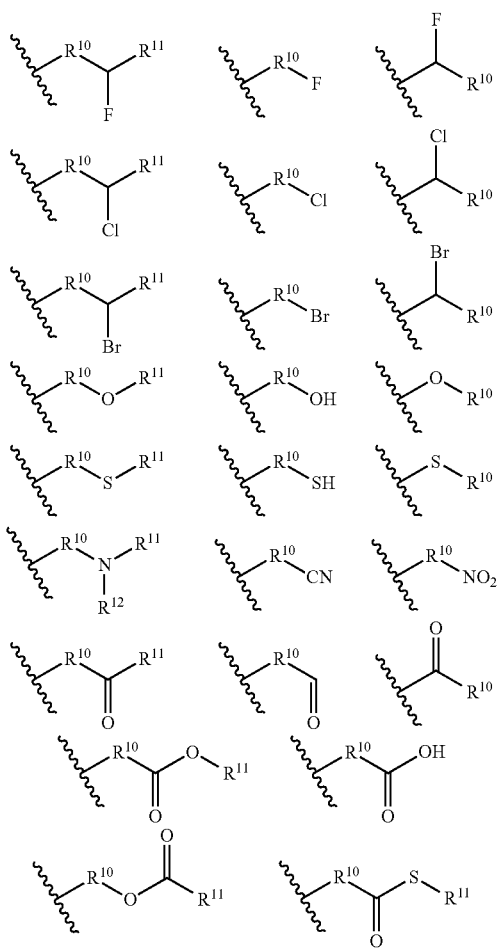

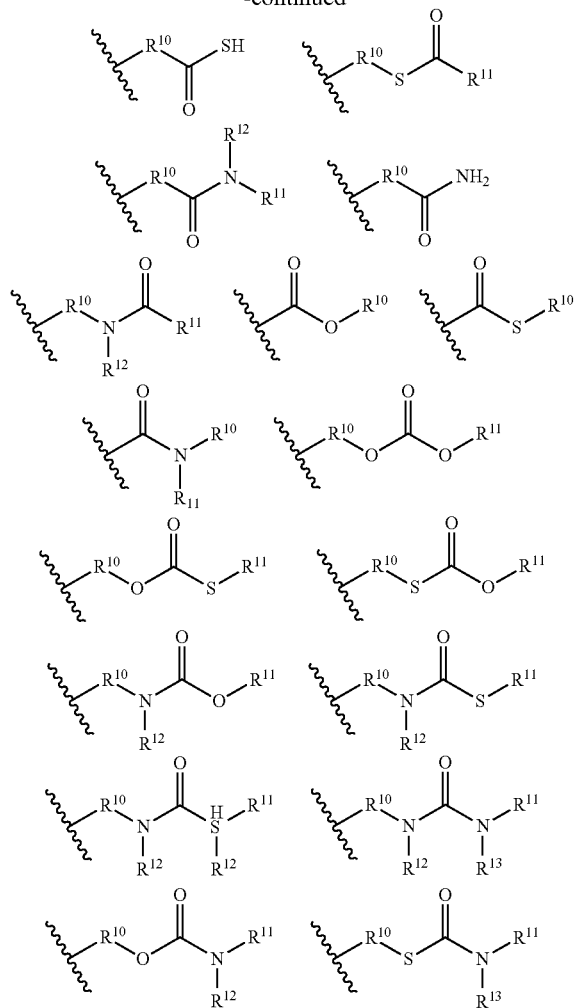

Heteroaryl is one type of heterohydrocarbyl, referring to an aromatic ring or ring system containing at least one hetero atom selected from N, O, S, P, and combinations thereof. Examples of heteroaryl include, but not limit to, pyridine, pyrazine, pyrimidine, pyridazine, triazine, furan, pyrrole, thiophene, imidazole, pyrazole, oxazole, isoxazole, thiazole, isothiazole, oxadiazole, thiadiazole, naphthalene, quinoline, quinoxaline, quinazoline, cinnoline, isoquinoline, benzofuran, indole, benzothiophene, benzimidazole, indazole, benzoxazole, benzisoxazole, benzothiazole, isobenzofuran, isoindole, tetraline, chromane, isochromane, thiochromane, chromene, isochromene, thiochromene, indane, indene, coumarine, coumarinone, and the like, which can be further substituted. Such heteroaryl group can be bonded to other moieties within the molecule at any position.

"Substituted" or "a substituent" is hydrogen, one or more hydrocarbyl fragments, one or more heterohydrocarbyl fragments, one or more halo atoms, one or more functional groups, or combinations thereof. Two or more substituents may themselves form an additional ring or ring system.

A functional group comprises of alkyl, aryl, alkenyl, alkynyl, halo, haloalkyl, hydroxyl, alkoxyl, hydroxyalkyl, oxo, alkylcarbonyl, formyl, carboxyl, alkylcarboxylate, alkylamide, aminocarbonyl, amino, cyano, diazo, nitro, thio, sulfoxyl, sulfonyl, phosphate, phosphinate, and one of the moieties depicted below.

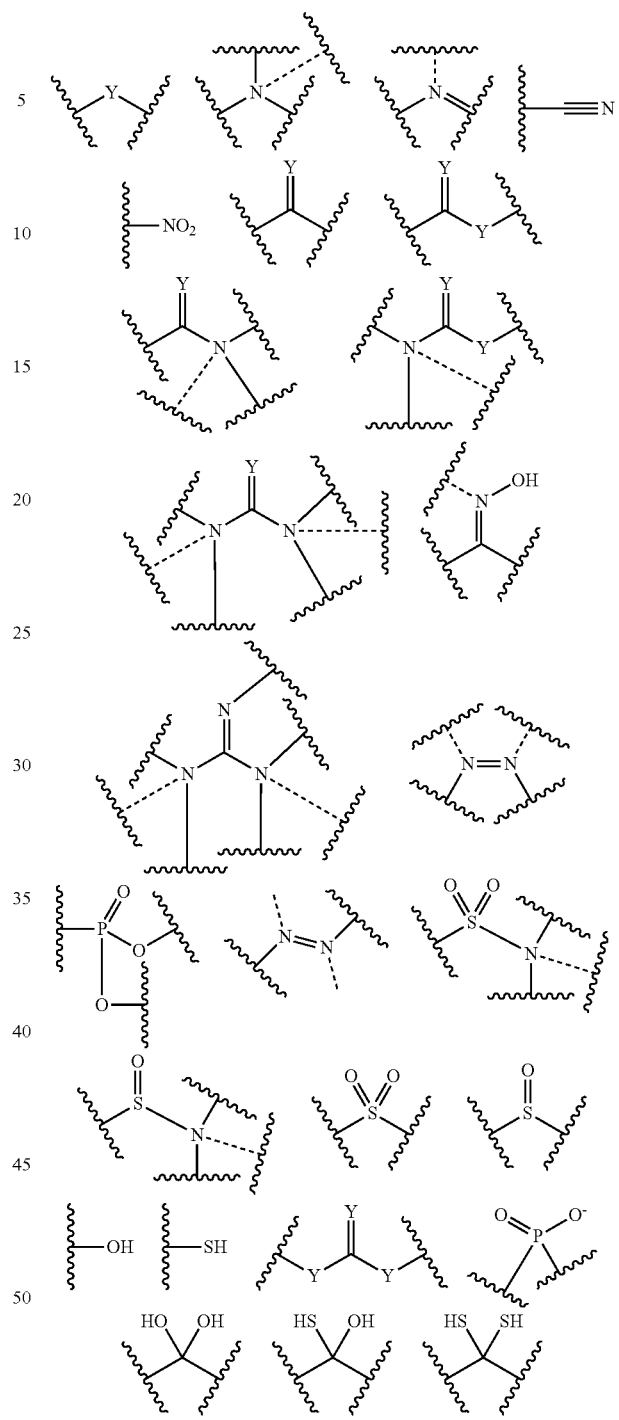

If a functional group is asymmetric, it may be oriented in any way possible. For example, the ester functional group is intended to indicate both of the structures below.

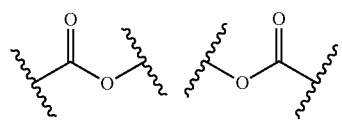 [SMILES: *OC(*)=O ; *OC(*)=O]

In a substituent, one or more hydrocarbyl fragments, one or more heterohydrocarbyl fragments, and/or one or more functional groups may be incorporated into one or more rings or ring systems.

The dashed lines on the functional groups indicate that any nitrogen atom on a functional group may form an additional bond with another carbon atom, a hydrogen atom, or may form a double bond with one of the depicted bonds so that an ammonium or a quaternary ammonium type of functional group is formed. Thus, the dashed line functional groups actually represent a group of individual functional groups. For example, the functional group:

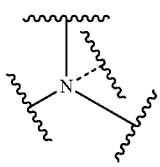

represents the following possible structures:

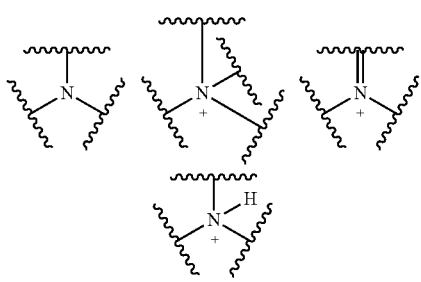

Similarly, the functional group:

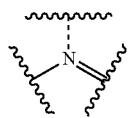

represents the following possible structures:

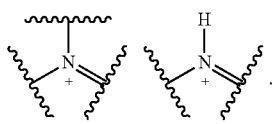

In one embodiment, compounds of the invention are represented by the structural formula

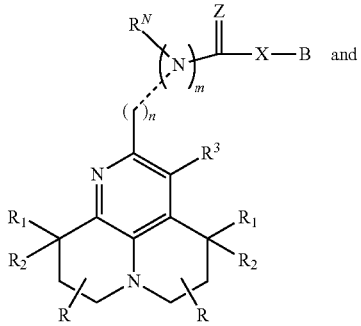 and

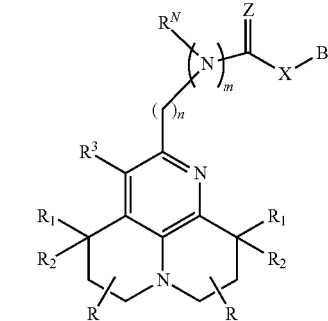

wherein m is an integer of 0, or 1; n is an integer of 0, 1, 2, or 3;

Z and X are each independently selected from the group of oxygen sulfur, and amine moiety $NR^N$;

B is selected from the group consisting of hydrogen, hydrocarbyl, heterohydrocarbyl, substituted or unsubstituted aryl, halohydrocarbyl, hydroxyl, alkoxyl, hydroxyalkyl, alkylcarbonyl, carbonylalkyl, formyl, oxycarbonyl, aminocarbonyl, alkyl carboxyl, alkyl amide, amino, alkylamino, cyano and X—B together being a heterocyclic ring or ring system;

R and $R^3$ are each independently selected from the group consisting of hydrogen, hydrocarbyl, heterohydrocarbyl, substituted or unsubstituted aryl, halo, halohydrocarbyl, hydroxyl, alkoxyl, hydroxyalkyl, alkylcarbonyl, carbonylalkyl, formyl, oxycarbonyl, aminocarbonyl, alkyl carboxyl, alkyl amide, amino, alkylamino, and cyano;

each $R^1$ is independently selected from the group consisting of hydrogen, hydrocarbyl, heterohydrocarbyl, substituted or unsubstituted aryl, halo, halohydrocarbyl, hydroxyl, alkoxyl, hydroxyalkyl, alkylcarbonyl, formyl, oxycarbonyl, aminocarbonyl, aminocarbonxyl, alkylcarboxyl, alkyl alkylcarbonyl, formyl, oxycarbonyl, aminocarbonyl, aminocarbonxyl, alkylcarboxyl, alkyl amide, amino, alkylamino, and cyano;

each $R^2$ is independently selected from the group consisting of hydrocarbyl, heterohydrocarbyl, substituted or unsubstituted aryl, halo, halohydrocarbyl, hydroxyl, alkoxyl, hydroxyalkyl, alkylcarbonyl, formyl, oxo, oxycarbonyl, carboxyl, alkyl carboxylate, alkyl amide, aminocarbonyl, amino, alkylamino, and cyano; each $R^N$ is independently selected from the group consisting of hydrogen, hydrocarbyl, heterohydrocarbyl, substituted or unsubstituted aryl, halohydrocarbyl, hydroxyl, alkoxyl, hydroxyalkyl, alkylcarbonyl, carbonylalkyl, formyl, oxycarbonyl, aminocarbonyl, alkyl carboxyl, alkyl amide, amino, alkylamino, and cyano; including their alternate solid forms, tautomers, stereoisomers, enantiomers, diastereomers, prodrugs, and pharmaceutically acceptable salts, hydrates and solvates.

In another embodiment, compounds of the invention are represented by the structural formula

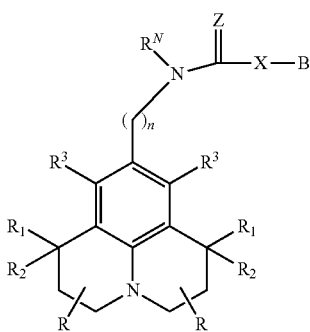

wherein
n is 0, 1, 2, or 3;
Z is O, S, or $NR^N$;
X is O, S, or $NR^N$;
B is selected from the group consisting of hydrogen, hydrocarbyl, heterohydrocarbyl, substituted or unsubstituted aryl, halohydrocarbyl, hydroxyl, alkoxyl, hydroxyalkyl, alkylcarbonyl, carbonylalkyl, formyl, oxycarbonyl, aminocarbonyl, alkyl carboxyl, alkyl amide, amino, alkylamino, cyano and X—B together being a heterocyclic ring;

R and $R^3$ are each independently selected from the group consisting of hydrogen, hydrocarbyl, heterohydrocarbyl, substituted or unsubstituted aryl, halo, halohydrocarbyl, hydroxyl, alkoxyl, hydroxyalkyl, alkylcarbonyl, carbonylalkyl, formyl, oxycarbonyl, aminocarbonyl, alkyl carboxyl, alkyl amide, amino, alkylamino, and cyano;

each $R^1$ is independently selected from the group consisting of hydrogen, hydrocarbyl, heterohydrocarbyl, substituted or unsubstituted aryl, halo, halohydrocarbyl, hydroxyl, alkoxyl, hydroxyalkyl, alkylcarbonyl, formyl, oxycarbonyl, aminocarbonyl, aminocarbonxyl, alkylcarboxyl, alkyl amide, amino, alkylamino, and cyano;

each $R^2$ is independently selected from the group consisting of hydrocarbyl, heterohydrocarbyl, substituted or unsubstituted aryl, halo, halohydrocarbyl, hydroxyl, alkoxyl, hydroxyalkyl, alkylcarbonyl, formyl, oxo, oxycarbonyl, carboxyl, alkyl carboxylate, alkyl amide, aminocarbonyl, amino, alkylamino, and cyano;

each $R^N$ is independently selected from the group consisting of hydrogen, hydrocarbyl, heterohydrocarbyl, substituted or unsubstituted aryl, halohydrocarbyl, hydroxyl, alkoxyl, hydroxyalkyl, alkylcarbonyl, carbonylalkyl, formyl, oxycarbonyl, aminocarbonyl, alkyl carboxyl, alkyl amide, amino, alkylamino, and cyano;

including its alternate solid forms, tautomers, stereoisomers, enantiomers, diastereomers, prodrugs, and pharmaceutically acceptable salts, hydrates and solvates.

In yet another embodiment, the compounds are represented by

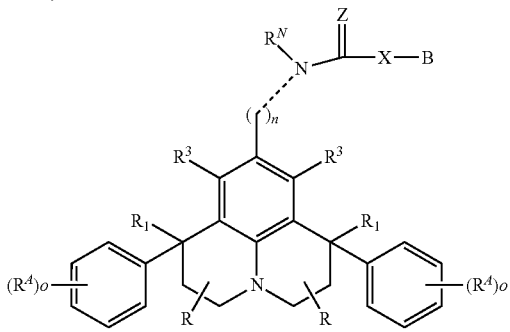

wherein o is an integer of 0, 1, 2, or 3;
Z is O or S;

each $R^A$ is independently selected from the group consisting of hydrogen, hydrocarbyl, heterohydrocarbyl, substituted or unsubstituted aryl, halo, halohydrocarbyl, hydroxyl, alkoxyl, hydroxyalkyl, alkylcarbonyl, carbonylalkyl, formyl, oxycarbonyl, aminocarbonyl, alkyl carboxyl, alkyl amide, amino, alkylamino, and cyano;

R and $R^3$ are each independently selected from the group consisting of hydrogen and a substituent having a formula $C_{0-12}H_{0-30}N_{0-3}O_{0-5}P_{0-2}S_{0-3}F_{0-6}Cl_{0-3}Br_{0-3}I_{0-3}$;

each $R^N$ is independently selected from the group consisting of hydrogen and $C_{1-12}$ hydrocarbyl;

B is selected from the group consisting of hydrogen, a substituent having a formula $C_{0-12}H_{0-30}N_{0-3}O_{0-5}P_{0-2}S_{0-3}F_{0-6}Cl_{0-3}Br_{0-3}I_{0-3}$, wherein if X is $NR^N$, and X—B being a heterocyclic ring/ring system. The formula $C_{0-12}H_{0-30}N_{0-3}O_{0-5}P_{0-2}S_{0-3}F_{0-6}Cl_{0-3}Br_{0-3}I_{0-3}$ represents a structure having from 0-12 carbon atoms, from 0-30 hydrogen atoms, from 0-3 nitrogen atoms, from 0-5 oxygen atoms, from 0-2 phosphorous atoms, from 0-3 sulfur atoms, from 0-6 fluorine atoms, from 0-3 chlorine atoms, from 0-3 bromine atoms, and from 0-3 iodine atoms.

In yet another embodiment, each $R^A$ is independently hydrogen, alkyl, aryl, alkenyl, alkynyl, halo, haloalkyl, hydroxyl, alkoxyl, hydroxyalkyl, alkylcarbonyl, formyl, carboxyl, alkyl carboxylate, alkyl amide, aminocarbonyl, amino, cyano, diazo, nitro, thio, sulfoxyl, sulfonyl, phosphate, or phosphinate.

In another embodiment, X is O.

In another embodiment, Z is O.

In another embodiment, Z is S.

In another embodiment, B is $C_{1-6}$ alkyl, $C_{1-6}$ alkenyl, $C_{1-6}$ alkynyl, $C_{1-6}$ haloalkyl, hydroxyalkyl, phenyl, benzyl, furylmethyl, or wherein X—B is morpholino. $C_{1-6}$ means having from one to six (1-6) carbon atoms. $C_{1-6}$ haloalkyl is $C_{1-6}$ alkyl having at least one halo atoms of F, Cl, Br, or I as the substituent. Examples of haloalkyl include —CH2F, —CH$_2$CHF$_2$, —C$_3$H$_6$F, —C$_4$H$_8$F, —C$_5$H$_{10}$F, —C$_6$H$_{12}$F, fluorocyclopropyl, fluorocyclobutyl, fluorocyclopentyl, fluorocyclohexyl, —CH$_2$CH$_2$Cl, —C$_3$H$_6$Cl, —C$_4$H$_8$Cl, —C$_6$H$_{10}$Cl, —C$_6$H$_{12}$Cl, chlorocyclopropyl, chlorocyclobutyl, chlorocyclopentyl, chlorocyclohexyl, —CH$_2$CH$_2$Br, —C$_3$H$_6$Br, —C$_4$H$_8$Br, —C$_6$H$_{10}$Br, —C$_6$H$_{12}$Br, bromocyclopropyl, bromocyclobutyl, bromocyclopentyl, bromocyclohexyl, —CH$_2$CH$_2$I, —C$_3$H$_6$I, —C$_4$H$_8$I, —C$_6$H$_{10}$I, —C$_6$H$_{12}$I, iodocyclopropyl, iodocyclobutyl, iodocyclopentyl, and iodocyclohexyl. Morpholino is:

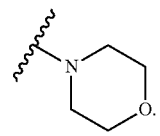 [SMILES: *N1CCOCC1]

In another embodiment, $R^A$ is hydrogen, $C_{1-12}$ alkyl, $C_{1-12}$ alkenyl, $C_{1-12}$ alkynyl, halo, $C_{1-12}$ halohydrocarbyl, $C_{1-12}$ hydroxyalkyl, $C_{3-12}$ cyclic hydrocarbyl, or heteroaryl. $C_{1-12}$ means having from 1-12 carbon atoms.

In yet another embodiment, X is $NR^N$.

In another embodiment, the compounds can be represented by the structural formula:

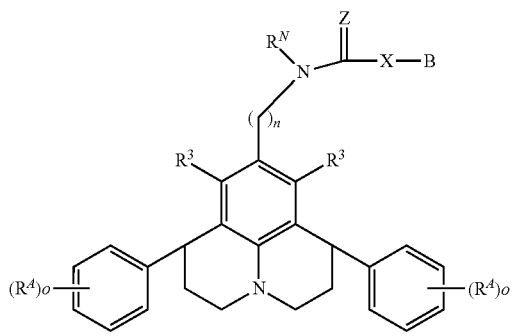

wherein each $R^A$ is independently hydrogen, $C_{1-12}$ alkyl, $C_{1-12}$ alkenyl, $C_{1-12}$ alkynyl, halo, $C_{1-12}$ halohydrocarbyl, $C_{1-12}$ hydroxyalkyl, $C_{3-12}$ cyclic hydrocarbyl, or heteroaryl.

In another embodiment, $R^N$ is hydrogen, methyl, ethyl, propyl, or isopropyl.

In one embodiment, $R^N$ is hydrogen, $C_{1-6}$ alkyl or phenyl.

In another embodiment, B is hydrocarbyl, as described above.

In yet another embodiment, B is substituted or unsubstituted hydrocarbon-aryl or heterohydrocarbyl. Examples of heteroaryl include pyridine, pyrazine, pyrimidine, pyridazine, triazine, furan, pyrrole, thiophene, imidazole, pyrazole, oxazole, isoxazole, thiazole, isothiazole, oxadiazole, thiadiazole, naphthalene, quinoline, quinoxaline, quinazoline, cinnoline, isoquinoline, benzofuran, indole, benzothiophene, benzimidazole, indazole, benzoxazole, benzisoxazole, benzothiazole, isobenzofuran, isoindole, tetraline, chromane, isochromane, thiochromane, chromene, isochromene, thiochromene, indane, indene, coumarine, coumarinone, and the like.

If the aryl or heteroaryl is substituted, the substituents are the same as those defined above. Examples include alkyl, aryl, alkenyl, alkynyl, halo, haloalkyl, hydroxyl, alkoxyl, hydroxyalkyl, alkylcarbonyl, formyl, carboxyl, alkyl carboxylate, alkyl amide, aminocarbonyl, amino, cyano, diazo, nitro, thio, sulfoxyl, sulfonyl, phosphate, phosphinate, and the like.

B may also be a combination of one or more of hydrogen, hydrocarbyl, heterohydrocarbyl, substituted or unsubstituted hydrocarbon-aryl, or substituted or unsubstituted heteroaryl. For example, B may have one of the structures shown below:

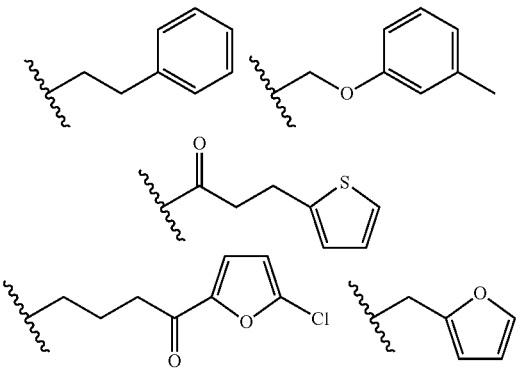

Compounds according to the structural formulas below are also contemplated:

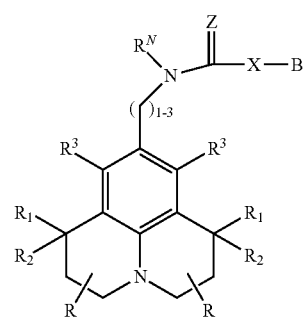

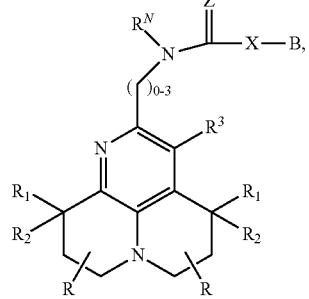

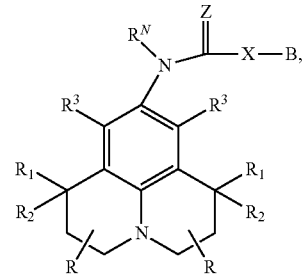

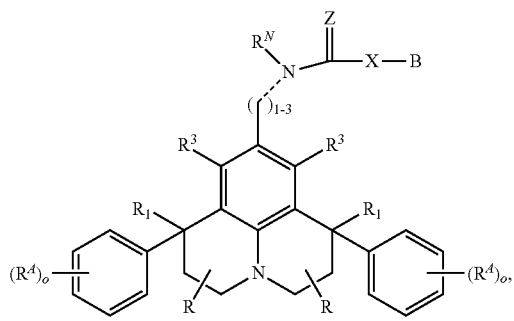

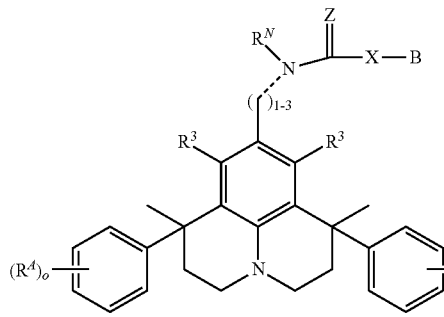

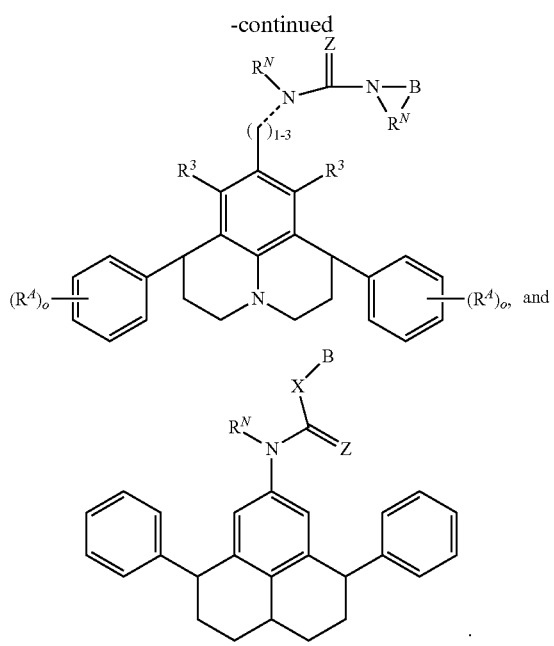

wherein o is an integer of 0, 1, 2, or 3; Z is O or S;

each $R^A$ is independently selected from the group consisting of hydrogen, hydrocarbyl, heterohydrocarbyl, substituted or unsubstituted aryl, halo, halohydrocarbyl, hydroxyl, alkoxyl, hydroxyalkyl, alkylcarbonyl, carbonylalkyl, formyl, oxycarbonyl, aminocarbonyl, alkyl carboxyl, alkyl amide, amino, alkylamino, and cyano;

R and $R^3$ are each independently selected from the group consisting of hydrogen and a substituent having a formula $C_{0-12}H_{0-30}N_{0-3}O_{0-5}P_{0-2}S_{0-3}F_{0-6}Cl_{0-3}Br_{0-3}I_{0-3}$;

each $R^N$ is independently selected from the group consisting of hydrogen and $C_{1-12}$ hydrocarbyl;

B is selected from the group consisting of hydrogen, a substituent having a formula $C_{0-12}H_{0-30}N_{0-3}O_{0-5}P_{0-2}S_{0-3}F_{0-6}Cl_{0-3}Br_{0-3}I_{0-3}$, wherein if X is $NR^N$, and X—B being a heterocyclic ring/ring system. The formula $C_{0-12}H_{0-30}N_{0-3}O_{0-5}P_{0-2}S_{0-3}F_{0-6}Cl_{0-3}Br_{0-3}I_{0-3}$ represents a structure having from 0-12 carbon atoms, from 0-30 hydrogen atoms, from 0-3 nitrogen atoms, from 0-5 oxygen atoms, from 0-2 phosphorous atoms, from 0-3 sulfur atoms, from 0-6 fluorine atoms, from 0-3 chlorine atoms, from 0-3 bromine atoms, and from 0-3 iodine atoms.

In yet another embodiment, each $R^A$ is independently hydrogen, alkyl, aryl, alkenyl, alkynyl, halo, haloalkyl, hydroxyl, alkoxyl, hydroxyalkyl, alkylcarbonyl, formyl, carboxyl, alkyl carboxylate, alkyl amide, aminocarbonyl, amino, cyano, diazo, nitro, thio, sulfoxyl, sulfonyl, phosphate, or phosphinate.

In another embodiment, X is O.

In another embodiment, Z is O.

In another embodiment, Z is S.

In another embodiment, B is $C_{1-6}$ alkyl, $C_{1-6}$ alkenyl, $C_{1-6}$ alkynyl, $C_{1-6}$ haloalkyl, hydroxyalkyl, phenyl, benzyl, furylmethyl, or wherein X—B is morpholino. $C_{1-6}$ means having from one to six (1-6) carbon atoms. $C_{1-6}$ haloalkyl is $C_{1-6}$ alkyl having at least one halo atoms of F, Cl, Br, or I as the substituent. Examples of haloalkyl include —CH2F, —CH$_2$CHF$_2$, —C$_3$H$_6$F, —C$_4$H$_8$F, —C$_5$H$_{10}$F, —C$_6$H$_{12}$F, fluorocyclopropyl, fluorocyclobutyl, fluorocyclopentyl, fluorocyclohexyl, —CH$_2$CH$_2$Cl, —C$_3$H$_6$Cl, —C$_4$H$_8$Cl, —C$_5$H$_{10}$Cl, —C$_6$H$_{12}$Cl, chlorocyclopropyl, chlorocyclobu-tyl, chlorocyclopentyl, chlorocyclohexyl, —CH$_2$CH$_2$Br, —C$_3$H$_6$Br, —C$_4$H$_8$Br, —C$_5$H$_{10}$Br, —C$_6$H$_{12}$Br, bromocyclopropyl, bromocyclobutyl, bromocyclopentyl, bromocyclohexyl, —CH$_2$CH$_2$I, —C$_3$H$_6$I, —C$_4$H$_8$I, —C$_5$H$_{10}$I, —C$_6$H$_{12}$I, iodocyclopropyl, iodocyclobutyl, iodocyclopentyl, iodocyclohexyl Specific compounds of the present invention include:

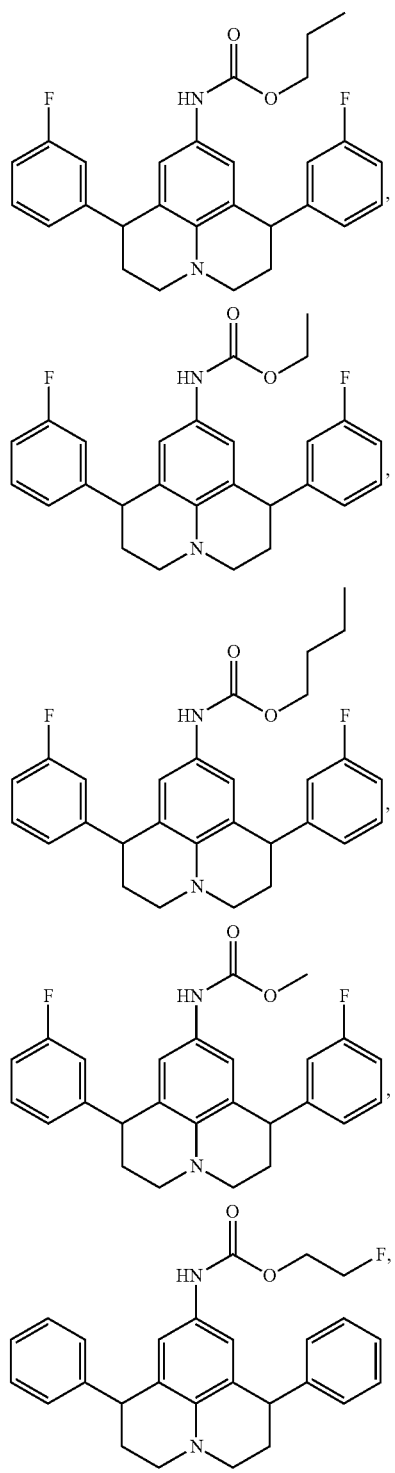

17
-continued
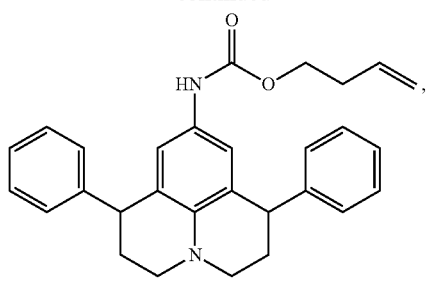
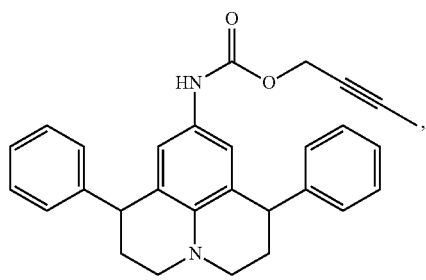
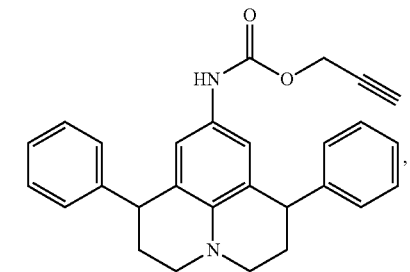
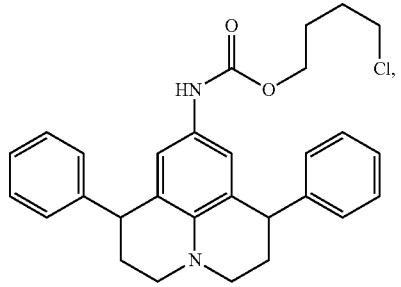
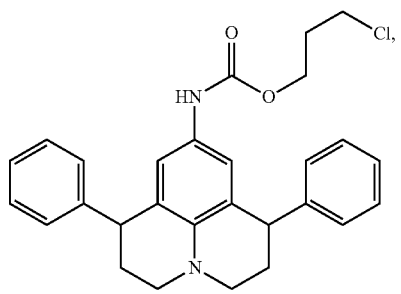
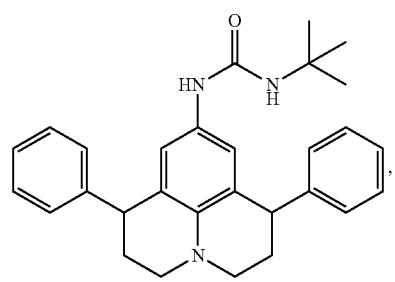
18
-continued
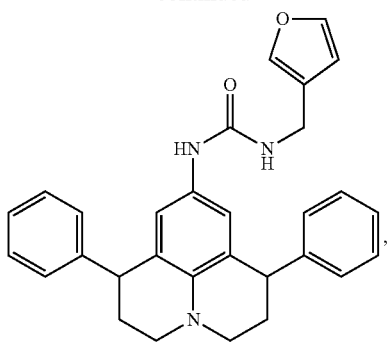
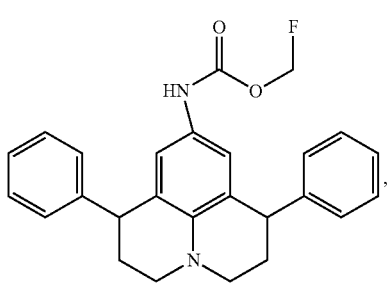
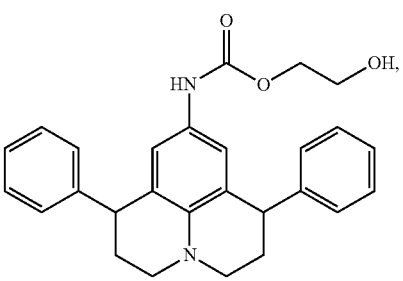
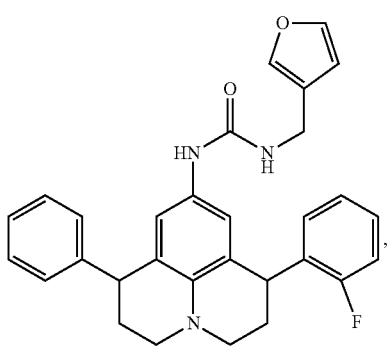
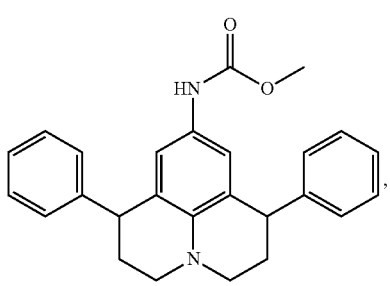

19
-continued
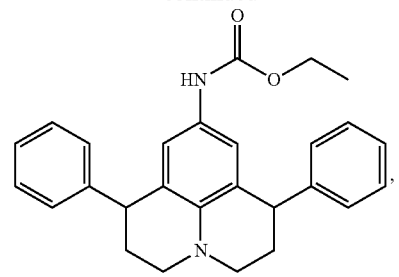
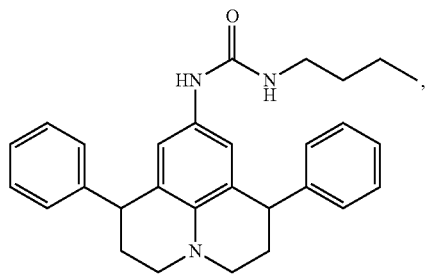
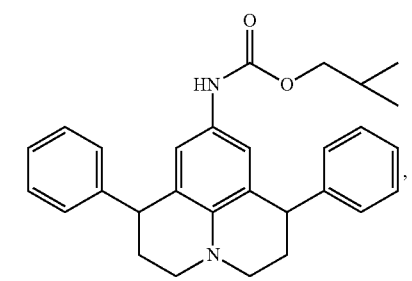
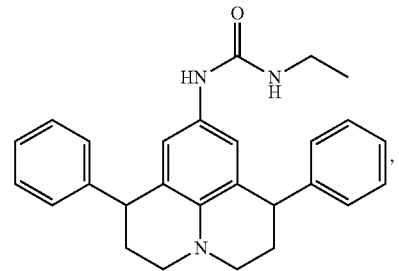
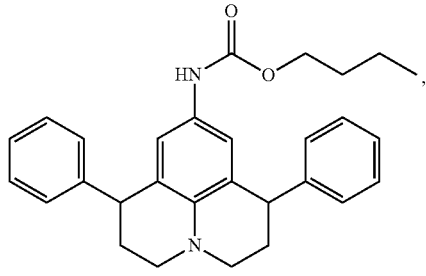
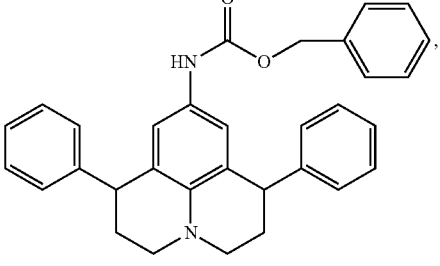
20
-continued
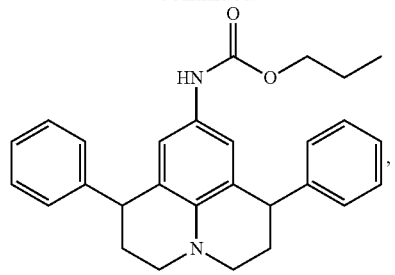
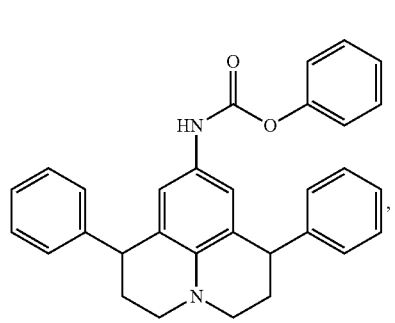
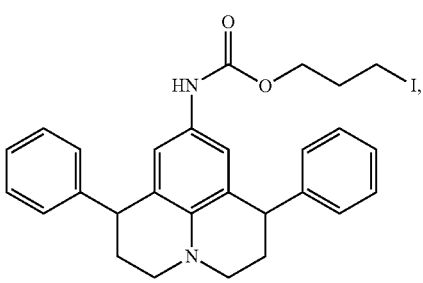
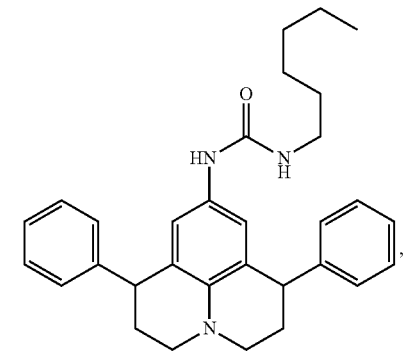
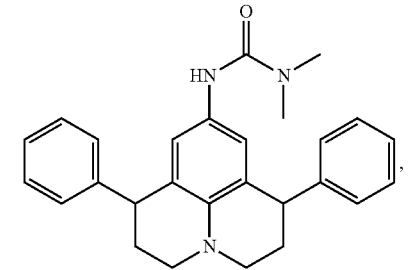

21
-continued
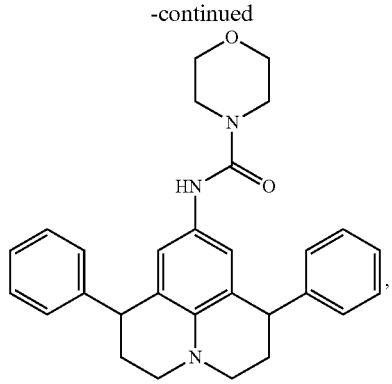
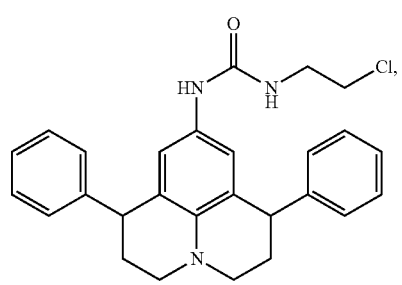
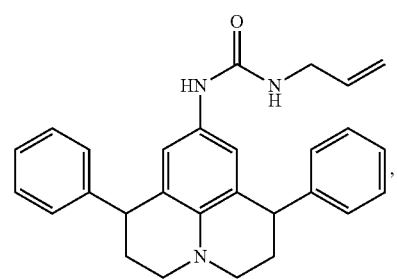
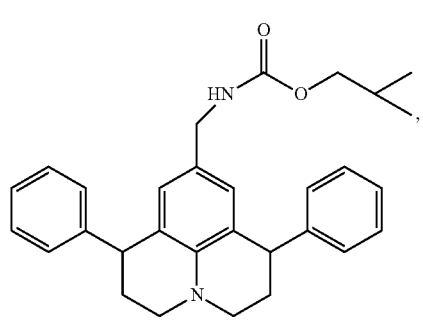
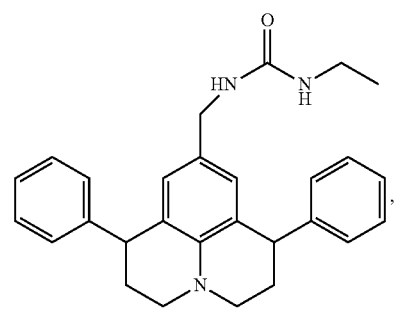
22
-continued
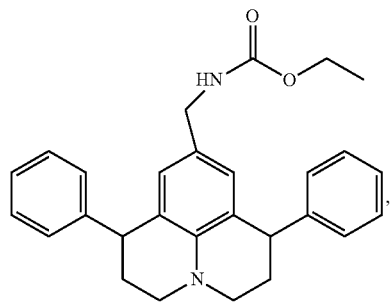
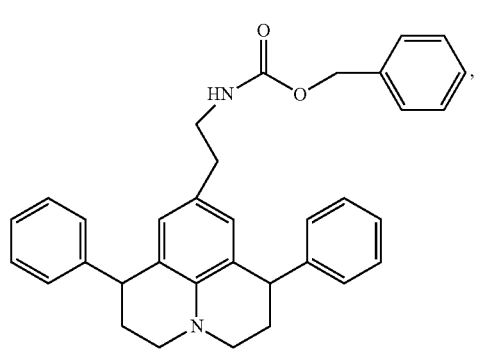
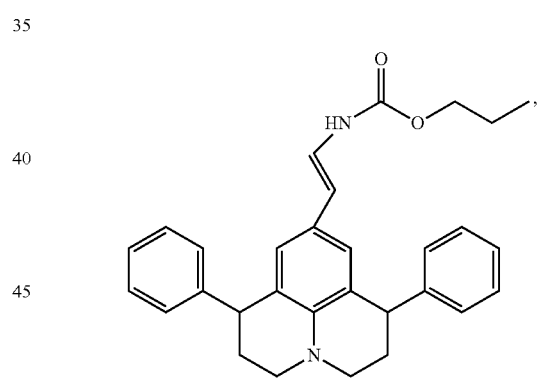
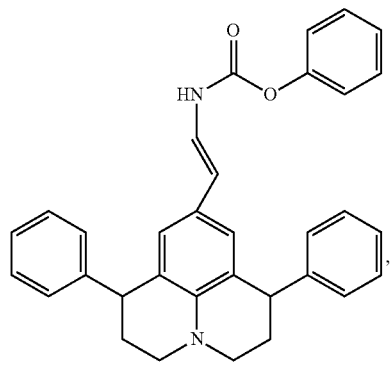

-continued

25
-continued
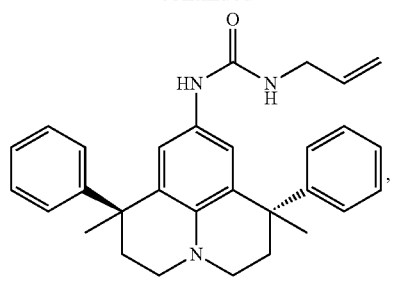
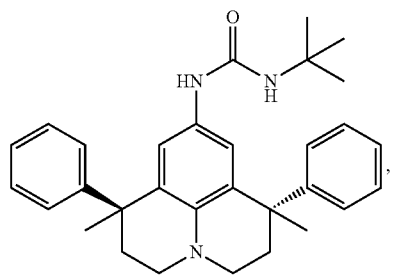
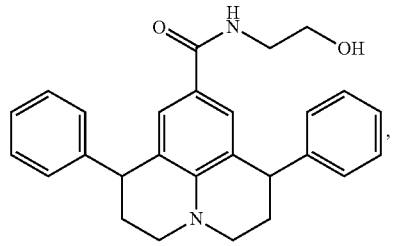
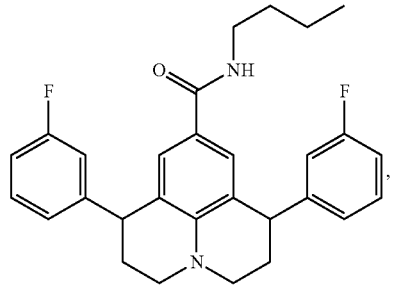
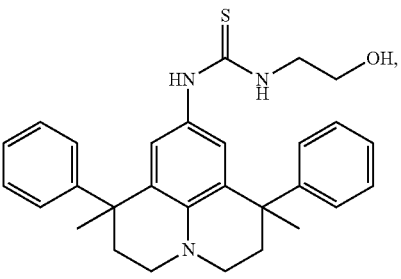
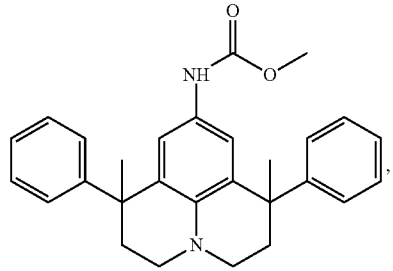
26
-continued
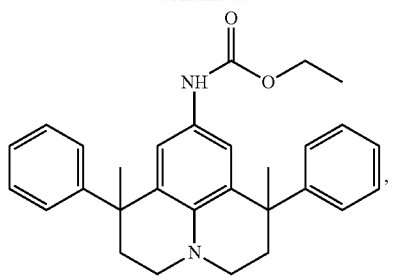
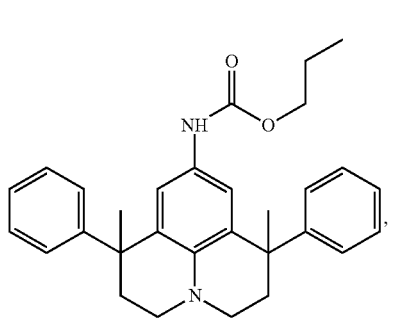
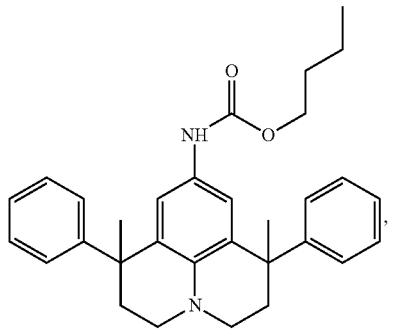
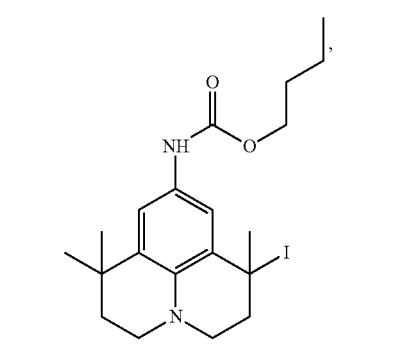
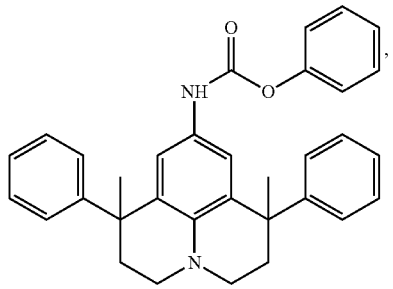

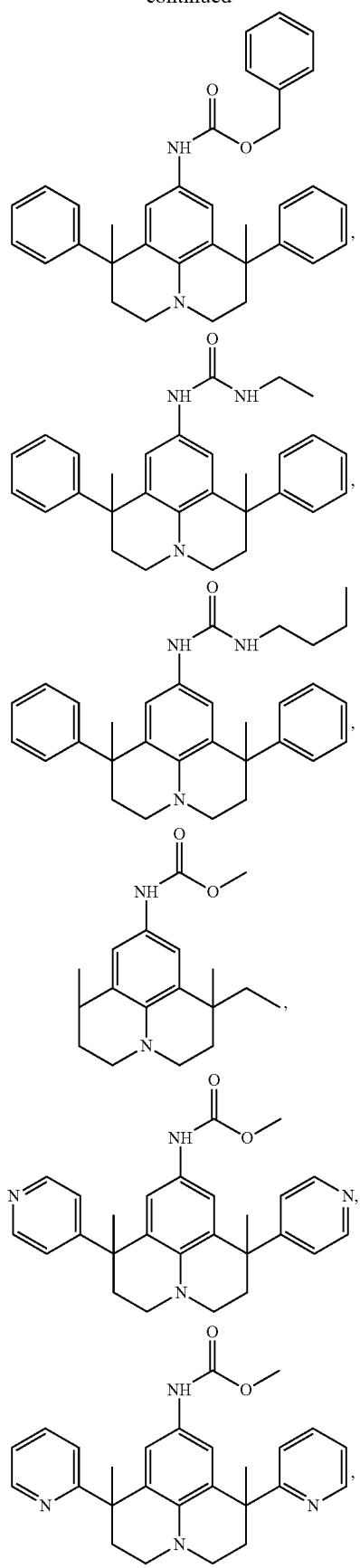
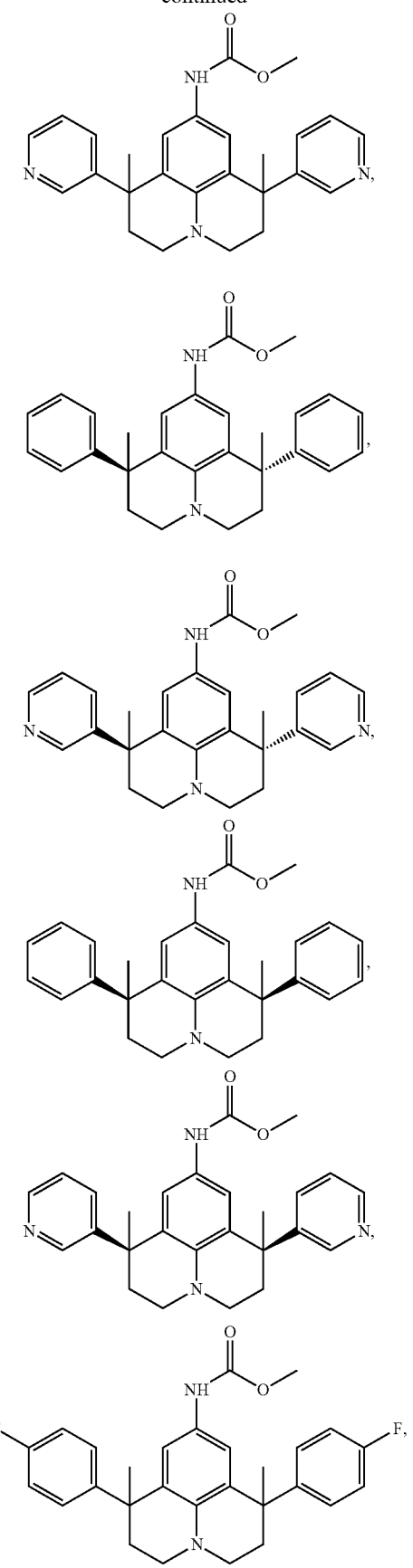

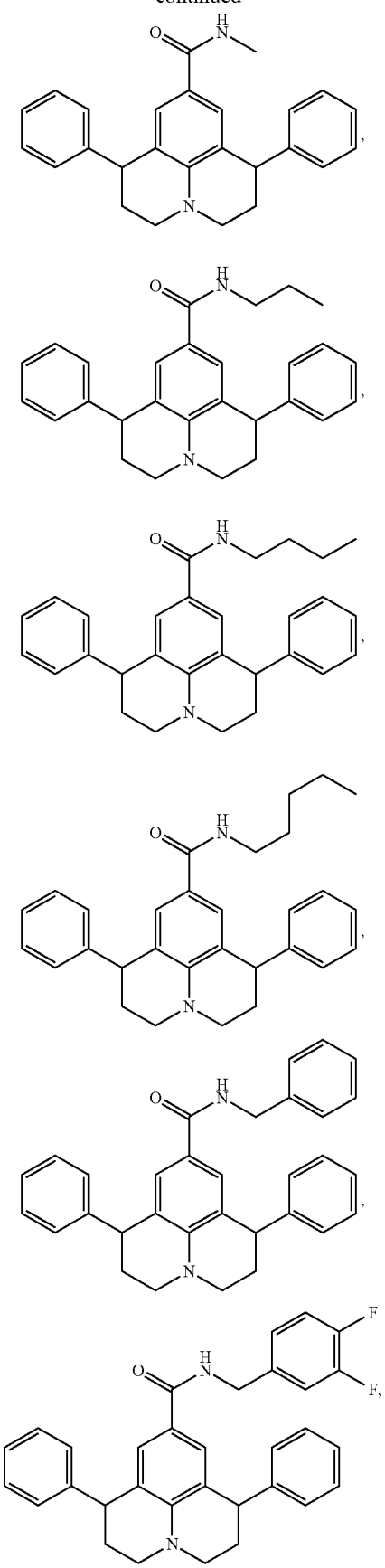
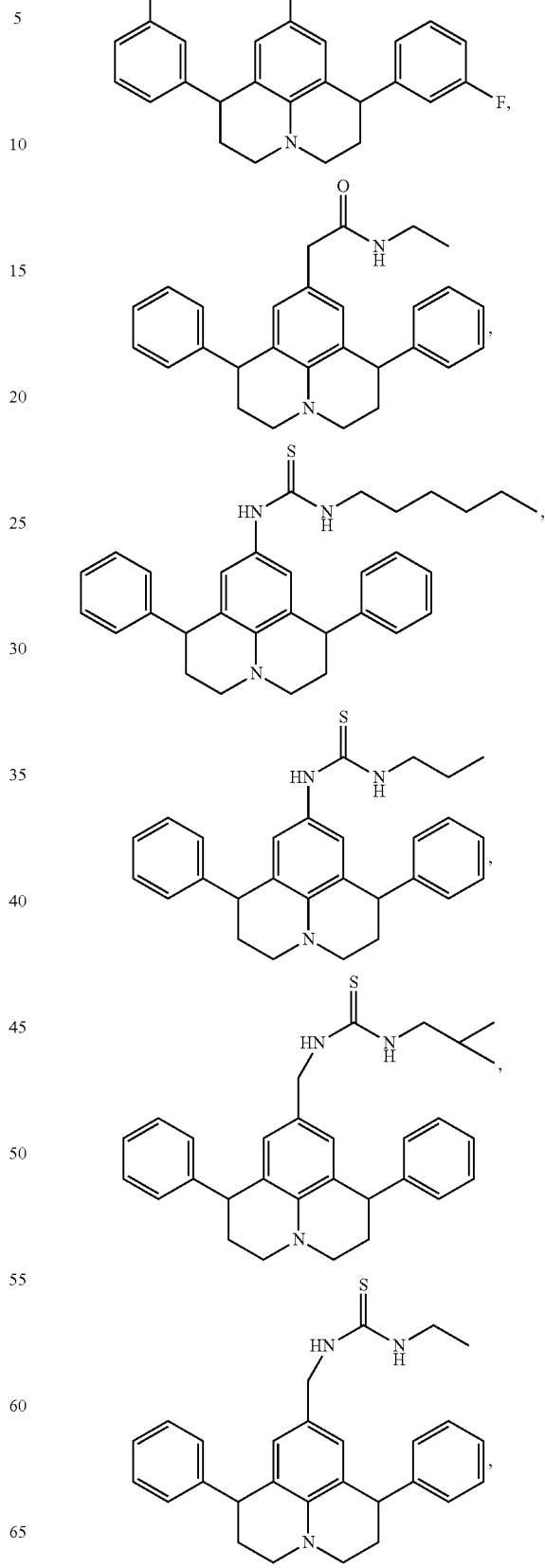

-continued

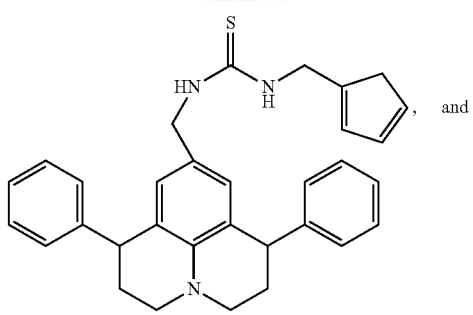
, and

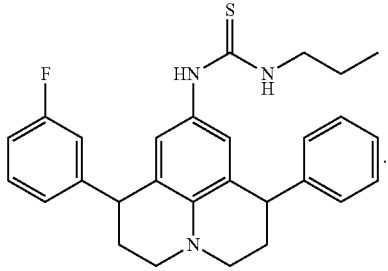
.

The compounds of the present invention can be combined with at least one other therapeutic agent that is already known the art. The compounds of invention and the other therapeutic agent(s) can act additively, or more preferably, synergistically.

The invention is further defined by reference to the following examples, which describe the preparation schemes and methods for obtaining the compounds of the invention, the assays for testing the biological activities of these compounds. It will be apparent to those skilled in the art that many modifications, both to the preparation schemes and assays, may be practiced without departing from the scope of the invention.

EXAMPLES

Organic Synthesis

Reaction Schemes A, B, C, D and E are examples of the preparation methods for obtaining the compounds of the invention.

Reaction Scheme A

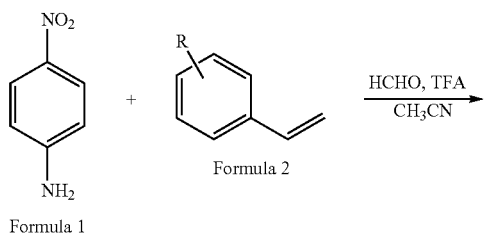

-continued

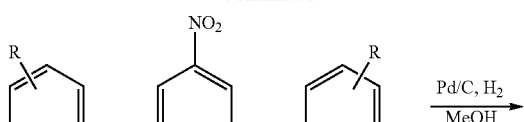

Formula 3

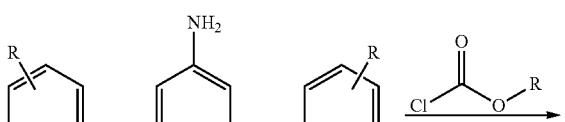

Formula 4

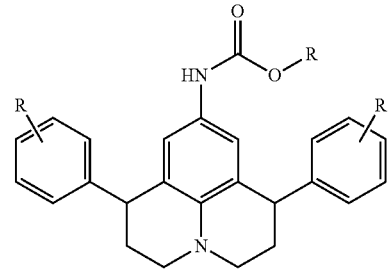

Formula 5

Reaction Scheme B

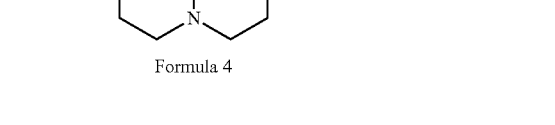

Formula 4

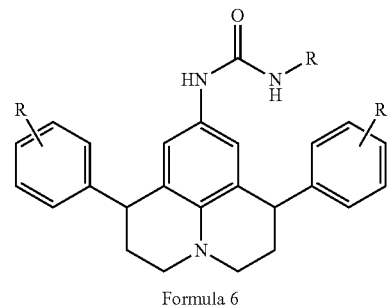

Formula 6

Reaction Scheme C
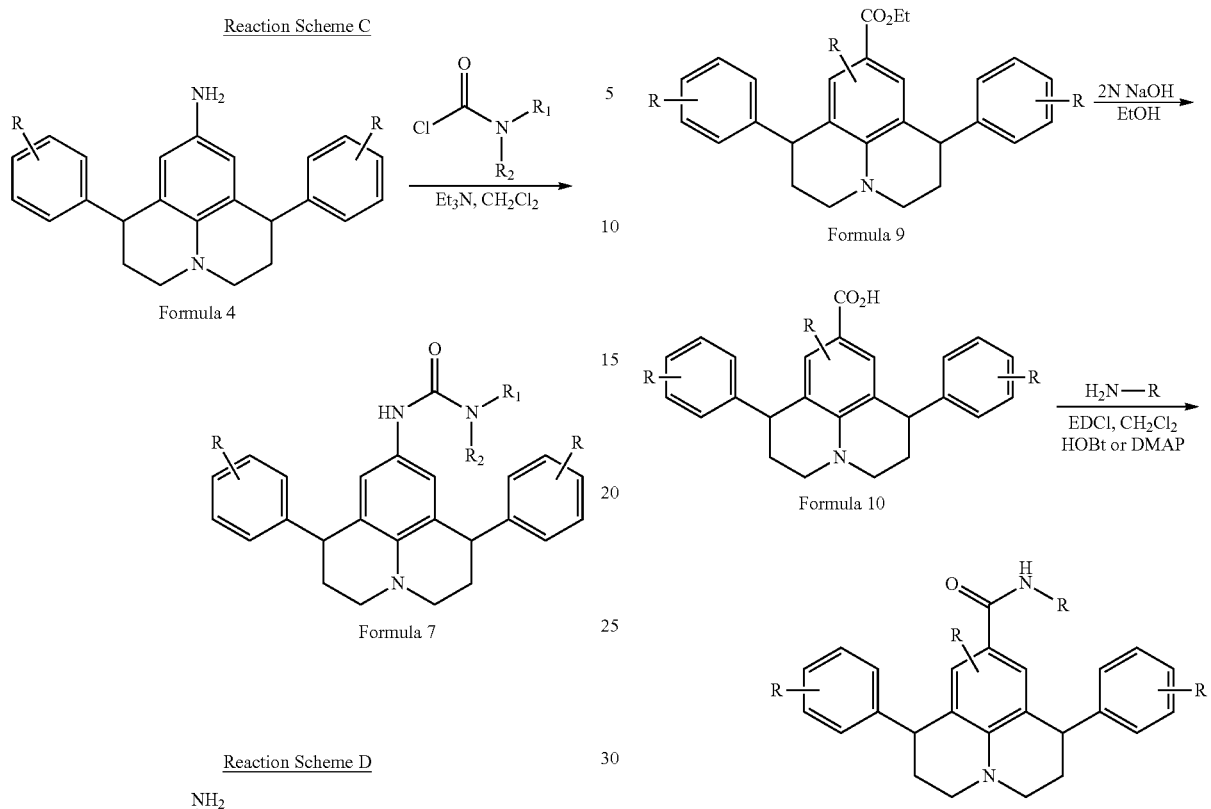
Reaction Scheme D
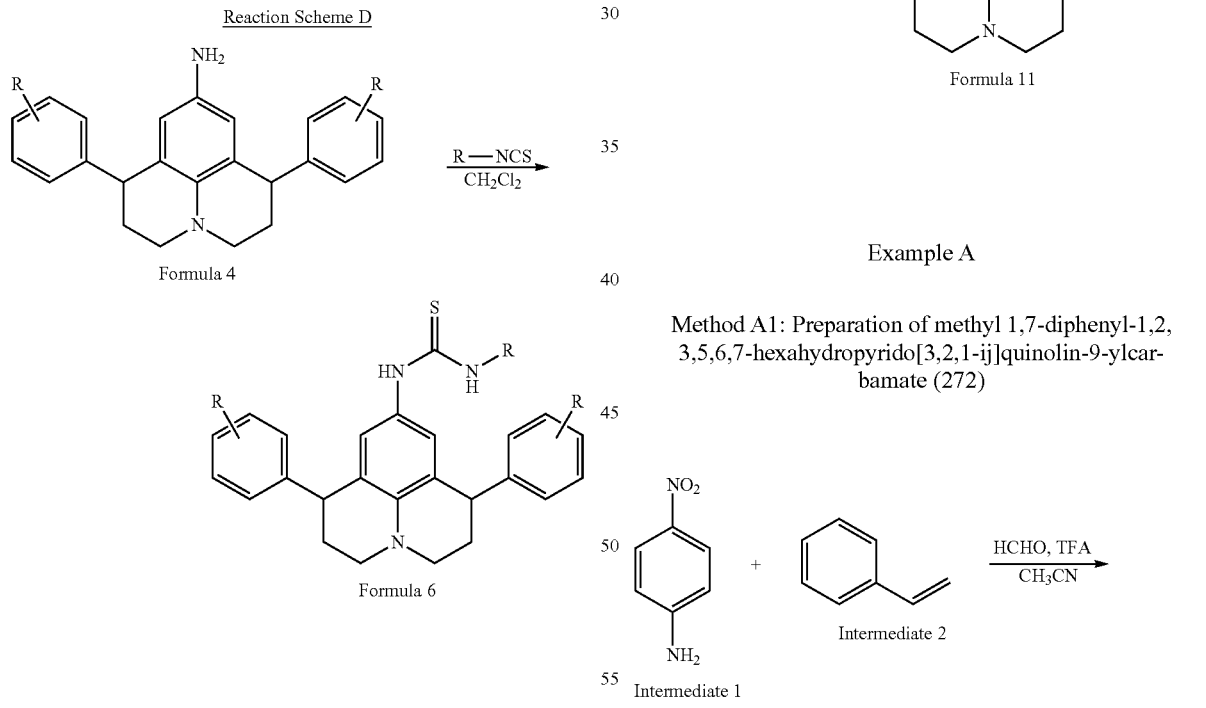
Reaction Scheme E
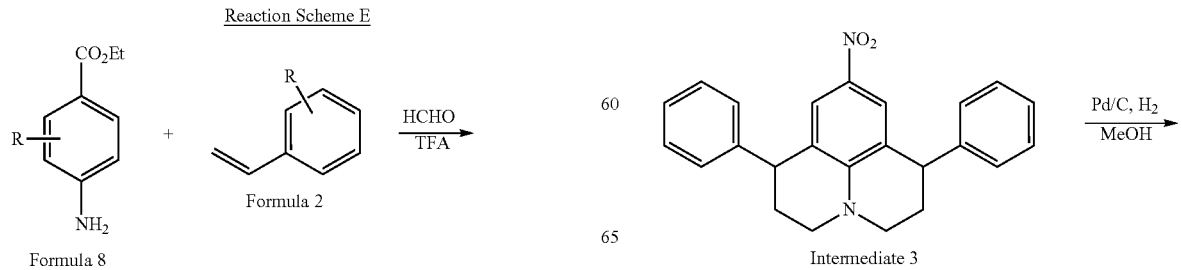
Example A
Method A1: Preparation of methyl 1,7-diphenyl-1,2,3,5,6,7-hexahydropyrido[3,2,1-ij]quinolin-9-ylcarbamate (272)

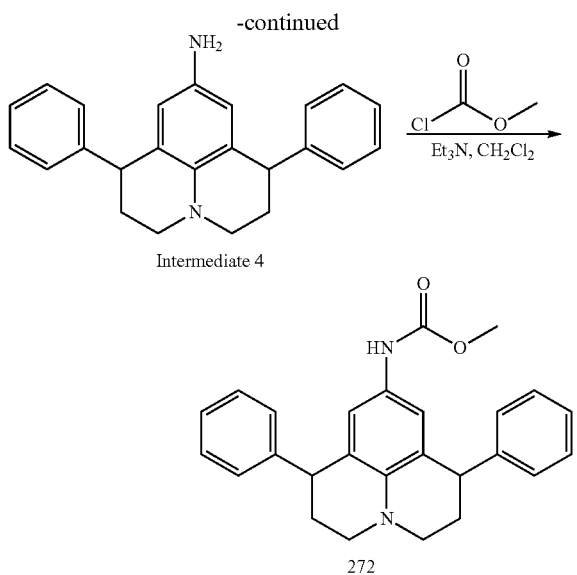

To a solution 4-Nitroaniline (Intermediate 1) (1.8 g, 10 mmol) in acetonitrile (8 mL) was added one equivalent of trifluoroacetic acid (1.14 g, 10 mmol). To this suspension was added with stirring a heterogeneous mixture of styrene (Intermediate 2), (5.74 mL, 50 mmol) and 37% formaldehyde solution (4.06 mL, 50 mmol) under argon, which gave a yellow precipitate. The precipitate failed to re-dissolve after 30 min. of stirring at room temperature, so the mixture was heated at reflux under argon for further 30 min, during which time the precipitate re-dissolved. The reaction mixture was cooled to room temperature. The precipitate was filtered and wash with acetonitrile gave yellow solid, 9-nitro-1,7-diphenyl-1,2,3,5,6,7-hexahydropyrido[3,2,1-ij]quinoline (Intermediate 3), (1.53 g, 41%).

A solution of 9-nitro-1,7-diphenyl-1,2,3,5,6,7-hexahydropyrido[3,2,1-ij]quinoline (Intermediate 3), (1.2 g, 7.06 mmol), in MeOH (100 mL) was subjected to hydrogenation reaction by the action of 10% Pd/C (120 mg) under H$_2$ balloon at room temperature for 12 h. The mixture was filtered through Celite and freed of solvent under reduced pressure to get 1,7-diphenyl-1,2,3,5,6,7-hexahydropyrido[3,2,1-ij]quinolin-9-amine (Intermediate 4) as a solid, (1.08 g, 98%).

To a solution 1,7-diphenyl-1,2,3,5,6,7-hexahydropyrido[3,2,1-ij]quinolin-9-amine (Intermediate 4), (207 mg, 0.608 mmol) in dichloromethane (10 mL) was added three equivalent of triethyl amine (0.252 mL, 1.8 mmol), followed by methyl chloroformate (0.071 mL, 0.91 mmol) under argon at 0° C. The reaction mixture was then stirred at room temperature for overnight. The mixture was quenched with water (30 mL). The residue was isolated in a typical aqueous workup and purified by MPLC (medium pressure liquid chromatography) using silica gel column with 10 to 15% EtOAc:Hexane to give methyl 1,7-diphenyl-1,2,3,5,6,7-hexahydropyrido[3,2,1-ij]quinolin-9-ylcarbamate (272), (181 mg 75%). $^1$H NMR (300 MHz, CDCl$_3$) δ ppm 2.00-2.18 (m, 2H) 2.22-2.39 (m, 2H) 3.03-3.22 (m, 4H) 3.50-3.64 (m, 3H) 3.54-3.65 (m, 3H) 4.05-4.23 (m, 2H) 6.61 (br. s., 2H) 7.08-7.38 (m, 10H).

Method A2: Preparation of methyl (1S,7S)-1,7-dimethyl-1,7-diphenyl-1,2,3,5,6,7-hexahydropyrido[3,2,1-ij]quinolin-9-ylcarbamate, (829), and methyl (1R,7S)-1,7-dimethyl-1,7-diphenyl-1,2,3,5,6,7-hexahydropyrido[3,2,1-ij]quinolin-9-ylcarbamate (353)

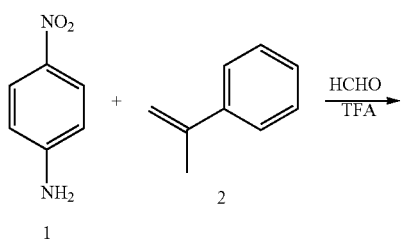

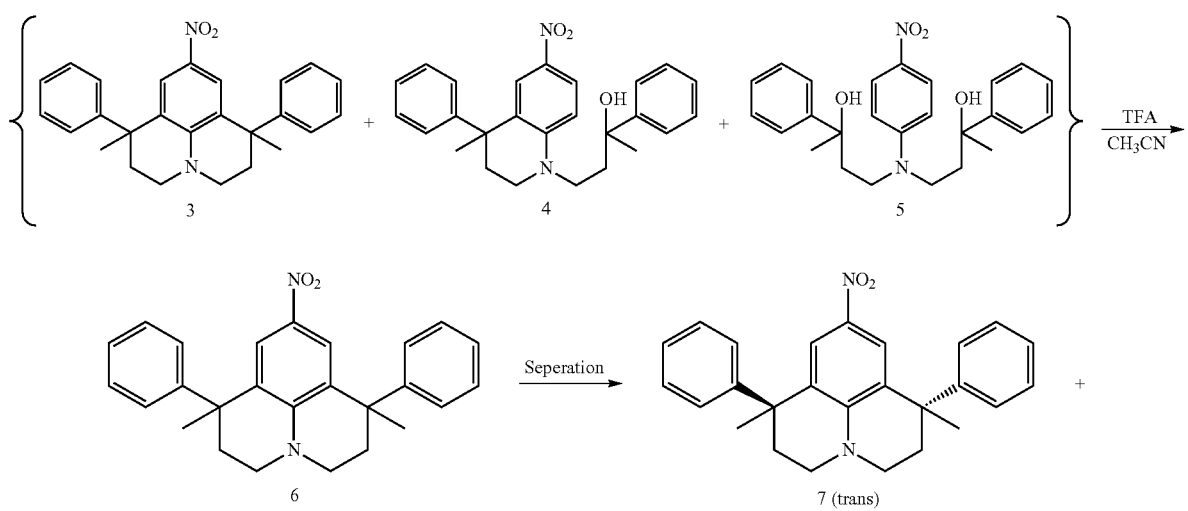

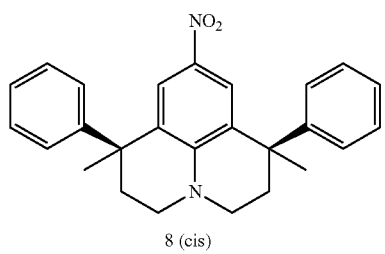 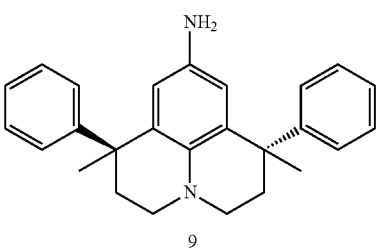 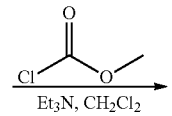

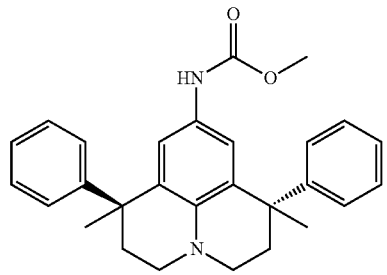 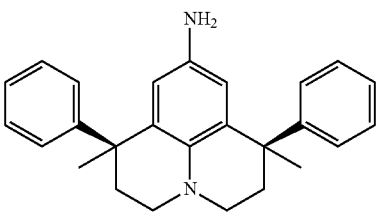 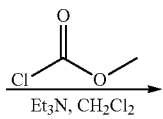

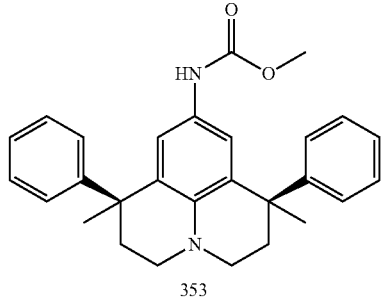

To a solution 4-Nitroaniline (1) (4.1 g, 30 mmol) in acetonitrile (30 mL) was added one equivalent of trifluoroacetic acid (2.3 mL, 30 mmol). To this suspension was added with stirring a heterogeneous mixture of styrene (2), (19.4 mL, 150 mmol) and 37% formaldehyde solution (12.2 mL, 150 mmol) under argon gave yellow precipitate. The precipitate had failed to re-dissolve after 30 min. of stirring at room temperature, so the mixture was heated at reflux under argon for further 30 min, during which time the precipitate re-dissolved. The reaction mixture was cooled to room temperature. After general workup afforded mixture of three intermediates 3 (836 mg), 4 (2 g), and 5 (4.2 g), confirmed by Mass Spectra and $^1$HNMR (see ref. John M. Mellor; et al; Tetrahedron, 1995, 6115). These intermediates were then converted into the cycloadduct product by heating at reflux with trifluoroacetic acid in acetonitrile yielded 1,7-dimethyl-9-nitro-1,7-diphenyl-1,2,3,5,6,7-hexahydropyrido[3,2,1-ij]quinoline (6) (7.036 g, 59%) as a solid. This solid product (6) was then separated to trans and cis isomers by washing with ether gave trans (7), (4.0 g) and hexane:CH$_2$Cl$_2$ gave cis (8), (2.8 g).

A mixture of (1S,7S)-1,7-dimethyl-9-nitro-1,7-diphenyl-1,2,3,5,6,7-hexahydropyrido[3,2,1-ij]quinoline (7), (2 g, 5 mmol), in THF (60 mL) was subjected to hydrogenation reaction by the action of 10% Pd/C (200 mg) under H$_2$ balloon at room temperature for 12 h. The mixture was filtered through Celite and freed of solvent under reduced pressure to get (1S,7S)-1,7-dimethyl-1,7-diphenyl-1,2,3,5,6,7-hexahydropyrido[3,2,1-ij]quinolin-9-amine (9) as a solid, (1.5 g, 100%) on the basis of recovered starting material (7), (390 mg).

Following a procedure similar to that for (9) gained (1R,7S)-1,7-dimethyl-1,7-diphenyl-1,2,3,5,6,7-hexahydropyrido[3,2,1-ij]quinolin-9-amine (10) as a solid (2.55 g, 100% yield) from (8).

To a solution (1S,7S)-1,7-dimethyl-9-nitro-1,7-diphenyl-1,2,3,5,6,7-hexahydropyrido[3,2,1-ij]quinoline (7), (115 mg, 0.31 mmol), in dichloromethane (15 mL) was added three equivalent of triethyl amine (0.129 mL, 0.93 mmol), followed by methyl chloroformate (0.031 mL, 0.406 mmol) under argon at 0° C. The reaction mixture was then stirred at room temperature for overnight. The mixture was quenched with water (30 mL). The residue was isolated in a typical aqueous workup and purified by MPLC (medium pressure liquid chromatography) using silica gel column with 10 to 15% EtOAc:Hexane to give methyl (1S,7S)-1,7-dimethyl-1,7-diphenyl-1,2,3,5,6,7-hexahydropyrido[3,2,1-ij]quinolin-9-ylcarbamate (829), (69 mg 52%). 1H NMR (300 MHz, Acetone-d6) ppm 1.72 (s, 6H) 1.89-2.03 (m, 2H) 2.17-2.30 (m, 2H) 2.73-2.88 (m, 2H) 2.92-3.03 (m, 2H) 3.56 (s, 3H) 7.05-7.33 (m, 12H) 8.02 (br. s., 1H).

Following a procedure similar to that for (829), gained (1R,7S)-1,7-dimethyl-1,7-diphenyl-1,2,3,5,6,7-hexahydropyrido[3,2,1-ij]quinolin-9-ylcarbamate (353), (130 g, 62% yield) from (10). 1H NMR (300 MHz, Acetone-d6) δ ppm 1.74 (s, 6H) 1.98-2.10 (m, 2H) 2.13-2.24 (m, 2H) 2.78-2.92 (m, 2H) 2.92-3.05 (m, 2H) 3.55 (s, 3H) 7.06 (s, 2H) 7.12-7.34 (m, 10H) 8.02 (br. s., 1H).

The following compounds were prepared according to the Reaction Scheme A and with the steps as shown in Example A above.

Ethyl 1,7-diphenyl-1,2,3,5,6,7-hexahydropyrido[3,2,1-ij]quinolin-9-ylcarbamate, 273

¹H NMR (300 MHz, CDCl₃) δ ppm 1.11 (t, J=7.03 Hz, 3H) 2.02-2.17 (m, 2H) 2.21-2.37 (m, 2H) 3.04-3.17 (m, 4H) 4.04 (q, 2H) 4.09-4.21 (m, 2H) 6.61 (br. s., 2H) 7.08-7.39 (m, 10H)

Isobutyl 1,7-diphenyl-1,2,3,5,6,7-hexahydropyrido[3,2,1-ij]quinolin-9-ylcarbamate, 274

¹H NMR (300 MHz, CDCl₃) δ ppm 0.94 (d, J=6.74 Hz, 6H) 1.84-2.02 (m, 1H) 2.02-2.17 (m, 2H) 2.20-2.37 (m, 2H) 3.31-3.22 (m, 4H) 4.19-4.14 (m, 2H) 6.63 (br. s., 2H) 7.11-7.24 (m, 5H) 7.25-7.37 (m, 5H)

Propyl 1,7-diphenyl-1,2,3,5,6,7-hexahydropyrido[3,2,1-ij]quinolin-9-ylcarbamate, 275

¹H NMR (300 MHz, CDCl₃) δ ppm 0.85 (t, J=6.89 Hz, 3H) 1.46-1.64 (m, 2H) 2.00-2.18 (m, 2H) 2.21-2.37 (m, 2H) 3.03-3.19 (m, 4H) 3.88-4.00 (m, 2H) 4.09-4.23 (m, 2H) 6.61 (br. s., 2H) 7.07-7.37 (m, 10H)

Butyl 1,7-diphenyl-1,2,3,5,6,7-hexahydropyrido[3,2,1-ij]quinolin-9-ylcarbamate, 276

¹H NMR (300 MHz, CDCl₃) δ ppm 0.87 (t, J=7.0 Hz, 3H) 1.30 (br. s., 2H) 1.42-1.56 (m, 2H) 2.02-2.17 (m, 2H) 2.19-2.39 (m, 2H) 3.03-3.17 (m, 4H) 3.91-4.03 (m, 2H) 4.10-4.22 (m, 2H) 6.61 (br. s., 2H) 7.08-7.38 (m, 10H)

Phenyl 1,7-diphenyl-1,2,3,5,6,7-hexahydropyrido[3,2,1-ij]quinolin-9-ylcarbamate, 277

¹H NMR (300 MHz, CDCl₃) δ ppm 2.05-2.19 (m, 2H) 2.21-2.40 (m, 2H) 3.04-3.20 (m, 4H), 4.11-4.24 (m, 2H) 6.71 (br. s., 2H) 6.99-7.44 (m, 15H)

Benzyl 1,7-diphenyl-1,2,3,5,6,7-hexahydropyrido[3,2,1-ij]quinolin-9-ylcarbamate, 278

¹H NMR (300 MHz, CDCl₃) δ ppm 1.91-2.09 (m, 2H) 2.10-2.29 (m, 2H) 2.93-3.13 (m, 4H) 4.01-4.15 (m, 2H) 4.92 (s, 2H) 6.56 (br. s., 2H) 7.01-7.32 (m, 15H)

Propyl 1,7-bis(3-fluorophenyl)-1,2,3,5,6,7-hexahydropyrido[3,2,1-ij]quinolin-9-ylcarbamate, 094

1H NMR (300 MHz, CD₃OD) δ ppm 0.89 (t, 7.0 Hz, H) 1.47-1.67 (m, 2H) 1.99-2.14 (m, 2H) 2.19-2.37 (m, 2H) 3.08 (t, J=5.71 Hz, 4H) 3.91 (t, J=6.74 Hz, 2H) 4.17 (t, J=6.01 Hz, 2H) 6.67 (br. s., 2H) 6.81-7.04 (m, 6H) 7.22-7.38 (m, 2H)

Ethyl 1,7-bis(3-fluorophenyl)-1,2,3,5,6,7-hexahydropyrido[3,2,1-ij]quinolin-9-ylcarbamate, 093

1H NMR (300 MHz, CD₃OD) δ ppm 1.15 (t, 7.0 Hz, H) 1.98-2.16 (m, 2H) 2.18-2.37 (m, 2H) 2.96-3.18 (m, 4H) 4.00 (q, J=7.13 Hz, 2H) 4.19 (t, J=5.86 Hz, 2H) 6.68 (br. s., 2H) 6.77-7.01 (m, 6H) 7.20-7.35 (m, 2H)

Butyl 1,7-bis(3-fluorophenyl)-1,2,3,5,6,7-hexahydropyrido[3,2,1-ij]quinolin-9-ylcarbamate, 202

1H NMR (300 MHz, Acetone-d₆) δ ppm 0.86 (t, 7.0 Hz, 6H) 1.20-1.39 (m, 2H) 2.06-2.15 (m, 2H) 2.21-2.39 (m, 2H) 3.02-3.17 (m, 4H) 3.94 (t, J=6.59 Hz, 2H) 4.22 (t, J=5.86 Hz, 2H) 6.83 (br. s., 2H) 6.88-7.09 (m, 6H) 7.28-7.42 (m, 2H)

Methyl 1,7-bis(3-fluorophenyl)-1,2,3,5,6,7-hexahydropyrido[3,2,1-ij]quinolin-9-ylcarbamate, 779

1H NMR (300 MHz, CD₃OD) δ ppm 2.01-2.15 (m, 2H) 2.21-2.37 (m, 2H) 3.09 (t, J=5.71 Hz, 4H) 3.57 (s, 3H) 4.18 (t, J=6.15 Hz, 2H) 6.67 (s, 2H) 6.81-7.03 (m, 6H) 7.25-7.38 (m, 2H)

2-fluoroethyl 1,7-diphenyl-1,2,3,5,6,7-hexahydropyrido[3,2,1-ij]quinolin-9-ylcarbamate, 095

1H NMR (300 MHz, CD₃OD) δ ppm 1.99-2.16 (m, 2H) 2.19-2.36 (m, 2H) 3.00-3.16 (m, 4H) 4.09-4.27 (m, 4H) 4.29-4.36 (m, 1H) 4.46-4.52 (m, 1H) 6.66 (br. s., 2H) 7.07-7.21 (m, 6H) 7.21-7.33 (m, 4H)

But-3-enyl 1,7-diphenyl-1,2,3,5,6,7-hexahydropyrido[3,2,1-ij]quinolin-9-ylcarbamate, 354

1H NMR (300 MHz, Acetone-d₆) δ ppm 2.04-2.15 (m, 2H) 2.18-2.41 (m, 4H) 3.02-3.18 (m, 4H) 3.89-4.01 (m, 2H) 4.90-5.14 (m, 2H) 5.69-5.88 (m, 1H) 6.78 (br. s., 2H) 7.08-7.25 (m, 6H) 7.23-7.38 (m, 4H)

But-2-ynyl 1,7-diphenyl-1,2,3,5,6,7-hexahydropyrido[3,2,1-ij]quinolin-9-ylcarbamate, 353

1H NMR (300 MHz, Acetone-d₆) δ ppm 1.74 (s, 3H) 2.06-2.13 (m, 2H) 2.19-2.34 (m, 2H) 3.02-3.20 (m, 4H) 4.19 (t, J=6.01 Hz, 2H) 4.52 (q, J=2.54 Hz, 2H) 6.78 (s, 2H) 7.12-7.24 (m, 6H) 7.26-7.35 (m, 4H)

Prop-2-ynyl 1,7-diphenyl-1,2,3,5,6,7-hexahydropyrido[3,2,1-ij]quinolin-9-ylcarbamate, 352

1H NMR (300 MHz, Acetone-d₆) δ ppm 2.05-2.15 (m, 2H) 2.20-2.36 (m, 2H) 2.90 (t, J=2.49 Hz, 1H) 3.00-3.20 (m, 4H) 4.19 (t, J=6.01 Hz, 2H) 4.59 (d, J=2.34 Hz, 2H) 6.78 (s, 2H) 7.11-7.24 (m, 6H) 7.25-7.37 (m, 4H)

4-chlorobutyl 1,7-diphenyl-1,2,3,5,6,7-hexahydropyrido[3,2,1-ij]quinolin-9-ylcarbamate, 206

1H NMR (300 MHz, Acetone-d₆) δ ppm 1.66-1.96 (m, 4H) 2.06-2.11 (m, 2H) 2.22-2.32 (m, 2H) 3.04-3.17 (m, 4H) 3.58 (t, J=6 Hz, 2H) 3.96 (t, J=6.3 Hz, 2H) 4.19 (t, J=6.3 Hz, 2H) 6.77 (s, 2H) 7.16-7.20 (m, 6H) 7.22-7.33 (m, 4H)

3-chloropropyl 1,7-diphenyl-1,2,3,5,6,7-hexahydropyrido[3,2,1-ij]quinolin-9-ylcarbamate, 205

1H NMR (300 MHz, CD₃OD) δ ppm 1.91-2.14 (m, 4H) 2.20-2.34 (m, 2H) 3.02-3.15 (m, 4H) 4.07 (t, J=6.01 Hz, 2H) 4.11-4.21 (m, 2H) 6.64 (br. s., 2H) 7.09-7.21 (m, 6H) 7.23-7.31 (m, 4H)

Ethyl (1S,7S)-1,7-dimethyl-1,7-diphenyl-1,2,3,5,6,7-hexahydropyrido[3,2,1-ij]quinolin-9-ylcarbamate, 941

1H NMR (300 MHz, Acetone-d6) δ ppm 1.16 (t, J=7.18 Hz, 3H) 1.74 (s, 6H) 1.90-2.01 (m, 2H) 2.16-2.32 (m, 2H)

2.73-2.89 (m, 2H) 2.90-3.03 (m, 2H) 4.02 (q, J=7.13 Hz, 2H) 7.06-7.32 (m, 12H) 8.02 (br. s., 1H)

Propyl (1S,7S)-1,7-dimethyl-1,7-diphenyl-1,2,3,5,6,7-hexahydropyrido[3,2,1-ij]quinolin-9-ylcarbamate, 942

1H NMR (300 MHz, Acetone-d6) δ ppm 0.88 (t, J=7.33 Hz, 3H) 1.46-1.65 (m, 2H) 1.72 (s, 6H) 1.88-2.03 (m, 2H) 2.18-2.32 (m, 2H) 2.70-2.88 (m, 2H) 2.89-3.03 (m, 2H) 3.94 (t, J=6.59 Hz, 2H) 7.06-7.33 (m, 12H) 8.02 (br. s., 1H)

Butyl (1S,7S)-1,7-dimethyl-1,7-diphenyl-1,2,3,5,6,7-hexahydropyrido[3,2,1-ij]quinolin-9-ylcarbamate, 943

1H NMR (300 MHz, Acetone-d6) δ ppm 0.88 (t, J=7.33 Hz, 3H) 1.27-1.42 (m, 1H) 1.45-1.61 (m, 1H) 1.67-1.77 (s, 6H) 1.88-2.03 (m, 2H) 2.18-2.31 (m, 2H) 2.72-2.89 (m, 4H) 2.90-3.02 (m, 2H) 3.93-4.05 (m, 2H) 7.06-7.32 (m, 12H) 8.01 (br. s., 1H)

2-fluoroethyl (1S,7S)-1,7-dimethyl-1,7-diphenyl-1,2,3,5,6,7-hexahydropyrido[3,2,1-ij]quinolin-9-ylcarbamate, 944

1H NMR (300 MHz, Acetone-d6) δ ppm 1.73 (s, 6H) 1.91-2.02 (m, 2H) 2.19-2.32 (m, 2H) 2.73-2.85 (m, 2H) 2.88-3.04 (m, 2H) 4.16-4.26 (m, 1H) 4.25-4.36 (m, 1H) 4.44-4.55 (m, 1H) 4.60-4.68 (m, 1H) 7.09-7.31 (m, 12H) 8.20 (br. s., 1H)

3-chloropropyl (1S,7S)-1,7-dimethyl-1,7-diphenyl-1,2,3,5,6,7-hexahydropyrido[3,2,1-ij]quinolin-9-ylcarbamate, 945

1H NMR (300 MHz, Acetone-d6) δ ppm 1.73 (s, 6H) 1.89-2.03 (m, 2H) 2.18-2.33 (m, 2H) 2.18-2.31 (m, 2H) 2.75-2.88 (m, 2H) 2.90-3.03 (m, 2H) 3.58-3.70 (m, 2H) 4.08-4.19 (m, 2H) 7.03-7.32 (m, 12H) 8.11 (br. s., 1H)

Ethyl (1R,7S)-1,7-dimethyl-1,7-diphenyl-1,2,3,5,6,7-hexahydropyrido[3,2,1-ij]quinolin-9-ylcarbamate, 354

1H NMR (300 MHz, Acetone-d6) δ ppm 1.15 (t, J=7.03 Hz, 3H) 1.74 (s, 6H) 1.97-2.11 (m, 2H) 2.11-2.24 (m, 2H) 2.73-2.91 (m, 2H) 2.92-3.03 (m, 2H) 3.94-4.08 (m, 2H) 7.08 (br. s., 2H) 7.12-7.35 (m, 10H) 7.98 (br. s., 1H)

Propyl (1R,7S)-1,7-dimethyl-1,7-diphenyl-1,2,3,5,6,7-hexahydropyrido[3,2,1-ij]quinolin-9-ylcarbamate, 355

1H NMR (300 MHz, Acetone-d6) δ ppm 0.87 (t, J=7.33 Hz, 3H) 1.46-1.62 (m, 2H) 1.74 (s, 6H) 1.98-2.09 (m, 2H) 2.10-2.23 (m, 2H) 2.82-2.91 (m, 2H) 2.91-3.06 (m, 2H) 3.87-3.98 (m, 2H) 7.08 (s, 2H) 7.14-7.35 (m, 10H) 8.01 (br. s., 1H)

Butyl (1R,7S)-1,7-dimethyl-1,7-diphenyl-1,2,3,5,6,7-hexahydropyrido[3,2,1-ij]quinolin-9-ylcarbamate, 356

1H NMR (300 MHz, Acetone-d6) δ ppm 0.88 (t, J=7.33 Hz, 3H) 1.24-1.41 (m, 2H) 1.47-1.60 (m, 2H) 1.74 (s, 6H) 1.97-2.11 (m, 2H) 2.08-2.24 (m, 2H) 2.78-2.90 (m, 2H) 2.89-3.04 (m, 2H) 3.91-4.01 (m, 2H) 7.09 (br. s., 2H) 7.13-7.34 (m, 10H) 8.00 (br. s., 1H)

3-chloropropyl (1R,7S)-1,7-dimethyl-1,7-diphenyl-1,2,3,5,6,7-hexahydropyrido[3,2,1-ij]quinolin-9-ylcarbamate, 357

1H NMR (300 MHz, Acetone-d6) δ ppm 1.74 (s, 6H) 1.97-2.09 (m, 2H) 2.11-2.25 (m, 2H) 2.79-2.93 (m, 4H) 2.91-3.04 (m, 2H) 3.56-3.72 (m, 2H) 4.05-4.18 (m, 2H) 7.07 (br. s., 2H) 7.10-7.34 (m, 10H) 8.08 (s, 1H)

But-3-enyl (1R,7S)-1,7-dimethyl-1,7-diphenyl-1,2,3,5,6,7-hexahydropyrido[3,2,1-ij]quinolin-9-ylcarbamate, 358

1H NMR (300 MHz, Acetone-d6) δ ppm 1.74 (s, 6H) 1.93-2.12 (m, 2H) 2.11-2.23 (m, 2H) 2.23-2.37 (m, 2H) 2.81-2.90 (m, 2H) 2.91-3.06 (m, 2H) 4.02 (t, J=6.74 Hz, 2H) 4.91-5.14 (m, 2H) 5.68-5.87 (m, 1H) 7.09 (br. s., 2H) 7.12-7.35 (m, 10H) 8.03 (br. s., 1H)

methyl (1S,7S)-1,7-bis(4-fluorophenyl)-1,7-dimethyl-1,2,3,5,6,7-hexahydropyrido[3,2,1-ij]quinolin-9-ylcarbamate, 674

¹H NMR (300 MHz, Acetone-d6): δ=1.71 (s, 6H) 1.92-2.07 (m, 2H) 2.19-2.27 (m, 2H) 2.76-2.84 (m, 2H) 2.95-3.02 (m, 2H) 3.57 (s, 3H) 6.98-7.22 (m, 10H)

butyl (1S,7S)-1,7-bis(4-fluorophenyl)-1,7-dimethyl-1,2,3,5,6,7-hexahydropyrido[3,2,1-ij]quinolin-9-ylcarbamate, 672

¹H NMR (300 MHz, Acetone-d6): δ=0.88 (t, J=7.5 Hz, 3H) 1.51-1.56 (m, 2H) 1.33-1.38 (m, 2H) 1.73 (s, 6H) 1.92-2.06 (m, 2H) 2.21-2.27 (m, 2H) 2.81-2.84 (m, 2H) 2.94-3.27 (m, 2H) 3.97-4.43 (m, 2H) 6.98-7.22 (m, 10H)

S-methyl (1S,7S)-1,7-dimethyl-1,7-diphenyl-1,2,3,5,6,7-hexahydropyrido[3,2,1-ij]quinolin-9-ylcarbamothioate, 583

¹H NMR (300 MHz, Acetone-d6): δ=1.68 (s, 6H) 2.02 (s, 3H) 2.20-1.88 (m, 4H) 2.95-3.01 (m, 2H) 2.80-2.95 (m, 2H) 6.76 (s, 2H) 7.33-7.17 (m, 10H)

S-propyl (1S,7S)-1,7-dimethyl-1,7-diphenyl-1,2,3,5,6,7-hexahydropyrido[3,2,1-ij]quinolin-9-ylcarbamothioate, 585

¹H NMR (300 MHz, Acetone-d6): δ=0.91 (t, J=7.2 Hz, 3H), 0.97-1.1 (m, 2H) 1.49-1.51 (m, 4H) 1.74 (s, 6H) 1.92-1.96 (m, 2H) 2.18-2.23 (m, 2H) 2.73-2.84 (m, 4H) 2.95-3.05 (m, 2H) 7.05 (s, 2H) 7.15-7.36 (m, 8H)

S-methyl (1R,7S)-1,7-dimethyl-1,7-diphenyl-1,2,3,5,6,7-hexahydropyrido[3,2,1-ij]quinolin-9-ylcarbamothioate, 582

¹H NMR (300 MHz, Acetone-d6): δ=1.73 (s, 6H) 2.20 (s, 3H) 1.98-2.07 (m, 2H) 2.14-2.17 (m, 2H) 2.80-2.88 (m, 2H) 2.95-3.01 (m, 2H) 7.13-7.32 (m, 12H)

S-propyl (1R,7S)-1,7-dimethyl-1,7-diphenyl-1,2,3,5,
6,7-hexahydropyrido[3,2,1-ij]quinolin-9-ylcarbam-
othioate, 584

$^1$H NMR (300 MHz, Acetone-d6): δ=1.40 (t, J=9 Hz, 3H) 2.05-2.12 (m, 2H) 2.28 (s, 6H) 2.66-2.72 (m, 6H) 2.51-2.64 (m, 2H) 3.47-3.54 (m, 2H) 3.31-3.39 (m, 2H) 7.59-7.80 (m, 12H)

S-methyl (1S,7S)-1,7-bis(4-fluorophenyl)-1,7-dim-
ethyl-1,2,3,5,6,7-hexahydropyrido[3,2,1-ij]quinolin-
9-ylcarbamothioate, 671

$^1$H NMR (300 MHz, Acetone-d6): δ=1.73 (s, 6H) 2.19-2.21 (m, 2H) 2.24-2.27 (m, 2H) 2.81 (s, 3H) 2.76-2.86 (m, 2H) 2.96-3.03 (m, 2H) 6.93-7.22 (m, 10H)

S-propyl (1S,7S)-1,7-bis(4-fluorophenyl)-1,7-dim-
ethyl-1,2,3,5,6,7-hexahydropyrido[3,2,1-ij]quinolin-
9-ylcarbamothioate, 673

$^1$H NMR (300 MHz, Acetone-d6): δ=0.92 (t, J=9 Hz, 3H) 1.08-2.11 (m, 2H) 1.50-1.60 (m, 4H) 1.70 (s, 6H) 1.90-1.98 (m, 1H) 2.17-2.25 (m, 3H) 2.73-2.78 (m, 1H) 2.93-3.00 (m, 1H) 6.96-7.19 (m, 10H)

Example B

Method B1: Preparation of 1-(1,7-diphenyl-1,2,3,5,6,
7-hexahydropyrido[3,2,1-ij]quinolin-9-yl)-3-ethy-
lurea (484)

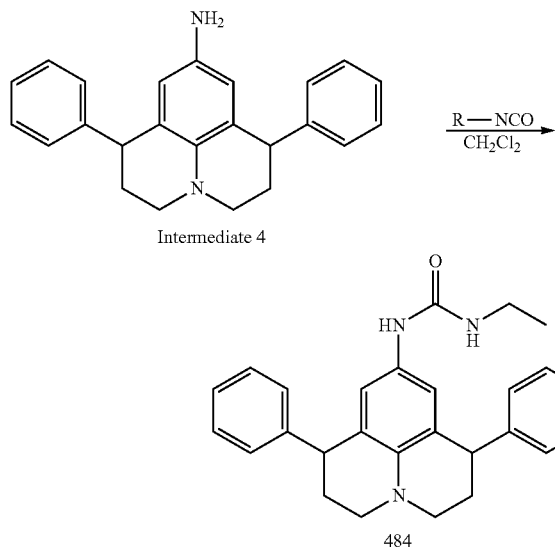

To a solution 1,7-diphenyl-1,2,3,5,6,7-hexahydropyrido [3,2,1-ij]quinolin-9-amine (Intermediate 4), (102 mg, 0.30 mmol) in dichloromethane (15 mL) was added ethyl isocyanate (0.026 mL, 0.33 mmol), mmol) under argon at 0° C. The reaction mixture was then stirred at room temperature for overnight. The solvent was removed under reduced pressure and purified by MPLC (medium pressure liquid chromatography) using silica gel column with 15 to 20% EtOAc:Hexane to get 1-(1,7-diphenyl-1,2,3,5,6,7-hexahydropyrido[3,2,1-ij] quinolin-9-yl)-3-ethylurea (484) (120 mg 97%). $^1$H NMR (300 MHz, CDCl$_3$) δ ppm 0.91 (t, J=7.18 Hz, 3H) 2.05-2.20 (m, 2H) 2.21-2.39 (m, 2H) 2.96-3.28 (m, 6H) 4.07-4.19 (m, 2H) 4.35 (br. s., 1H) 5.58 (s, 1H) 6.43 (s, 2H) 7.06-7.36 (m, 10H)

Method B2: Preparation of 1-((1S,7S)-1,7-dimethyl-
1,7-diphenyl-1,2,3,5,6,7-hexahydropyrido[3,2,1-ij]
quinolin-9-yl)-3-ethylurea, 249

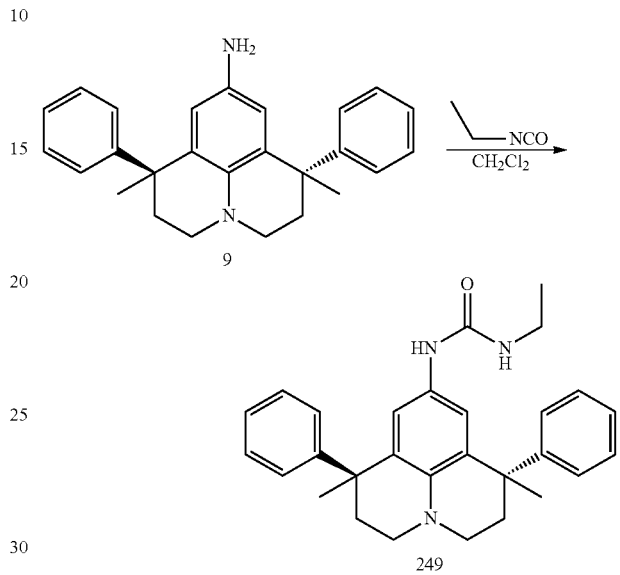

To a solution (1S,7S)-1,7-dimethyl-9-amino-1,7-diphenyl-1,2,3,5,6,7-hexahydropyrido[3,2,1-ij]quinoline (9), (110 mg, 0.30 mmol) in dichloromethane (15 mL) was added ethyl isocyanate (0.026 mL, 0.328 mmol), mmol) under argon at 0° C. The reaction mixture was then stirred at room temperature for overnight. The solvent was removed under reduced pressure and purified by MPLC) using silica gel column with 15 to 20% EtOAc:Hexane to get 1-((1S,7S)-1,7-dimethyl-1,7-diphenyl-1,2,3,5,6,7-hexahydropyrido[3,2,1-ij]quinolin-9-yl)-3-ethylurea (249), (96 mg 73%). 1H NMR (300 MHz, Acetone-d6) δ ppm 1.00 (t, J=7.18 Hz, 3H) 1.71 (s, 6H) 1.91-2.02 (m, 2H) 2.15-2.31 (m, 2H) 2.75-2.87 (m, 2H) 2.90-3.03 (m, 2H) 3.03-3.16 (m, 2H) 6.98 (s, 2H) 7.09-7.31 (m, 10H)

The following compounds were prepared according to the Reaction Scheme B and with the steps as shown in Example B above.

1-Butyl-3-(1,7-diphenyl-1,2,3,5,6,7-hexahydropy-
rido[3,2,1-ij]quinolin-9-yl)urea, 485

$^1$H NMR (300 MHz, CDCl$_3$) δ ppm 0.85 (t, J=7 Hz, 3H) 1.04-1.38 (m, 4H) 2.05-2.19 (m, 2H) 2.19-2.38 (m, 2H) 2.89-3.29 (m, 6H) 4.14 (t, J=6.15 Hz, 2H) 4.38 (br. s., 1H) 5.61 (s, 1H) 6.43 (s, 2H) 7.05-7.38 (m, 10H)

1-(1,7-diphenyl-1,2,3,5,6,7-hexahydropyrido[3,2,1-
ij]quinolin-9-yl)-3-pentylurea, 486

$^1$H NMR (300 MHz, CDCl$_3$) δ ppm 0.84 (t, J=7.18 Hz, 3H) 1.03-1.33 (m, 6H) 2.04-2.19 (m, 2H) 2.20-2.38 (m, 2H) 2.90-3.28 (m, 6H) 4.07-4.20 (m, 2H) 4.38 (br. s., 1H) 5.58 (s, 1H) 6.43 (s, 5H) 7.07-7.39 (m, 10H)

1-(1,7-diphenyl-1,2,3,5,6,7-hexahydropyrido[3,2,1-ij]quinolin-9-yl)-3-hexylurea, 487

$^1$H NMR (300 MHz, CDCl$_3$) δ ppm 0.86 (t, J=7.1 Hz 3H) 1.06-1.33 (m, 8H) 2.00-2.20 (m, 2H) 2.21-2.40 (m, 2H) 2.93-3.29 (m, 6H) 4.02-4.17 (m, 2H) 4.29-4.45 (m, 1H) 5.57 (br. s., 1H) 6.43 (br. s., 2H) 7.03-7.40 (m, 10H)

1-(2-chloroethyl)-3-(1,7-diphenyl-1,2,3,5,6,7-hexahydropyrido[3,2,1-ij]quinolin-9-yl)urea, 769

$^1$H NMR (300 MHz, CD$_3$OD) δ ppm 1.99-2.15 (m, 2H) 2.19-2.35 (m, 2H) 3.04-3.15 (m, 4H), 3.49 (m, 2H) 3.41-3.50 (m, 2H) 4.11-4.22 (m, 2H) 6.55 (s, 2H) 7.09-7.21 (m, 5H) 7.21-7.32 (m, 5H)

1-allyl-3-(1,7-diphenyl-1,2,3,5,6,7-hexahydropyrido[3,2,1-ij]quinolin-9-yl)urea, 773

$^1$H NMR (300 MHz, CD$_3$OD) δ ppm 2.00-2.14 (m, 2H) 2.20-2.36 (m, 2H) 3.04-3.16 (m, 4H) 3.58-3.69 (m, 2H) 4.11-4.23 (m, 2H) 4.94-5.13 (m, 1H) 5.73 (m, 1H) 6.56 (s, 2H) 7.09-7.21 (m, 5H) 7.23-7.31 (m, 5H)

1-tert-butyl-3-(1,7-diphenyl-1,2,3,5,6,7-hexahydropyrido[3,2,1-ij]quinolin-9-yl)urea, 148

$^1$H NMR (300 MHz, CDCl$_3$) δ ppm 7.12-7.33 (m, 10H) 6.41 (s, 2H) 4.14 (t, J=6 Hz, 2H) 3.14-3.19 (m, 4H) 2.25-2.30 (m, 2H) 2.10-2.17 (m, 2H) 2.25-2.33 (m, 2H)

1-(1,7-diphenyl-1,2,3,5,6,7-hexahydropyrido[3,2,1-ij]quinolin-9-yl)-3-(furan-3-ylmethyl)urea, 258

$^1$H NMR (300 MHz, CD$_3$OD) δ ppm 7.12-7.33 (m, 11H) 6.56 (s, 2H), 6.25-6.27 (m, 1H) 6.08-6.10 (m, 1H) 4.19 (s, 2H) 4.16 (t, J=6 Hz, 2H) 3.07-3.12 (m, 4H) 2.01-2.11 (m, 2H) 2.27-2.29 (m, 2H)

1-((1S,7S)-1,7-dimethyl-1,7-diphenyl-1,2,3,5,6,7-hexahydropyrido[3,2,1-ij]quinolin-9-yl)-3-propylurea, 250

$^1$H NMR (300 MHz, Acetone-d6) δ ppm 0.83 (t, J=6.8 Hz, 3H) 1.33-1.47 (m, 2H) 1.72 (s, 6H) 1.88-2.02 (m, 2H) 2.17-2.30 (m, 2H) 2.77-2.88 (m, 2H) 2.90-3.10 (m, 4H) 6.98 (s, 2H) 7.10-7.30 (m, 10H)

1-((1S,7S)-1,7-dimethyl-1,7-diphenyl-1,2,3,5,6,7-hexahydropyrido[3,2,1-ij]quinolin-9-yl)-3-butylurea, 251

$^1$H NMR (300 MHz, Acetone-d6) δ ppm 0.86 (t, J=6.8 Hz, 3H) 1.20-1.45 (m, 4H) 1.70 (s, 6H) 1.90-2.02 (m, 2H) 2.15-2.30 (m, 2H) 2.79-2.88 (m, 2H) 2.90-3.02 (m, 2H) 3.02-3.15 (m, 2H) 6.98 (s, 2H) 7.09-7.33 (m, 10H)

1-allyl-3-((1S,7S)-1,7-dimethyl-1,7-diphenyl-1,2,3,5,6,7-hexahydropyrido[3,2,1-ij]quinolin-9-yl)urea, 252

$^1$H NMR (300 MHz, Acetone-d6) δ ppm 1.73 (s, 6H) 1.87-2.02 (m, 2H) 2.16-2.30 (m, 2H) 2.74-2.87 (m, 2H) 2.89-3.01 (m, 2H) 3.67-3.78 (m, 2H) 4.91-5.16 (m, 2H) 5.73-5.90 (m, 1H) 7.00 (s, 2H) 7.06-7.35 (m, 10H)

1-t-butyl-3-((1S,7S)-1,7-dimethyl-1,7-diphenyl-1,2,3,5,6,7-hexahydropyrido[3,2,1-ij]quinolin-9-yl)urea, 581

$^1$H NMR (300 MHz, Acetone-d6): δ=0.71 (s, 9H) 1.20 (s, 6H) 1.97-2.02 (m, 2H) 2.07-2.16 (m, 2H) 2.74-2.80 (m, 2H) 2.93-2.97 (m, 2H) 6.79 (s, 2H) 7.36-7.17 (m, 10H)

1-((1R,7S)-1,7-dimethyl-1,7-diphenyl-1,2,3,5,6,7-hexahydropyrido[3,2,1-ij]quinolin-9-yl)-3-ethylurea, 463

$^1$H NMR (300 MHz, Acetone-d6) δ ppm 1.00 (t, J=7.18 Hz, 3H) 1.73 (s, 6H) 1.94-2.03 (m, 2H) 2.10-2.25 (m, 2H) 2.79-2.90 (m, 2H) 2.92-3.04 (m, 2H) 3.10 (t, J=6.45 Hz, 2H) 5.29 (br. s., 1H) 6.93 (s, 2H) 7.07-7.34 (m, 10H)

1-((1R,7S)-1,7-dimethyl-1,7-diphenyl-1,2,3,5,6,7-hexahydropyrido[3,2,1-ij]quinolin-9-yl)-3-propylurea, 464

$^1$H NMR (300 MHz, Acetone-d6) δ ppm 0.82 (t, J=7.00 Hz, 3H) 1.31-1.48 (m, 2H) 1.75 (s, 6H) 1.95-2.03 (m, 2H) 2.10-2.24 (m, 2H) 2.75-2.89 (m, 4H) 2.92-3.07 (m, 2H) 5.33-5.35 (m, 1H) 6.95 (s, 2H) 7.07-7.35 (m, 10H)

1-((1R,7S)-1,7-dimethyl-1,7-diphenyl-1,2,3,5,6,7-hexahydropyrido[3,2,1-ij]quinolin-9-yl)-3-butylurea, 465

$^1$H NMR (300 MHz, Acetone-d6) δ ppm 0.86 (t, J=7.18 Hz, 3H) 1.19-1.44 (m, 4H) 1.73 (s, 6H) 1.94-2.05 (m, 2H) 2.11-2.23 (m, 2H) 2.77-2.92 (m, 4H) 2.92-3.02 (m, 2H) 3.02-3.12 (m, 2H) 5.31 (br. s., 1H) 7.09-7.34 (m, 10H)

1-t-butyl-3-((1R,7S)-1,7-dimethyl-1,7-diphenyl-1,2,3,5,6,7-hexahydropyrido[3,2,1-ij]quinolin-9-yl)urea, 580

$^1$H NMR (300 MHz, Acetone-d6): δ=1.26 (s, 9H) 1.71 (s, 6H) 1.57-1.71 (m, 2H) 1.43-1.47 (m, 2H) 2.44-2.49 (m, 2H) 2.24-2.30 (m, 2H) 6.30 (s, 2H) 6.64-6.84 (m, 10H)

Example C

Method C: Preparation of 3-(1,7-diphenyl-1,2,3,5,6,7-hexahydropyrido[3,2,1-ij]quinolin-9-yl)-1,1-dimethylurea (405)

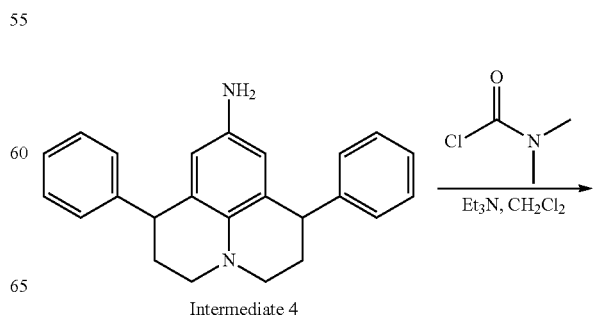

Intermediate 4

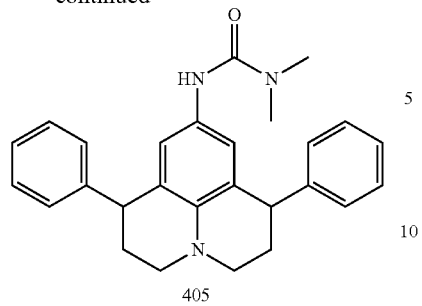

405

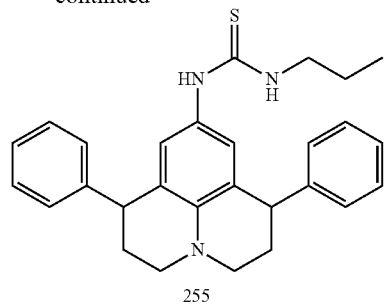

255

To a solution 1,7-diphenyl-1,2,3,5,6,7-hexahydropyrido[3,2,1-ij]quinolin-9-amine (Intermediate 4), (106 mg, 0.31 mmol) in dichloromethane (10 mL) was added triethyl amine (0.130 mL, 0.933 mmol) followed by dimethylcarbamic chloride (0.043 mL, 0.46 mmol), under argon at 0° C. The reaction mixture was then stirred at room temperature for overnight. The mixture was quenched with water (30 mL). The residue was isolated in a typical aqueous workup and purified by MPLC (medium pressure liquid chromatography) using silica gel column with 10 to 15% EtOAc:Hexane to give 3-(1,7-diphenyl-1,2,3,5,6,7-hexahydropyrido[3,2,1-ij]quinolin-9-yl)-1,1-dimethylurea, (405), (63 mg 49%). $^1$H NMR (300 MHz, CDCl$_3$) ppm 2.01-2.16 (m, 2H) 2.20-2.37 (m, 2H) 2.85 (s, 6H) 3.00-3.15 (m, 4H) 4.12-4.25 (m, 2H) 5.78 (s, 1H) 6.62 (s, 2H) 7.10-7.22 (m, 5H) 7.23-7.34 (m, 5H)

The following compound was prepared according to the Reaction Scheme C and with the steps as shown in Example C above.

N-(1,7-diphenyl-1,2,3,5,6,7-hexahydropyrido[3,2,1-ij]quinolin-9-yl)morpholine-4-carboxamide, 983

$^1$H NMR (300 MHz, CDCl$_3$) δ ppm 2.03-2.17 (m, 2H) 2.20-2.38 (m, 2H) 2.92-3.42 (m, 8H) 3.53-3.65 (m, 4H) 3.98-4.20 (m, 2H) 6.52-6.72 (m, 2H) 7.08-7.23 (m, 5H) 7.24-7.37 (m, 5H)

Example D

Method D: Preparation of 1-(1,7-diphenyl-1,2,3,5,6,7-hexahydropyrido[3,2,1-ij]quinolin-9-yl)-3-propylthiourea (255)

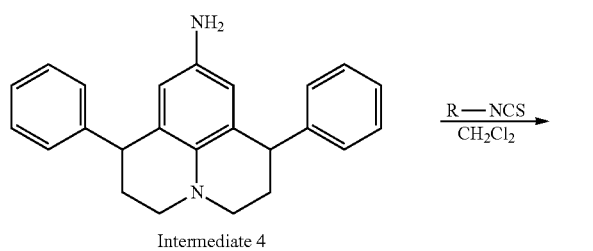

Intermediate 4

To a solution 1,7-diphenyl-1,2,3,5,6,7-hexahydropyrido[3,2,1-ij]quinolin-9-amine (Intermediate 4), (100 mg, 0.294 mmol) in dichloromethane (15 mL) was added propyl isothiocyanate (0.038 mL, 0.323 mmol) under argon at 0° C. The reaction mixture was then stirred at room temperature for overnight. The solvent was removed under reduced pressure and purified by MPLC (medium pressure liquid chromatography) using silica gel column with 15 to 20% EtOAc:Hexane to get 1-(1,7-diphenyl-1,2,3,5,6,7-hexahydropyrido[3,2,1-ij]quinolin-9-yl)-3-propylthiourea (255) (64 mg 49%). $^1$H NMR (300 MHz, CDCl$_3$) ppm 7.08-7.34 (m, 10H) 6.39 (s, 2H) 4.11 (t, J=6 Hz, 2H) 3.32-3.46 (m, 2H) 3.16-3.23 (m, 4H) 2.25-2.30 (m, 2H) 2.13-2.17 (m, 2H) 1.32-1.39 (m, 2H, 0.73 (t, J=6 Hz, 3H)

The following compound was prepared according to the Reaction Scheme D and with the steps as shown in Example D above.

1-(1,7-diphenyl-1,2,3,5,6,7-hexahydropyrido[3,2,1-ij]quinolin-9-yl)-3-hexylthiourea, 256

$^1$H NMR (300 MHz, CDCl$_3$) δ ppm 7.07-7.34 (m, 10H) 6.39 (s, 2H) 4.11 (t, J=6 Hz, 2H), 3.46-3.49 (m, 2H) 3.15-3.25 (m, 4H) 2.25-2.32 (m, 2H) 2.11-2.18 (m, 2H) 1.17-1.31 (m, 8H) 0.87 (t, J=6 Hz, 3H)

Example E

Method E: Preparation of N-butyl-1,7-diphenyl-1,2,3,5,6,7-hexahydropyrido[3,2,1-ij]quinoline-9-carboxamide (481)

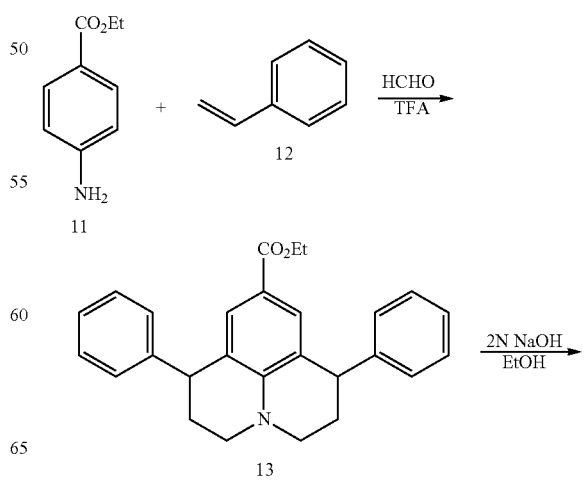

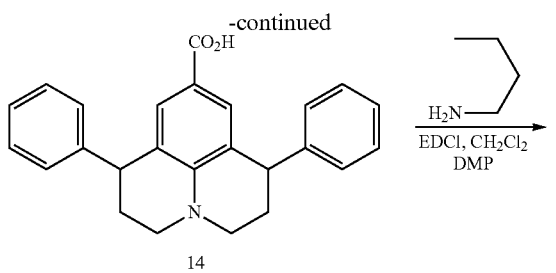

To a solution ethyl 4-aminobenzoate (11) (2.47 g, 15 mmol) in acetonitrile (10 mL) was added one equivalent of trifluoroacetic acid (1.71 g, 15 mmol). To this suspension was added with stirring a heterogeneous mixture of styrene (12), (8.6 mL, 75 mmol) and 37% formaldehyde solution (6.09 mL, 75 mmol) under argon gave yellow precipitate. The precipitate had failed to redissolve after 30 min. of stirring at room temperature, so the mixture was heated at reflux under argon for further 30 min, during which time the precipitate redissolved. The reaction mixture was cooled to room temperature. The residue was isolated in a typical aqueous workup and purified by MPLC (medium pressure liquid chromatography) using silica gel column with 10 to 15% EtOAc: Hexane to give ethyl 1,7-diphenyl-1,2,3,5,6,7-hexahydropyrido[3,2,1-ij]quinoline-9-carboxylate (13), (4.1 g 68%).

A solution of ethyl 1,7-diphenyl-1,2,3,5,6,7-hexahydropyrido[3,2,1-ij]quinoline-9-carboxylate (13), (4 g, 10 mmol), in EtOH (40 mL) was subjected to saponification reaction using 2N NaOH (40 mL). The residue was isolated in a typical aqueous workup and purified by MPLC (medium pressure liquid chromatography) using silica gel column with 30 to 40% EtOAc:Hexane to give 1,7-diphenyl-1,2,3,5,6,7-hexahydropyrido[3,2,1-ij]quinoline-9-carboxylic acid (14), (2 g 54%).

To a solution of 1,7-diphenyl-1,2,3,5,6,7-hexahydropyrido[3,2,1-ij]quinoline-9-carboxylic acid (14), (189 mg, 0.512 mmol) in dichloromethane (10 mL) were added butyl amine (0.027 mL, 0.512 mmol), EDCl (196 mg, 1.02 mmol), followed DMAP (4-(Dimethylamino)pyridine) (70 mg, 1.02 mmol) under argon at 0° C. The reaction mixture was then stirred at room temperature for overnight. The reaction was quenched with water (30 mL). The residue was isolated in a typical aqueous workup and purified by MPLC (medium pressure liquid chromatography) using silica gel column with 25 to 30% EtOAc:Hexane to give N-butyl-1,7-diphenyl-1,2,3,5,6,7-hexahydropyrido[3,2,1-ij]quinoline-9-carboxamide (481), (113 mg 52%). $^1$H NMR (300 MHz, CDCl$_3$) ppm 1H NMR (300 MHz, Solvent) ppm 0.87 (t, J=6.0 Hz, 3H) 1.17-1.38 (m, 2H) 1.36-1.52 (m, 2H) 2.03-2.17 (m, 2H) 2.18-2.36 (m, 2H) 3.06-3.37 (m, 6H) 4.21 (t, J=5.27 Hz, 2H) 5.61-5.75 (m, 1H) 7.03-7.16 (m, 4H) 7.17-7.37 (m, 8H).

The following compounds were prepared according to the Reaction Scheme E and with the steps as shown in Example E above.

N-methyl-1,7-diphenyl-1,2,3,5,6,7-hexahydropyrido[3,2,1-ij]quinoline-9-carboxamide, 775

$^1$H NMR (300 MHz, CDCl$_3$) δ ppm 2.05-2.19 (m, 2H) 2.18-2.35 (m, 2H) 2.79 (d, J=4.40 Hz, 3H) 3.08-3.27 (m, 4H) 4.15-4.25 (m, 2H) 5.78 (bs, 1H) 7.05-7.16 (m, 4H) 7.16-7.26 (m, 2H) 7.25-7.35 (m, 6H)

1,7-diphenyl-N-propyl-1,2,3,5,6,7-hexahydropyrido[3,2,1-ij]quinoline-9-carboxamide, 409

$^1$H NMR (300 MHz, CDCl$_3$) δ ppm 0.86 (t, J=7.47 Hz, 3H) 1.41-1.54 (m, 2H) 2.02-2.16 (m, 2H) 2.15-2.34 (m, 2H) 3.06-3.30 (m, 6H) 4.20 (q, J=5.66 Hz, 2H) 5.71 (br. s., 1H) 7.03-7.16 (m, 4H) 7.16-7.38 (m, 8H)

N-pentyl-1,7-diphenyl-1,2,3,5,6,7-hexahydropyrido[3,2,1-ij]quinoline-9-carboxamide, 482

$^1$H NMR (300 MHz, CDCl$_3$) δ ppm 0.85 (t, J=6.89 Hz, 3H) 1.16-1.34 (m, 4H) 1.37-1.52 (m, 2H) 2.04-2.17 (m, 2H) 2.17-2.35 (m, 2H) 3.07-3.35 (m, 6H) 4.20 (q, J=5.96 Hz, 2H) 5.69 (br. s., 1H) 7.06-7.16 (m, 4H) 7.17-7.39 (m, 8H)

N-(2-hydroxyethyl)-1,7-diphenyl-1,2,3,5,6,7-hexahydropyrido[3,2,1-ij]quinoline-9-carboxamide, 777

$^1$H NMR (300 MHz, CD$_3$OD) δ ppm 2.03-2.16 (m, 2H) 2.18-2.33 (m, 2H) 3.06-3.26 (m, 4H) 3.31-3.39 (m, 2H) 3.50-3.60 (m, 2H) 4.25 (t, J=5.13 Hz, 2H) 7.06-7.36 (m, 21H)

N-ethyl-1,7-bis(3-fluorophenyl)-1,2,3,5,6,7-hexahydropyrido[3,2,1-ij]quinoline-9-carboxamide, 611

$^1$H NMR (300 MHz, Acetone-d6) δ ppm 1.03 (t, J=7.18 Hz, 3H) 2.06-2.17 (m, 2H) 2.20-2.35 (m, 2H) 3.05-3.34 (m, 6H) 4.29 (t, J=5.13 Hz, 2H) 6.84-6.92 (m, 2H) 6.92-7.05 (m, 4H) 7.27-7.41 (m, 4H)

N-butyl-1,7-bis(3-fluorophenyl)-1,2,3,5,6,7-hexahydropyrido[3,2,1-ij]quinoline-9-carboxamide, 593

$^1$H NMR (300 MHz, Acetone-d6) δ ppm 0.87 (t, J=6.9 Hz, 3H) 1.30-1.37 (m, 2H) 1.44-1.51 (m, 2H) 2.09-2.17 (m, 2H) 2.18-2.35 (m, 2H) 3.20-3.27 (m, 6H) 4.25-4.29 (m, 2H) 6.97-7.02 (m, 4H) 7.30-7.38 (m, 6H).

Example F

Method F: Preparation of N-ethyl-2-(1,7-diphenyl-1,2,3,5,6,7-hexahydropyrido[3,2,1-ij]quinolin-9-yl)acetamide (371)

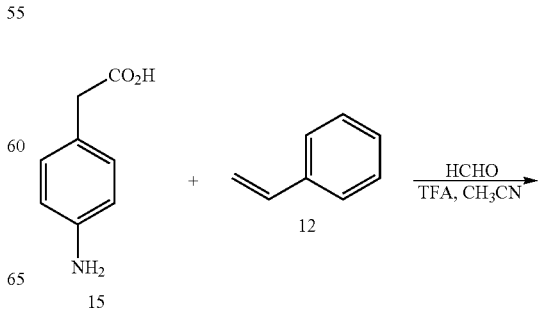

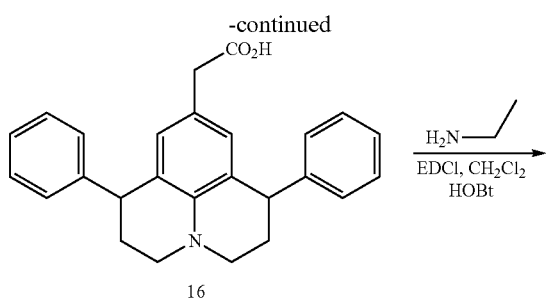

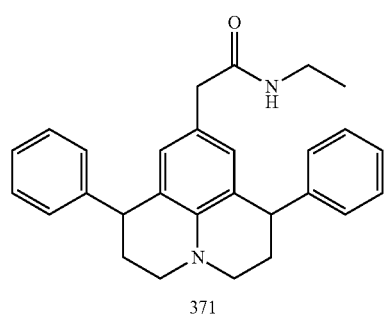

To a solution 2-(4-aminophenyl)acetic acid (15) (3.0 g, 19.84 mmol) in acetonitrile (10 mL) was added one equivalent of trifluoroacetic acid (1.53 ml, 19.84 mmol). To this suspension was added with stirring a heterogeneous mixture of styrene (12), (11.3 mL, 99.2 mmol) and 37% formaldehyde solution (9.0 mL, 99.2 mmol) under argon gave yellow precipitate. The precipitate had failed to redissolve after 30 min. of stirring at room temperature, so the mixture was heated at reflux under argon for further 30 min, during which time the precipitate redissolved. The reaction mixture was cooled to room temperature. The residue was isolated in a typical aqueous workup and purified by MPLC (medium pressure liquid chromatography) using silica gel column with 10 to 30% EtOAc:Hexane to give 2-(1,7-diphenyl-1,2,3,5,6,7-hexahydropyrido[3,2,1-ij]quinolin-9-yl)acetic acid (16), (1.9 g, 48%).

To a solution of 2-(1,7-diphenyl-1,2,3,5,6,7-hexahydropyrido[3,2,1-ij]quinolin-9-yl)acetic acid (16), (85 mg, 0.229 mmol) in dichloromethane (10 mL) were added Ethyl amine (0.015 mL, 0.229 mmol), EDCl (103 mg, 0.538 mmol), followed by HOBt (72 mg, 0.538 mmol) under argon at 0° C. The reaction mixture was then stirred at room temperature for overnight. The reaction was quenched with water (30 mL). The residue was isolated in a typical aqueous workup and purified by MPLC (medium pressure liquid chromatography) using silica gel column with 5% MeOH:CH$_2$Cl$_2$ to give N-ethyl-2-(1,7-diphenyl-1,2,3,5,6,7-hexahydropyrido[3,2,1-ij]quinolin-9-yl)acetamide (371), (27 mg, 29%).

$^1$H NMR (300 MHz, Acetone-d6) δ ppm 0.87 (t, J=6.9 Hz, 3H) 2.01-2.11 (m, 2H), 2.21-2.27 (m, 2H) 3.0-3.6 (m, 8H), 3.20-3.27 (m, 6H) 4.25-4.29 (m, 2H) 6.97-7.02 (m, 4H) 7.30-7.38 (m, 6H).

Example G

Method G: Procedure for the methyl (4R,10R)-4,10-diphenyl-4,5,6,8,9,10-hexahydropyrido[3,2,1-de][1,5]naphthyridin-2 ylcarbamate (179)

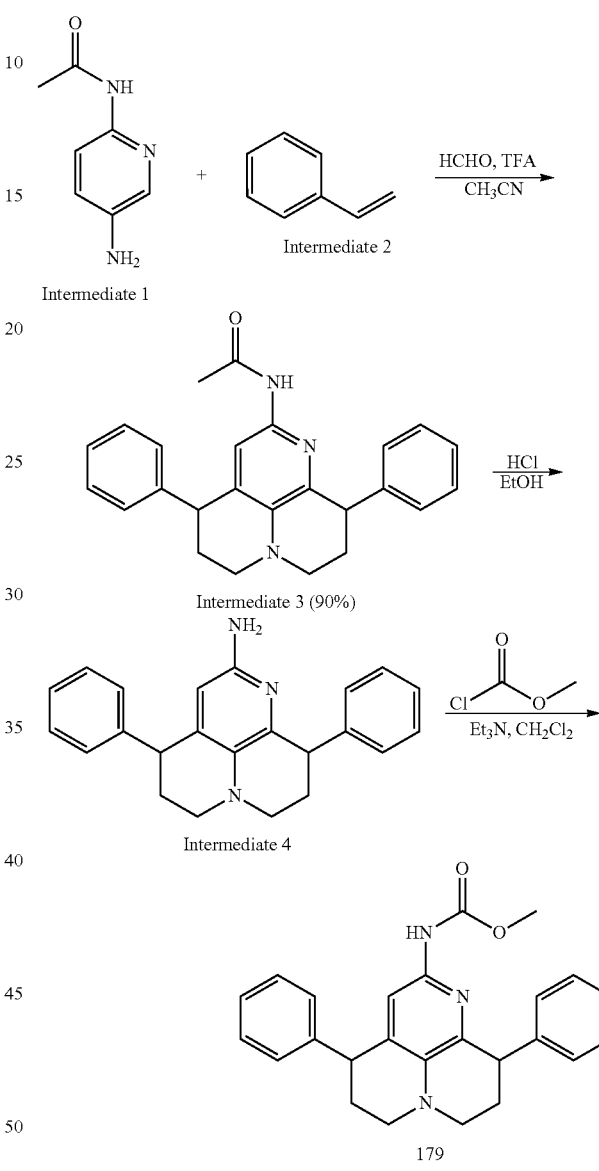

To a solution of N-(5-aminopyridin-2-yl)acetamide (Intermediate 1) (2.4 g, 15.8 mmol) in acetonitrile (12 mL) was added one equivalent of trifluoroacetic acid (1.2 mL, 15.8 mmol). To this suspension was added with stirring a heterogeneous mixture of styrene (Intermediate 2), (7.2 mL, 63.2 mmol) and 37% formaldehyde solution (5.2 mL, 63.2 mmol) under argon, which gave a yellow precipitate. The precipitate failed to redissolve after 30 min. of stirring at room temperature, so the mixture was heated at reflux under argon for further 30 min, during which time the precipitate redissolved. The reaction mixture was cooled to room temperature. The precipitate was filtered and wash with acetonitrile gave yellow solid, n-((4R,10R)-4,10-diphenyl-4,5,6,8,9,10-hexahydropyrido[3,2,1-de][1,5]naphthyridin-2-yl)acetamide, (Intermediate 3), (2.78 g).

A mixture of n-((4R,10R)-4,10-diphenyl-4,5,6,8,9,10-hexahydropyrido[3,2,1-de][1,5]naphthyridin-2-yl)acetamide, (Intermediate 3), (0.550 g, 1.43 mmol), in EtOH (12 mL) was Conc. HcL (1.2 mL). The mixture was stirred at 90° C. for two hrs. The mixture was concentrated, neutralized with aq. NaOH and extracted in $CH_2Cl_2$, dried ($MgSO_4$), filtered and concentrated gave (4R,10R)-4,10-diphenyl-4,5,6,8,9,10-hexahydropyrido[3,2,1-de][1,5]naphthyridin-2-amine (Intermediate 4) as a solid, (0.380 g).

To a solution (4R,10R)-4,10-diphenyl-4,5,6,8,9,10-hexahydropyrido[3,2,1-de][1,5]naphthyridin-2-amine (Intermediate 4), (110 mg, 0.322 mmol) in dichloromethane (10 mL) was added two equivalent of triethyl amine (0.090 mL, 0.644 mmol), followed by methyl chloroformate (0.037 mL, 0.483 mmol) under argon at 0° C. The reaction mixture was then stirred at room temperature for overnight. The mixture was quenched with water (30 mL). The residue was isolated in a typical aqueous workup and purified by MPLC (medium pressure liquid chromatography) using silica gel column with 10 to 15% EtOAc:Hexane to give methyl (4R,10R)-4,10-diphenyl-4,5,6,8,9,10-hexahydropyrido[3,2,1-de][1,5]naphthyridin-2-ylcarbamate, (179), (20 mg). $^1$H NMR (300 MHz, $CDCl_3$) δ ppm 2.00-2.18 (m, 2H) 2.22-2.39 (m, 2H) 3.03-3.22 (m, 4H) 3.50-3.64 (m, 3H) 3.54-3.65 (m, 3H) 4.05-4.23 (m, 2H) 6.61 (br. s., 2H) 7.08-7.38 (m, 10H)

Biological Data:

The compounds of the invention are assessed for their ability to activate or block activation of the human S1P3 receptor in T24 cells stably expressing the human S1P3 receptor using the method described in paragraph [0067] of United States Patent Application Publication No. 20070232682, which published on Oct. 4, 2007, which is hereby incorporated by reference in its entirety.

Ten thousands cells/well are plated into 384-well poly-D-lysine coated plates one day prior to use. The growth media for the S1P3 receptor expressing cell line is McCoy's 5A medium supplemented with 10% charcoal-treated fetal bovine serum (FBS), 1% antibiotic-antimycotic and 400 μg/ml geneticin. On the day of the experiment, the cells are washed twice with Hank's Balanced Salt Solution supplemented with 20 mM HEPES (HBSS/Hepes buffer). The cells are then dye loaded with 2 μM Fluo-4 diluted in the HBSS/Hepes buffer with 1.25 mM Probenecid and incubated at 37° C. for 40 minutes. Extracellular dye is removed by washing the cell plates four times prior to placing the plates in the FLIPR (Fluorometric Imaging Plate Reader, Molecular Devices). Ligands are diluted in HBSS/Hepes buffer and prepared in 384-well microplates. The positive control, Sphingosine-1-phosphate (S1P), is diluted in HBSS/Hepes buffer with 4 mg/ml fatty acid free bovine serum albumin. The FLIPR transfers 12.5 μl from the ligand microplate to the cell plate and takes fluorescent measurements for 75 seconds, taking readings every second, and then for 2.5 minutes, taking readings every 10 seconds. Compounds are tested over the concentration range of 0.61 nM to 10,000 nM. Data for calcium ion ($Ca^{+2}$) responses are obtained in arbitrary fluorescence units and not translated into $Ca^{+2}$ concentrations. $IC_{50}$ values (nM) are determined through a linear regression analysis using the Levenburg Marquardt algorithm.

Table I lists the test results for some of the compounds of the present invention:

TABLE 1

Biological Data: Activity Potency of Compounds against Human S1P3 Receptor nM, ($IC_{50}$), % Inhibition:

| Comp. no. | Structure | S1P3 $IC_{50}$ | S1P3 % Inhibition |
|---|---|---|---|
| 272 | 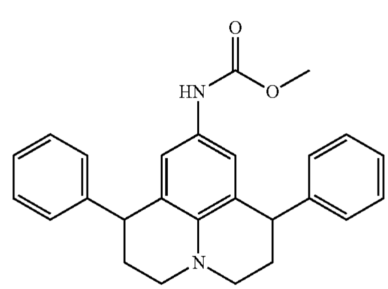 [SMILES: COC(=O)Nc1cc2c3c(c1)C(c1ccccc1)CCN3CCC2c1ccccc1] | 8.3 | 102 |
| 273 | 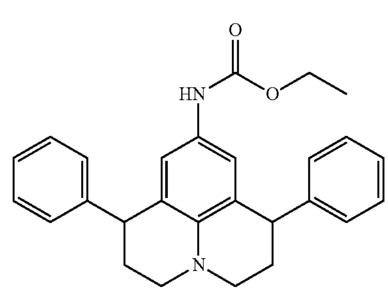 [SMILES: CCOC(=O)Nc1cc2c3c(c1)C(c1ccccc1)CCN3CCC2c1ccccc1] | 63 | 101 |

TABLE 1-continued

Biological Data: Activity Potency of Compounds against Human S1P3 Receptor nM, (IC$_{50}$), % Inhibition:

| Comp. no. | Structure | S1P3 IC$_{50}$ | S1P3 % Inhibition |
|---|---|---|---|
| 274 | 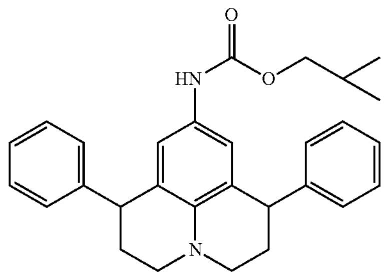 [SMILES: CC(C)COC(=O)Nc1cc2c3c(c1)C(c1ccccc1)CCN3CCC2c1ccccc1] | 64 | 100 |
| 275 | 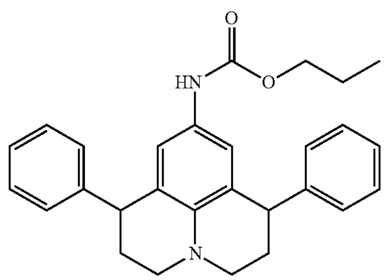 [SMILES: CCCOC(=O)Nc1cc2c3c(c1)C(c1ccccc1)CCN3CCC2c1ccccc1] | 12.2 | 100 |
| 276 | 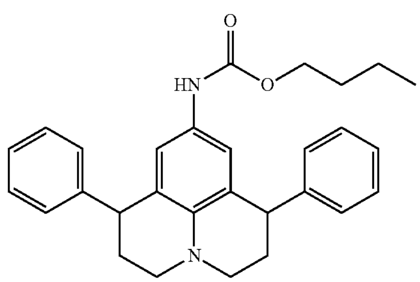 [SMILES: CCCCOC(=O)Nc1cc2c3c(c1)C(c1ccccc1)CCN3CCC2c1ccccc1] | 8.7 | 101 |
| 277 | 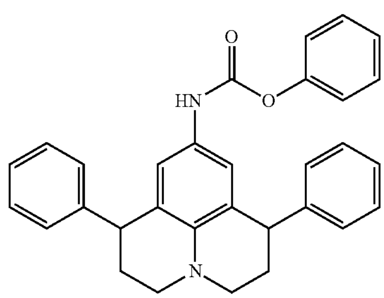 [SMILES: O=C(Nc1cc2c3c(c1)C(c1ccccc1)CCN3CCC2c1ccccc1)Oc1ccccc1] | 901 | 91 |
| 278 | 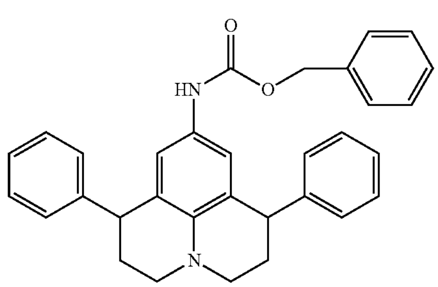 [SMILES: O=C(Nc1cc2c3c(c1)C(c1ccccc1)CCN3CCC2c1ccccc1)OCc1ccccc1] | 66 | 101 |

TABLE 1-continued

Biological Data: Activity Potency of Compounds against Human S1P3 Receptor nM, (IC$_{50}$), % Inhibition:

| Comp. no. | Structure | S1P3 IC$_{50}$ | S1P3 % Inhibition |
|---|---|---|---|
| 484 | 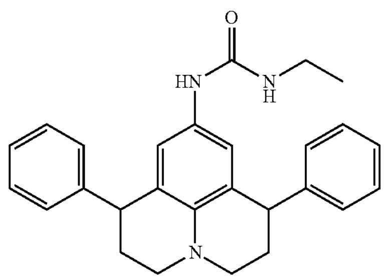 [SMILES: CCNC(=O)Nc1cc2c3c(c1)C(c1ccccc1)CCN3CCC2c1ccccc1] | 77 | 101 |
| 485 | 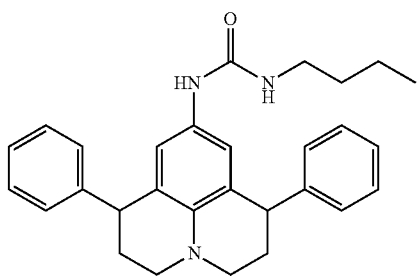 [SMILES: CCCCNC(=O)Nc1cc2c3c(c1)C(c1ccccc1)CCN3CCC2c1ccccc1] | 52 | 100 |
| 486 | 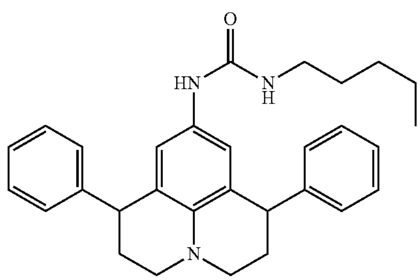 [SMILES: CCCCCNC(=O)Nc1cc2c3c(c1)C(c1ccccc1)CCN3CCC2c1ccccc1] | 82 | 100 |
| 487 | 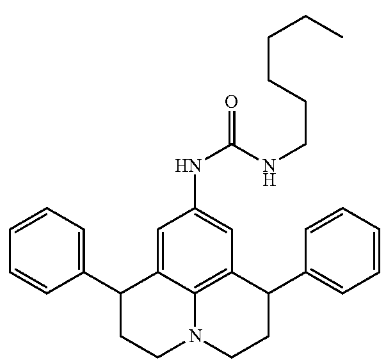 [SMILES: CCCCCCNC(=O)Nc1cc2c3c(c1)C(c1ccccc1)CCN3CCC2c1ccccc1] | 301 | 100 |
| 405 | 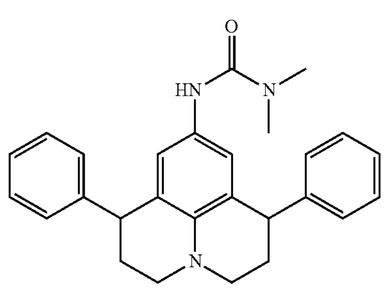 | 131 | 98 |

TABLE 1-continued
Biological Data: Activity Potency of Compounds against Human S1P3 Receptor nM, (IC$_{50}$), % Inhibition:
| Comp. no. | Structure | S1P3 IC$_{50}$ | S1P3 % Inhibition |
|---|---|---|---|
| 983 | 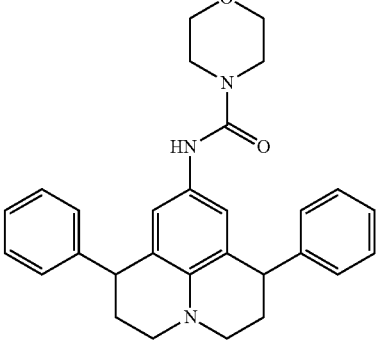 | 130 | 100 |
| 769 | 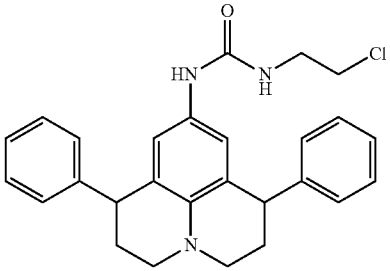 [SMILES: O=C(NCCCl)Nc1cc2c3c(c1)C(c1ccccc1)CCN3CCC2c1ccccc1] | 374 | 100 |
| 773 | 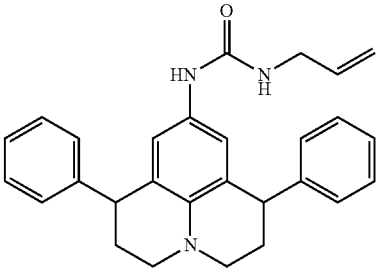 [SMILES: C=CCNC(=O)Nc1cc2c3c(c1)C(c1ccccc1)CCN3CCC2c1ccccc1] | 160 | 100 |
| 094 | 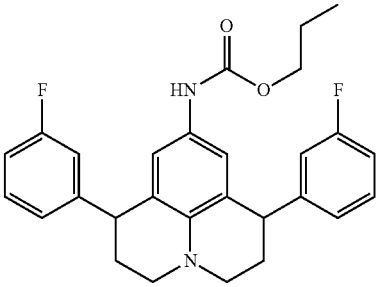 [SMILES: CCCOC(=O)Nc1cc2c3c(c1)C(c1cccc(F)c1)CCN3CCC2c1cccc(F)c1] | 234 | 101 |
| 093 | 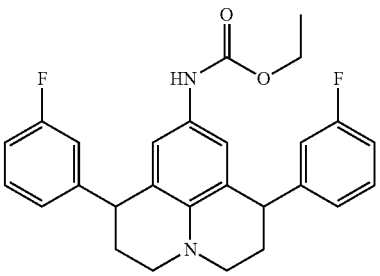 [SMILES: CCOC(=O)Nc1cc2c3c(c1)C(c1cccc(F)c1)CCN3CCC2c1cccc(F)c1] | 48 | 102 |

TABLE 1-continued

Biological Data: Activity Potency of Compounds against Human S1P3 Receptor nM, ($IC_{50}$), % Inhibition:

| Comp. no. | Structure | S1P3 $IC_{50}$ | S1P3 % Inhibition |
|---|---|---|---|
| (+)-enantiomer | 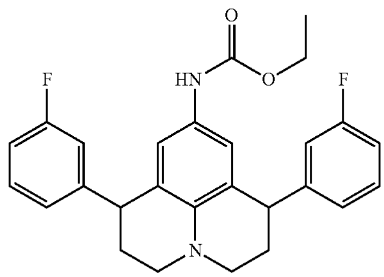 [SMILES: CCOC(=O)Nc1cc2c3c(c1)C(c1cccc(F)c1)CCN3CCC2c1cccc(F)c1] | 3 | 97 |
| (−)-enantiomer | 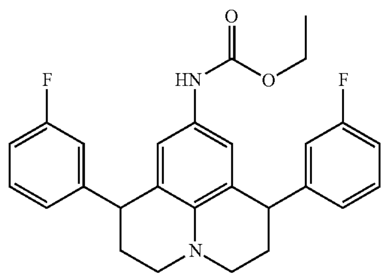 [SMILES: CCOC(=O)Nc1cc2c3c(c1)C(c1cccc(F)c1)CCN3CCC2c1cccc(F)c1] | 230 | 97 |
| 202 | 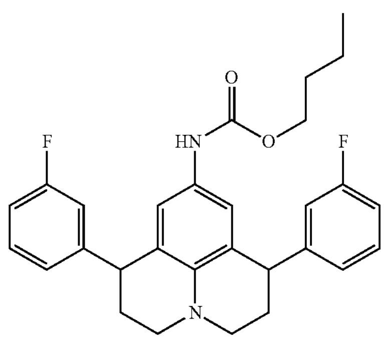 [SMILES: CCCCOC(=O)Nc1cc2c3c(c1)C(c1cccc(F)c1)CCN3CCC2c1cccc(F)c1] | 272 | 98 |
| 779 | 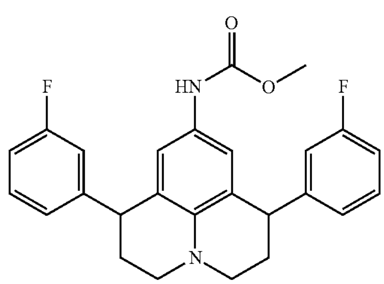 [SMILES: COC(=O)Nc1cc2c3c(c1)C(c1cccc(F)c1)CCN3CCC2c1cccc(F)c1] | 23 | 101 |
| 268 | 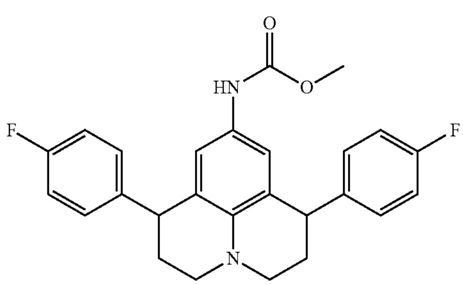 [SMILES: COC(=O)Nc1cc2c3c(c1)C(c1ccc(F)cc1)CCN3CCC2c1ccc(F)cc1] | 5 | 98 |

TABLE 1-continued

Biological Data: Activity Potency of Compounds against Human S1P3 Receptor nM, (IC$_{50}$), % Inhibition:

| Comp. no. | Structure | S1P3 IC$_{50}$ | S1P3 % Inhibition |
|---|---|---|---|
| (+)-enantiomer | | 1.6 | 98 |
| (−)-enantiomer | 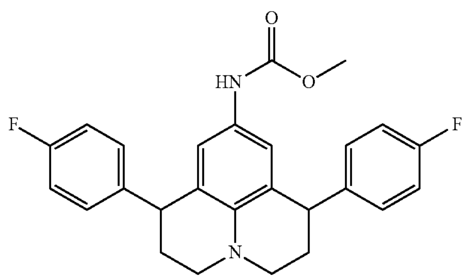 [SMILES: COC(=O)Nc1cc2c3c(c1)C(c1ccc(F)cc1)CCN3CCC2c1ccc(F)cc1] | NA | |
| 095 | 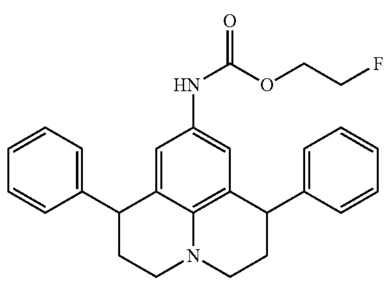 [SMILES: O=C(Nc1cc2c3c(c1)C(c1ccccc1)CCN3CCC2c1ccccc1)OCCF] | 56 | 102 |
| 067 | 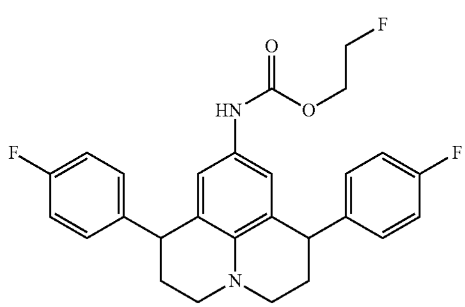 [SMILES: O=C(Nc1cc2c3c(c1)C(c1ccc(F)cc1)CCN3CCC2c1ccc(F)cc1)OCCF] | 8 | 98 |
| (+)-enantiomer | | 3 | 99 |

TABLE 1-continued

Biological Data: Activity Potency of Compounds against Human S1P3 Receptor nM, (IC$_{50}$), % Inhibition:

| Comp. no. | Structure | S1P3 IC$_{50}$ | S1P3 % Inhibition |
|---|---|---|---|
| (−)-enantiomer | 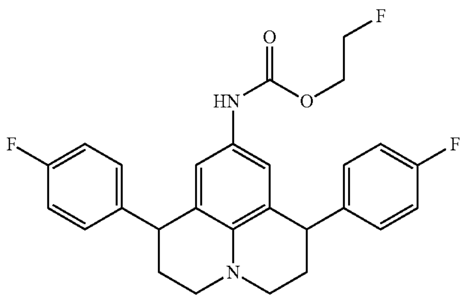 [SMILES: O=C(Nc1cc2c3c(c1)C(c1ccc(F)cc1)CCN3CCC2c1ccc(F)cc1)OCCF] | NA | |
| 354 | 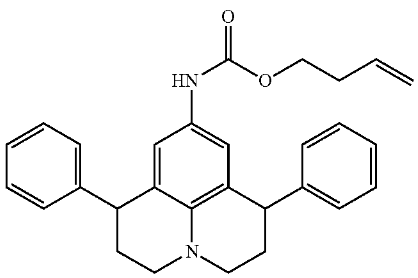 [SMILES: C=CCCOC(=O)Nc1cc2c3c(c1)C(c1ccccc1)CCN3CCC2c1ccccc1] | 16 | 97 |
| 353 | 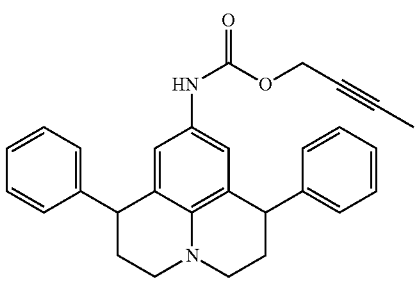 [SMILES: CC#CCOC(=O)Nc1cc2c3c(c1)C(c1ccccc1)CCN3CCC2c1ccccc1] | 13 | 98 |
| 352 | 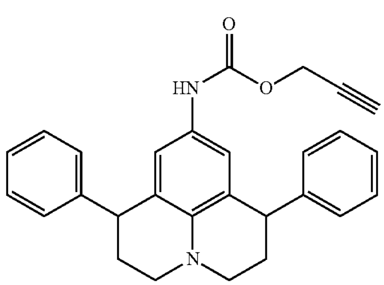 [SMILES: C#CCOC(=O)Nc1cc2c3c(c1)C(c1ccccc1)CCN3CCC2c1ccccc1] | 40 | 97 |
| 206 | 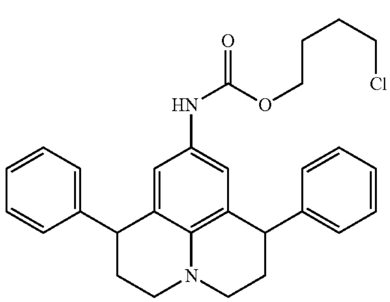 [SMILES: O=C(Nc1cc2c3c(c1)C(c1ccccc1)CCN3CCC2c1ccccc1)OCCCCCl] | 62 | 100 |

TABLE 1-continued
Biological Data: Activity Potency of Compounds against Human S1P3 Receptor nM, (IC$_{50}$), % Inhibition:
| Comp. no. | Structure | S1P3 IC$_{50}$ | S1P3 % Inhibition |
|---|---|---|---|
| 205 | 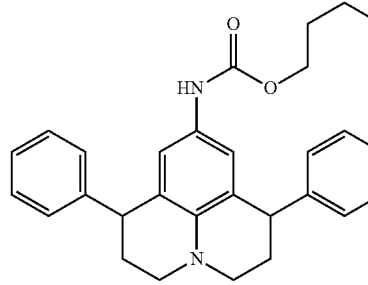 | 8 | 99 |
| (+)-enantiomer | 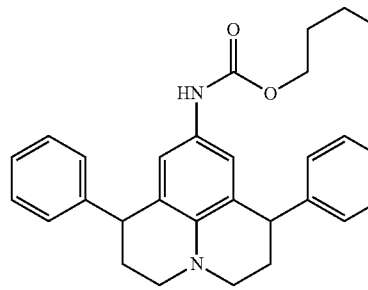 | 4 | 99 |
| (−)-enantiomer | 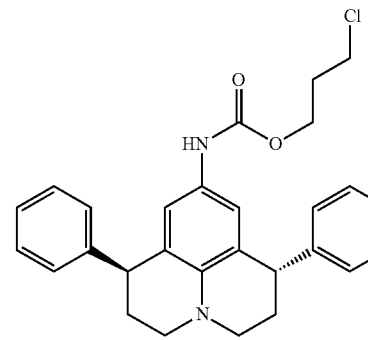 | 1659 | |
| 699 | 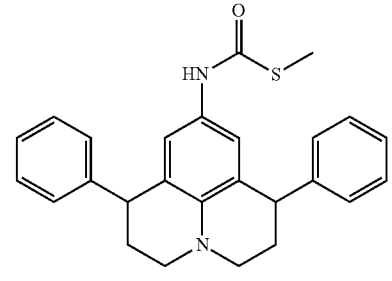 [SMILES: CSC(=O)Nc1cc2c3c(c1)C(c1ccccc1)CCN3CCC2c1ccccc1] | 4 | 100 |
| (+)-enantiomer | 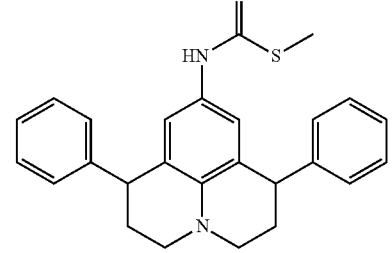 | 1.6 | 98 |

TABLE 1-continued

Biological Data: Activity Potency of Compounds against Human S1P3 Receptor nM, ($IC_{50}$), % Inhibition:

| Comp. no. | Structure | S1P3 $IC_{50}$ | S1P3 % Inhibition |
|---|---|---|---|
| (−)-enantiomer | | NA | |
| 700 | 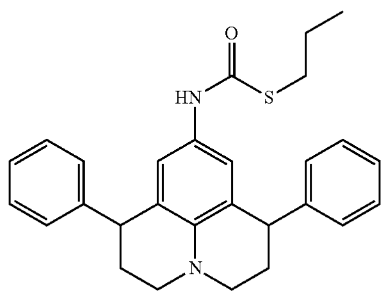 [SMILES: CCCSC(=O)Nc1cc2c3c(c1)C(c1ccccc1)CCN3CCC2c1ccccc1] | 7 | 100 |
| (+)-enantiomer | 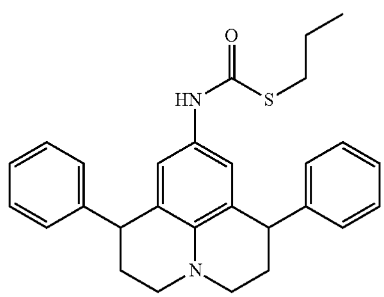 [SMILES: CCCSC(=O)Nc1cc2c3c(c1)C(c1ccccc1)CCN3CCC2c1ccccc1] | 13 | 98 |
| (−)-enantiomer | | NA | |
| 148 | 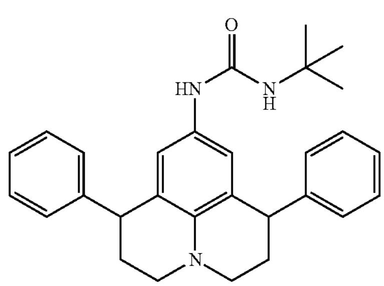 [SMILES: CC(C)(C)NC(=O)Nc1cc2c3c(c1)C(c1ccccc1)CCN3CCC2c1ccccc1] | 38 | 101 |

TABLE 1-continued

Biological Data: Activity Potency of Compounds against Human S1P3 Receptor nM, (IC$_{50}$), % Inhibition:

| Comp. no. | Structure | S1P3 IC$_{50}$ | S1P3 % Inhibition |
|---|---|---|---|
| 258 | 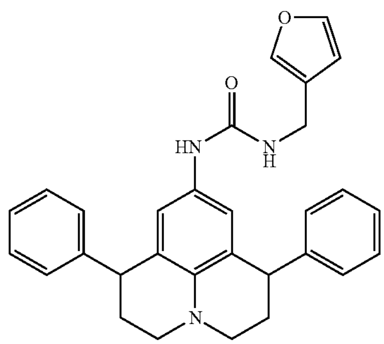 [SMILES: O=C(NCc1ccoc1)Nc1cc2c3c(c1)C(c1ccccc1)CCN3CCC2c1ccccc1] | 59 | 100 |
| 256 | 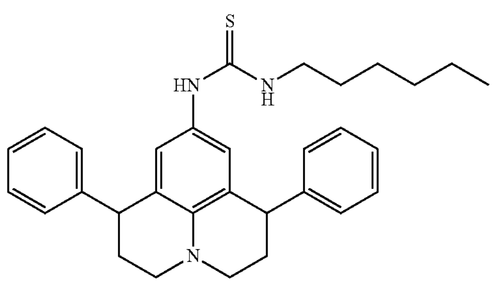 [SMILES: CCCCCCNC(=S)Nc1cc2c3c(c1)C(c1ccccc1)CCN3CCC2c1ccccc1] | 78 | 100 |
| 255 | 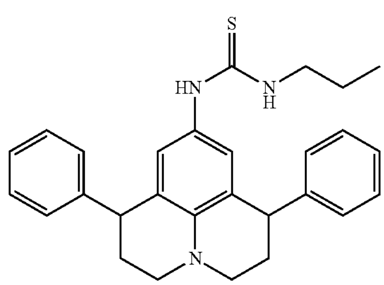 [SMILES: CCCNC(=S)Nc1cc2c3c(c1)C(c1ccccc1)CCN3CCC2c1ccccc1] | 153 | 99 |
| 829 | 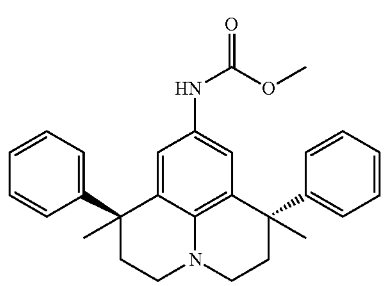 [SMILES: COC(=O)Nc1cc2c3c(c1)[C@](C)(c1ccccc1)CCN3CC[C@@]2(C)c1ccccc1] | 7 | 97 |
| 941 | 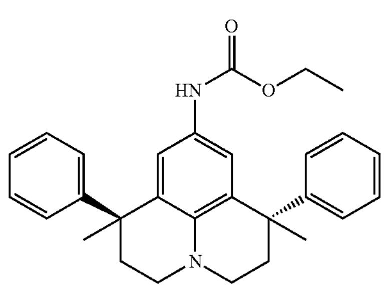 [SMILES: CCOC(=O)Nc1cc2c3c(c1)[C@](C)(c1ccccc1)CCN3CC[C@@]2(C)c1ccccc1] | 13 | 100 |

TABLE 1-continued

Biological Data: Activity Potency of Compounds against Human S1P3 Receptor nM, (IC$_{50}$), % Inhibition:

| Comp. no. | Structure | S1P3 IC$_{50}$ | S1P3 % Inhibition |
|---|---|---|---|
| 942 | 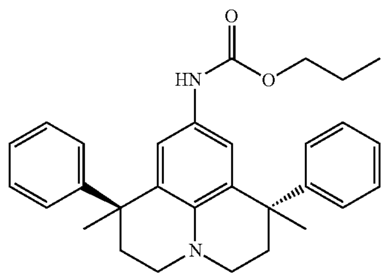 [SMILES: CCCOC(=O)Nc1cc2c3c(c1)[C@](C)(c1ccccc1)CCN3CC[C@@]2(C)c1ccccc1] | 72 | 100 |
| 943 | 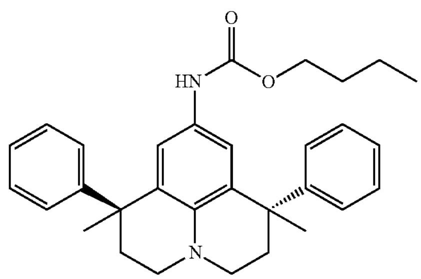 [SMILES: CCCCOC(=O)Nc1cc2c3c(c1)[C@](C)(c1ccccc1)CCN3CC[C@@]2(C)c1ccccc1] | 75 | 100 |
| 944 | 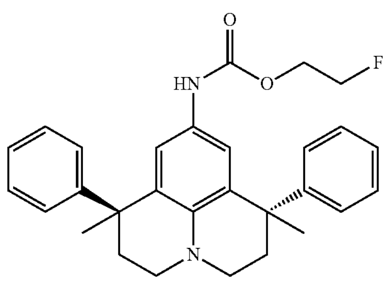 [SMILES: C[C@@]1(c2ccccc2)CCN2CC[C@@](C)(c3ccccc3)c3cc(NC(=O)OCCF)cc1c32] | 27 | 100 |
| 945 | 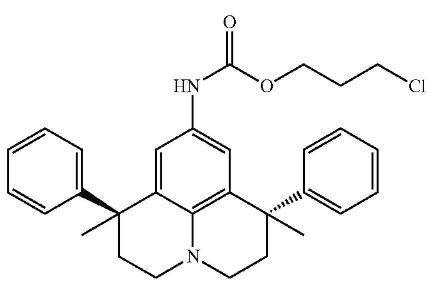 [SMILES: C[C@@]1(c2ccccc2)CCN2CC[C@@](C)(c3ccccc3)c3cc(NC(=O)OCCCCl)cc1c32] | 68 | 100 |
| 354 | 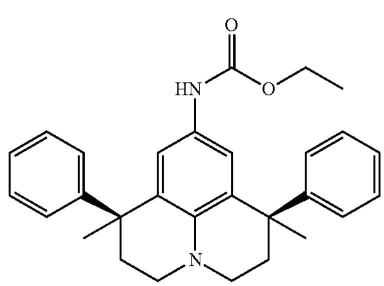 [SMILES: CCOC(=O)Nc1cc2c3c(c1)[C@@](C)(c1ccccc1)CCN3CC[C@@]2(C)c1ccccc1] | 36 | 98 |

TABLE 1-continued

Biological Data: Activity Potency of Compounds against Human S1P3 Receptor nM, (IC$_{50}$), % Inhibition:

| Comp. no. | Structure | S1P3 IC$_{50}$ | S1P3 % Inhibition |
|---|---|---|---|
| 355 | 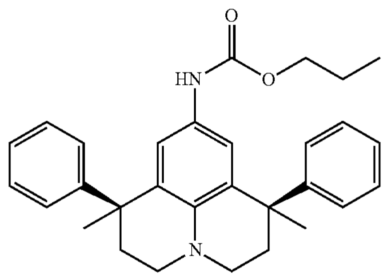 [SMILES: CCCOC(=O)Nc1cc2c3c(c1)[C@@](C)(c1ccccc1)CCN3CC[C@@]2(C)c1ccccc1] | 316 | 98 |
| 674 | 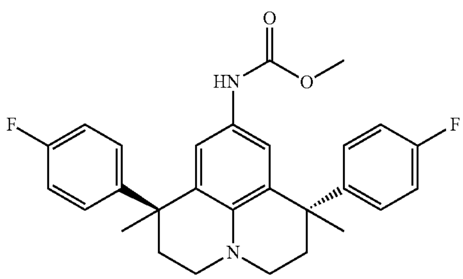 [SMILES: COC(=O)Nc1cc2c3c(c1)[C@](C)(c1ccc(F)cc1)CCN3CC[C@@]2(C)c1ccc(F)cc1] | 46 | 96 |
| 672 | 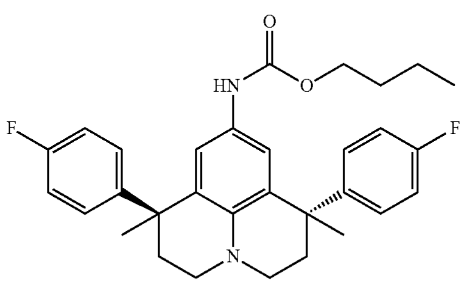 [SMILES: CCCCOC(=O)Nc1cc2c3c(c1)[C@](C)(c1ccc(F)cc1)CCN3CC[C@@]2(C)c1ccc(F)cc1] | 86 | 89 |
| 583 | 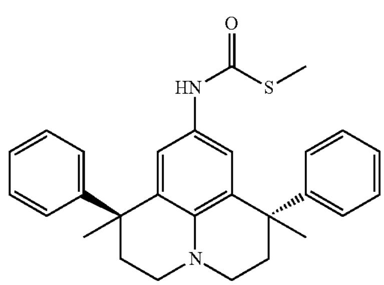 | 10 | 98 |
| 585 | 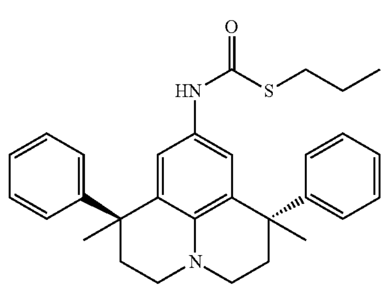 | 5 | 98 |

TABLE 1-continued

Biological Data: Activity Potency of Compounds against Human S1P3 Receptor nM, ($IC_{50}$), % Inhibition:

| Comp. no. | Structure | S1P3 $IC_{50}$ | S1P3 % Inhibition |
|---|---|---|---|
| 582 | 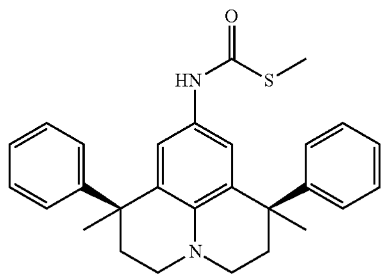 [SMILES: CSC(=O)Nc1cc2c3c(c1)[C@@](C)(c1ccccc1)CCN3CC[C@@]2(C)c1ccccc1] | 4 | 99 |
| 584 | 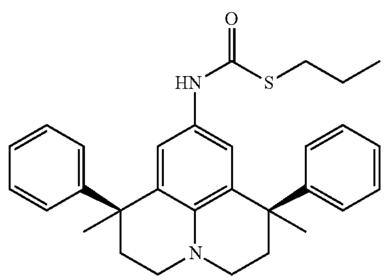 | 16 | 98 |
| 671 | 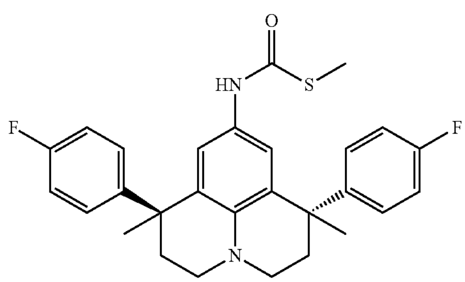 | 25 | 97 |
| 673 | 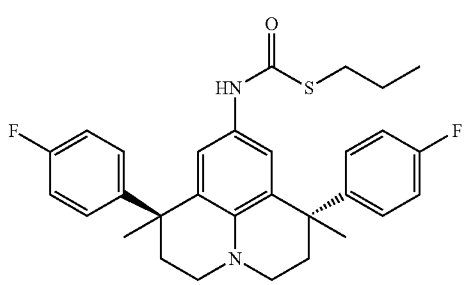 [SMILES: CCCSC(=O)Nc1cc2c3c(c1)[C@](C)(c1ccc(F)cc1)CCN3CC[C@@]2(C)c1ccc(F)cc1] | 62 | 97 |
| 249 | 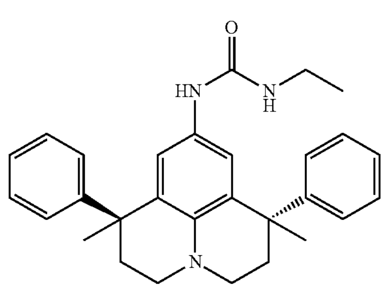 | 194 | 100 |

TABLE 1-continued
Biological Data: Activity Potency of Compounds against Human S1P3 Receptor nM, (IC$_{50}$), % Inhibition:
| Comp. no. | Structure | S1P3 IC$_{50}$ | S1P3 % Inhibition |
|---|---|---|---|
| 250 | 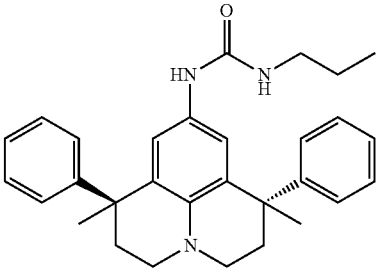 [SMILES: CCCNC(=O)Nc1cc2c3c(c1)[C@](C)(c1ccccc1)CCN3CC[C@@]2(C)c1ccccc1] | 523 | 100 |
| 581 | 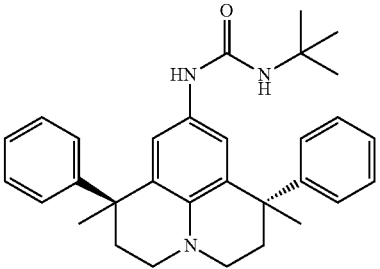 [SMILES: CC(C)(C)NC(=O)Nc1cc2c3c(c1)[C@](C)(c1ccccc1)CCN3CC[C@@]2(C)c1ccccc1] | 349 | 98 |
| 580 | 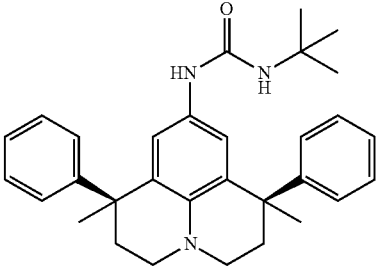 [SMILES: CC(C)(C)NC(=O)Nc1cc2c3c(c1)[C@@](C)(c1ccccc1)CCN3CC[C@@]2(C)c1ccccc1] | 62 | 99 |
| 775 | 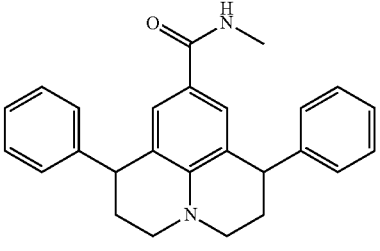 [SMILES: CNC(=O)c1cc2c3c(c1)C(c1ccccc1)CCN3CCC2c1ccccc1] | 619 | 100 |
| 409 | 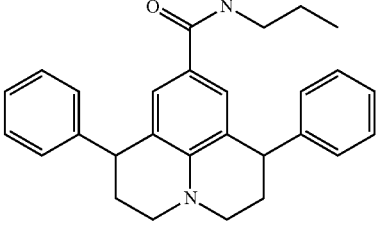 | 874 | 89 |

TABLE 1-continued

Biological Data: Activity Potency of Compounds against Human S1P3 Receptor nM, (IC$_{50}$), % Inhibition:

| Comp. no. | Structure | S1P3 IC$_{50}$ | S1P3 % Inhibition |
|---|---|---|---|
| 481 | 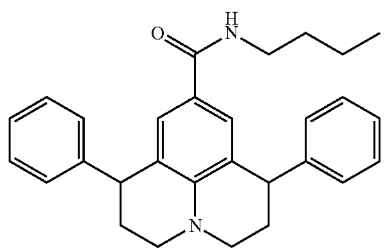 [SMILES: CCCCNC(=O)c1cc2c3c(c1)C(c1ccccc1)CCN3CCC2c1ccccc1] | 210 | 98 |

TABLE 2

Additional Compounds of the Present Invention:

| Compound | Structure |
|---|---|
| 1 | 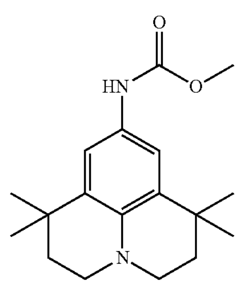 |
| 2 | 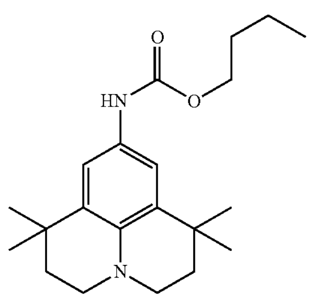 [SMILES: CCCCOC(=O)Nc1cc2c3c(c1)C(C)(C)CCN3CCC2(C)C] |
| 3 | 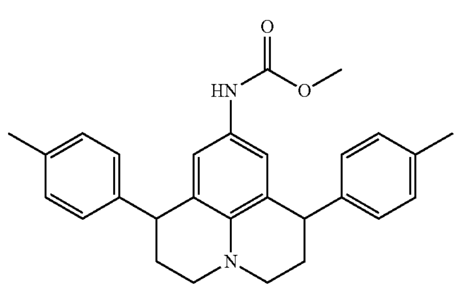 |

TABLE 2-continued

Additional Compounds of the Present Invention:

| Compound | Structure |
|---|---|
| 4 | *ethyl carbamate derivative* |
| 5 | *propyl carbamate derivative* |
| 6 | *butyl carbamate derivative* |
| 7 | *propargyl carbamate derivative* |
| 8 | *3-chloropropyl carbamate derivative* |

TABLE 2-continued

Additional Compounds of the Present Invention:

| Compound | Structure |
|---|---|
| 9 | (structure) |
| 10 | (structure) |
| 11 | (structure) |
| 12 | (structure) |
| 13 | (structure) |

TABLE 2-continued

Additional Compounds of the Present Invention:

| Compound | Structure |
|---|---|
| 14 | *(methyl carbamate derivative)* |
| 15 | *(ethyl carbamate derivative)* |
| 16 | *(butyl carbamate derivative)* |
| 17 | *(2-fluoroethyl carbamate derivative)* |
| 18 | *(3-chloropropyl carbamate derivative)* |

TABLE 2-continued
Additional Compounds of the Present Invention:
| Compound | Structure |
|---|---|
| 19 | 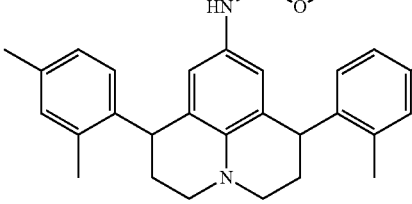 |
| 20 | 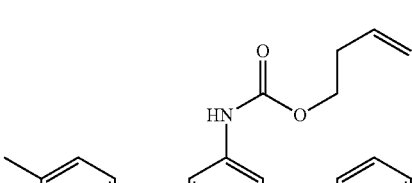 |
| 21 | 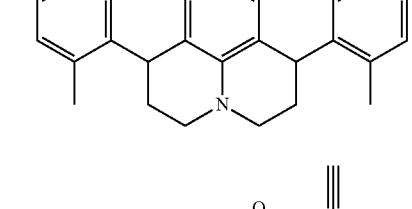 |
| 22 | 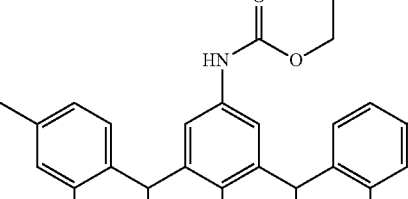 |
| 23 | 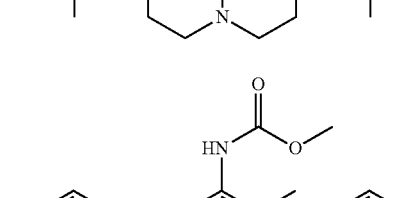 |

TABLE 2-continued

Additional Compounds of the Present Invention:

| Compound | Structure |
|---|---|
| 24 | 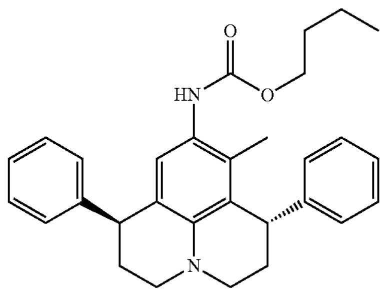 [SMILES: CCCCOC(=O)Nc1cc2c3c(c1C)[C@H](c1ccccc1)CCN3CC[C@H]2c1ccccc1] |
| 25 | 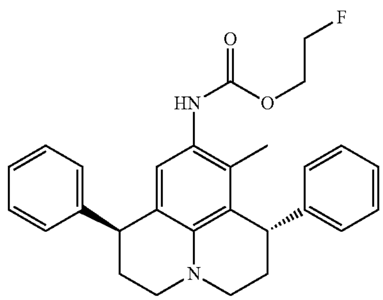 [SMILES: Cc1c(NC(=O)OCCF)cc2c3c1[C@H](c1ccccc1)CCN3CC[C@H]2c1ccccc1] |
| 26 | 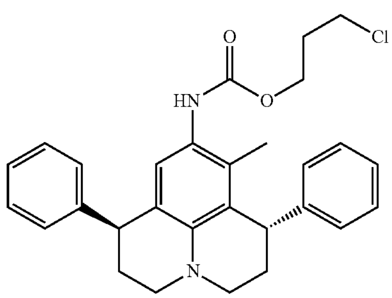 [SMILES: Cc1c(NC(=O)OCCCCl)cc2c3c1[C@H](c1ccccc1)CCN3CC[C@H]2c1ccccc1] |
| 27 | 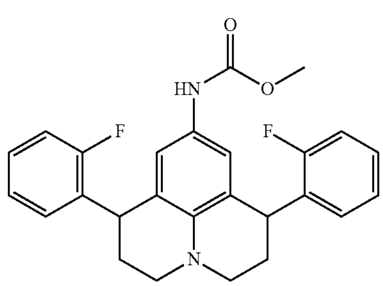 [SMILES: COC(=O)Nc1cc2c3c(c1)C(c1ccccc1F)CCN3CCC2c1ccccc1F] |
| 28 | 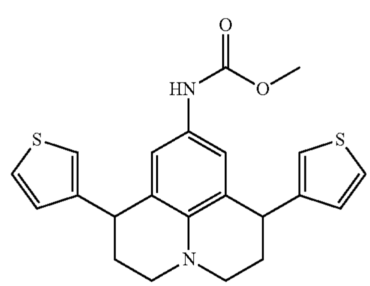 [SMILES: COC(=O)Nc1cc2c3c(c1)C(c1ccsc1)CCN3CCC2c1ccsc1] |

TABLE 2-continued
Additional Compounds of the Present Invention:
| Compound | Structure |
|---|---|
| 29 | 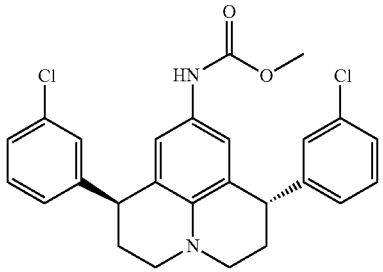 [SMILES: COC(=O)Nc1cc2c3c(c1)[C@H](c1cccc(Cl)c1)CCN3CC[C@H]2c1cccc(Cl)c1] |
| 30 | 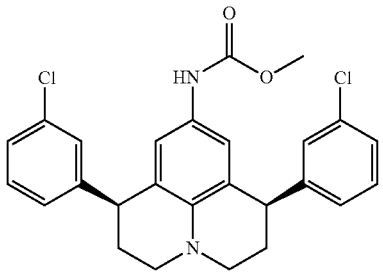 [SMILES: COC(=O)Nc1cc2c3c(c1)[C@H](c1cccc(Cl)c1)CCN3CC[C@@H]2c1cccc(Cl)c1] |
| 31 | 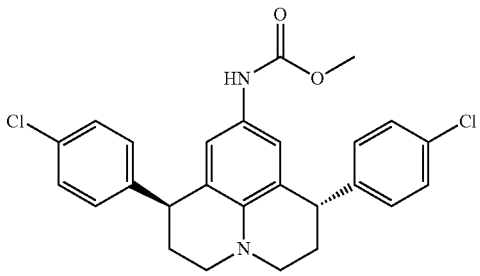 [SMILES: COC(=O)Nc1cc2c3c(c1)[C@H](c1ccc(Cl)cc1)CCN3CC[C@H]2c1ccc(Cl)cc1] |
| 32 | 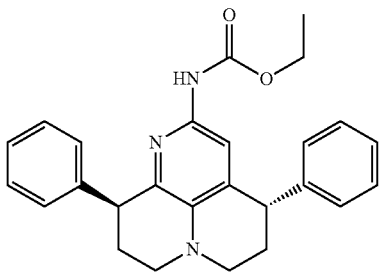 [SMILES: CCOC(=O)Nc1cc2c3c(n1)[C@H](c1ccccc1)CCN3CC[C@H]2c1ccccc1] |
| 33 | 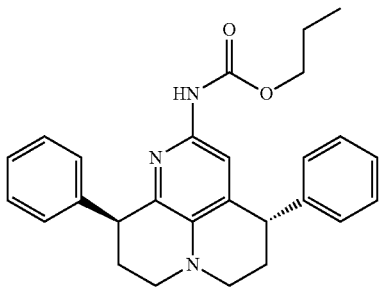 [SMILES: CCCOC(=O)Nc1cc2c3c(n1)[C@H](c1ccccc1)CCN3CC[C@H]2c1ccccc1] |

TABLE 2-continued

Additional Compounds of the Present Invention:

| Compound | Structure |
|---|---|
| 34 | (structure) |
| 35 | (structure) |
| 36 | (structure) |
| 37 | (structure) |
| 38 | (structure) |

TABLE 2-continued

Additional Compounds of the Present Invention:

| Compound | Structure |
|---|---|
| 39 | 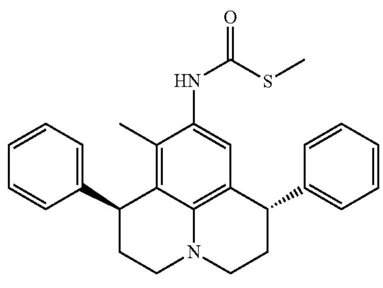 [SMILES: CSC(=O)Nc1cc2c3c(c1C)[C@H](c1ccccc1)CCN3CC[C@H]2c1ccccc1] |
| 40 | 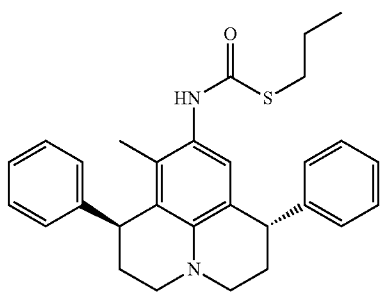 [SMILES: CCCSC(=O)Nc1cc2c3c(c1C)[C@H](c1ccccc1)CCN3CC[C@H]2c1ccccc1] |
| 41 | 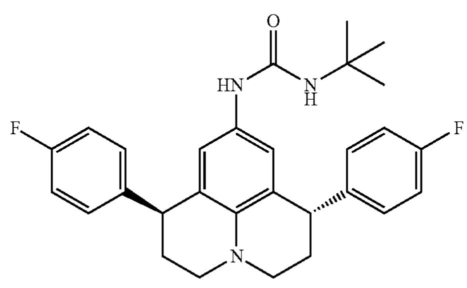 [SMILES: CC(C)(C)NC(=O)Nc1cc2c3c(c1)[C@H](c1ccc(F)cc1)CCN3CC[C@H]2c1ccc(F)cc1] |
| 42 | 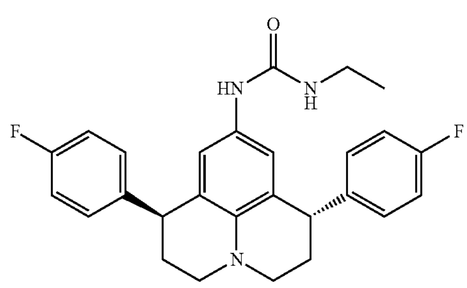 [SMILES: CCNC(=O)Nc1cc2c3c(c1)[C@H](c1ccc(F)cc1)CCN3CC[C@H]2c1ccc(F)cc1] |
| 43 | 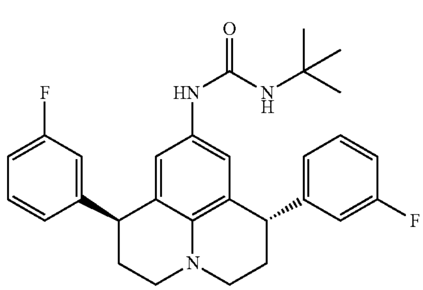 [SMILES: CC(C)(C)NC(=O)Nc1cc2c3c(c1)[C@H](c1cccc(F)c1)CCN3CC[C@H]2c1cccc(F)c1] |

TABLE 2-continued

Additional Compounds of the Present Invention:

| Compound | Structure |
|---|---|
| 44 | 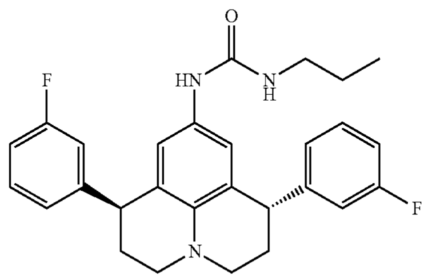 [SMILES: CCCNC(=O)Nc1cc2c3c(c1)[C@H](c1cccc(F)c1)CCN3CC[C@H]2c1cccc(F)c1] |
| 45 | 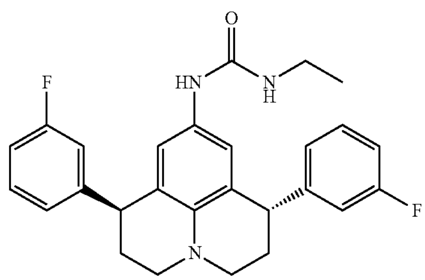 [SMILES: CCNC(=O)Nc1cc2c3c(c1)[C@H](c1cccc(F)c1)CCN3CC[C@H]2c1cccc(F)c1] |
| 46 | 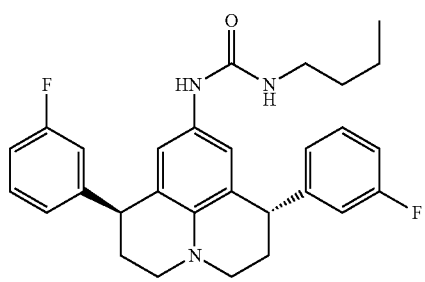 [SMILES: CCCCNC(=O)Nc1cc2c3c(c1)[C@H](c1cccc(F)c1)CCN3CC[C@H]2c1cccc(F)c1] |
| 47 | 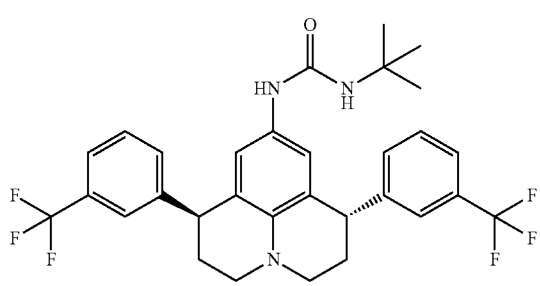 [SMILES: CC(C)(C)NC(=O)Nc1cc2c3c(c1)[C@H](c1cccc(C(F)(F)F)c1)CCN3CC[C@H]2c1cccc(C(F)(F)F)c1] |
| 48 | 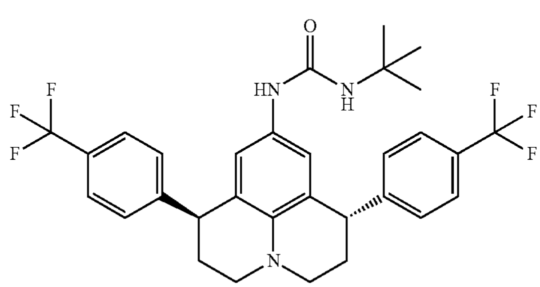 [SMILES: CC(C)(C)NC(=O)Nc1cc2c3c(c1)[C@H](c1ccc(C(F)(F)F)cc1)CCN3CC[C@H]2c1ccc(C(F)(F)F)cc1] |

TABLE 2-continued

Additional Compounds of the Present Invention:

| Compound | Structure |
|---|---|
| 49 | 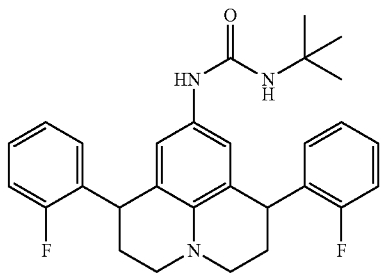 [SMILES: CC(C)(C)NC(=O)Nc1cc2c3c(c1)C(c1ccccc1F)CCN3CCC2c1ccccc1F] |
| 50 | 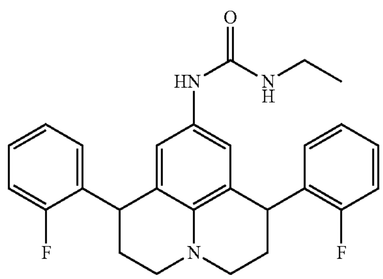 [SMILES: CCNC(=O)Nc1cc2c3c(c1)C(c1ccccc1F)CCN3CCC2c1ccccc1F] |
| 51 | 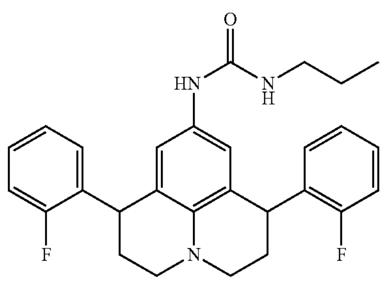 [SMILES: CCCNC(=O)Nc1cc2c3c(c1)C(c1ccccc1F)CCN3CCC2c1ccccc1F] |
| 52 | 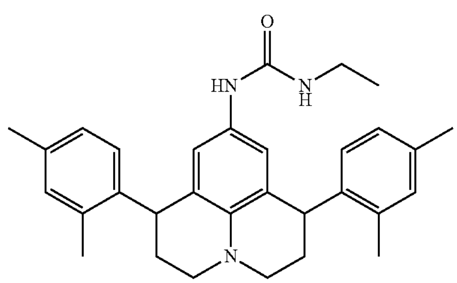 |
| 53 | 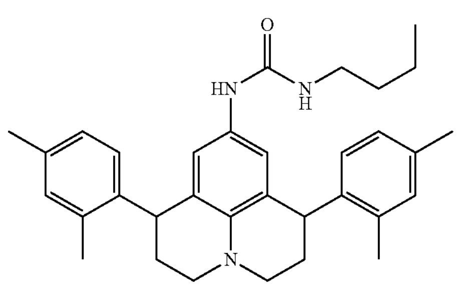 |

TABLE 2-continued

Additional Compounds of the Present Invention:

| Compound | Structure |
|---|---|
| 54 (+) Single enantiomer | 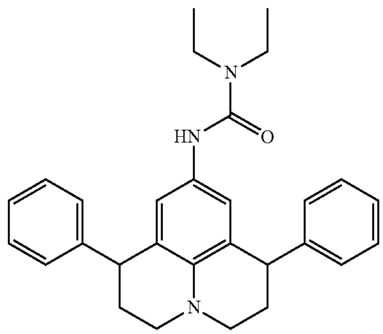 [SMILES: CCN(CC)C(=O)Nc1cc2c3c(c1)C(c1ccccc1)CCN3CCC2c1ccccc1] |
| 55 (−) Single enantiomer | 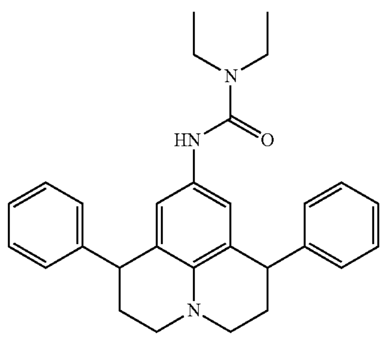 [SMILES: CCN(CC)C(=O)Nc1cc2c3c(c1)C(c1ccccc1)CCN3CCC2c1ccccc1] |
| 56 | 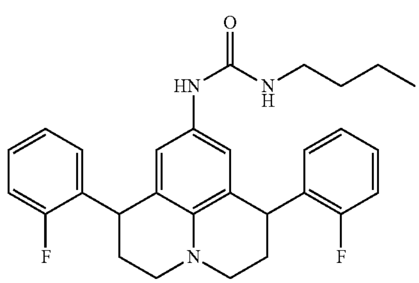 [SMILES: CCCCNC(=O)Nc1cc2c3c(c1)C(c1ccccc1F)CCN3CCC2c1ccccc1F] |
| 57 | 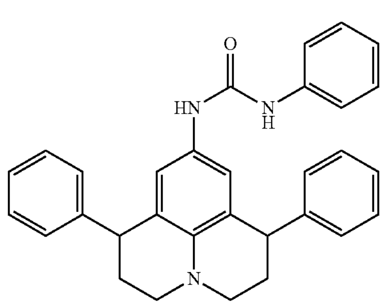 [SMILES: O=C(Nc1ccccc1)Nc1cc2c3c(c1)C(c1ccccc1)CCN3CCC2c1ccccc1] |

TABLE 2-continued

Additional Compounds of the Present Invention:

| Compound | Structure |
|---|---|
| 58 | *[structure: julolidine core with 1,7-diphenyl substituents and a urea linkage at the 9-position to a 3-chloro-2-fluorophenyl group]* |
| 59 | *[structure: julolidine core with 1,7-diphenyl substituents and a urea linkage at the 9-position to a 2-chlorophenyl group]* |
| 60 | *[structure: julolidine core with 1,7-diphenyl substituents and a urea linkage at the 9-position to a 2-methylbenzyl group]* |
| 61 | *[structure: julolidine core with 1,7-diphenyl substituents and an acylurea linkage at the 9-position to a chloroacetyl group]* |

TABLE 2-continued

Additional Compounds of the Present Invention:

| Compound | Structure |
|---|---|
| 62 | 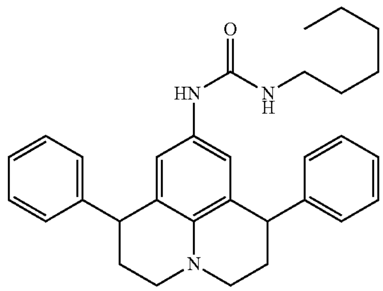 [SMILES: CCCCCCNC(=O)Nc1cc2c3c(c1)C(c1ccccc1)CCN3CCC2c1ccccc1] |
| 63 | 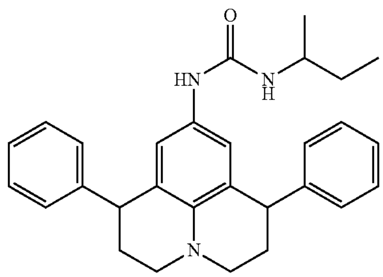 [SMILES: CCC(C)NC(=O)Nc1cc2c3c(c1)C(c1ccccc1)CCN3CCC2c1ccccc1] |
| 64 | 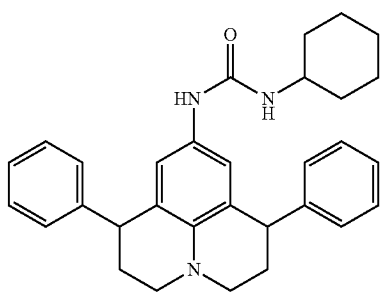 [SMILES: O=C(Nc1cc2c3c(c1)C(c1ccccc1)CCN3CCC2c1ccccc1)NC1CCCCC1] |
| 65 | 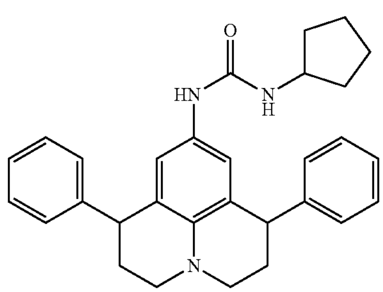 [SMILES: O=C(Nc1cc2c3c(c1)C(c1ccccc1)CCN3CCC2c1ccccc1)NC1CCCC1] |
| 66 | 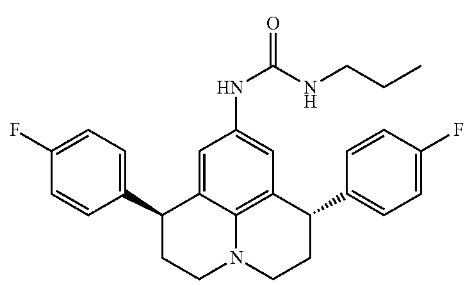 [SMILES: CCCNC(=O)Nc1cc2c3c(c1)[C@H](c1ccc(F)cc1)CCN3CC[C@H]2c1ccc(F)cc1] |

TABLE 2-continued

Additional Compounds of the Present Invention:

| Compound | Structure |
|---|---|
| 67 | 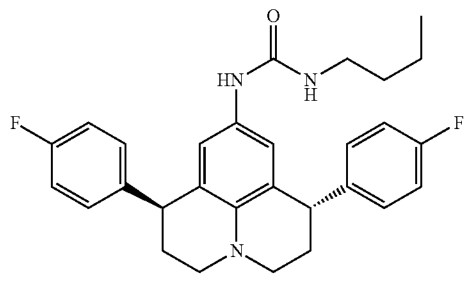 [SMILES: CCCCNC(=O)Nc1cc2c3c(c1)[C@H](c1ccc(F)cc1)CCN3CC[C@H]2c1ccc(F)cc1] |
| 68 | 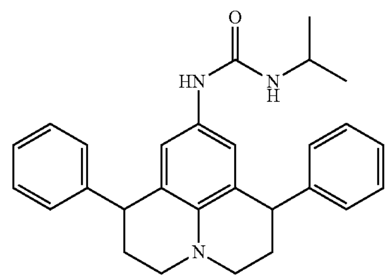 |
| 69 | 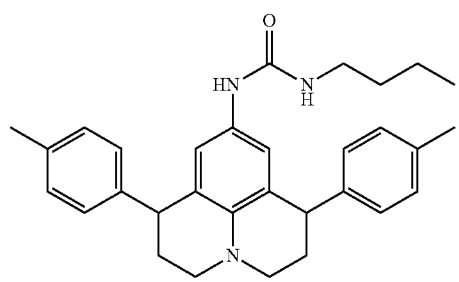 |
| 70 | 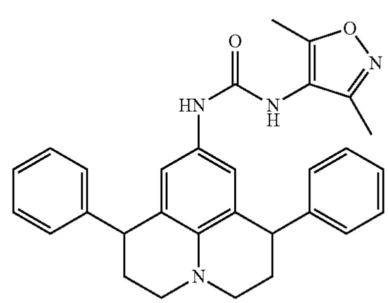 [SMILES: Cc1noc(C)c1NC(=O)Nc1cc2c3c(c1)C(c1ccccc1)CCN3CCC2c1ccccc1] |
| 71 | 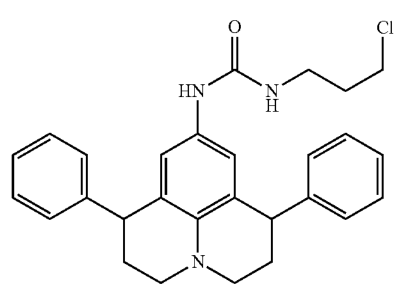 [SMILES: O=C(NCCCCl)Nc1cc2c3c(c1)C(c1ccccc1)CCN3CCC2c1ccccc1] |

TABLE 2-continued

Additional Compounds of the Present Invention:

| Compound | Structure |
|---|---|
| 72 | *structure: 1,7-dimethyl-1,7-diphenyl-julolidine with NHC(O)NH-butyl urea substituent* |
| 73 | *structure: 1,7-dimethyl-1,7-diphenyl-julolidine with NHC(O)NH-allyl urea substituent* |
| 74 | *structure: 1,7-dimethyl-1,7-diphenyl-julolidine with NHC(O)NH-ethyl urea substituent* |
| 75 | *structure: 1,7-dimethyl-1,7-diphenyl-julolidine with NHC(O)NH-propyl urea substituent* |
| 76 | *structure: 1,7-dimethyl-1,7-diphenyl-julolidine with NHC(O)NH-butyl urea substituent* |

The invention claimed is:

1. A method of facilitating ocular wound healing in a mammal, or of treating a disease or condition selected from macular degeneration, retinal edema, retinal degeneration, idiopathic pulmonary fibrosis, diabetic retinopathy, optic neuropathy, and glaucomatous retinopathy in a mammal in need of such treatment, comprising administering to said mammal a pharmaceutical composition comprising a substituted hydropyrido-quinoline represented by the structural formula:

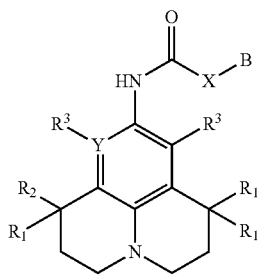

wherein:

Y is C or N;

X is oxygen, sulfur or $NR^N$;

$R^N$ is H or $C_{1-6}$ alkyl;

B is $C_{1-6}$ alkyl, $C_{1-6}$ alkenyl or $C_{1-6}$ alkyl having at least one halo atom of F, Cl, Br, or I as substituent;

$R^3$ is hydrogen or $C_{1-6}$ alkyl;

each $R^1$ is independently hydrogen or $C_{1-6}$ alkyl;

each $R^2$ is independently substituted or unsubstituted phenyl;

in combination with at least one additional component selected from the group consisting of one or more emulsifying agent, wetting agent, sweetening agent, flavoring agent, tonicity adjuster, preservative, buffer, anti-oxidant and combinations thereof.

2. The method according to claim 1, wherein the substituted hydropyrido-quinoline is selected from:

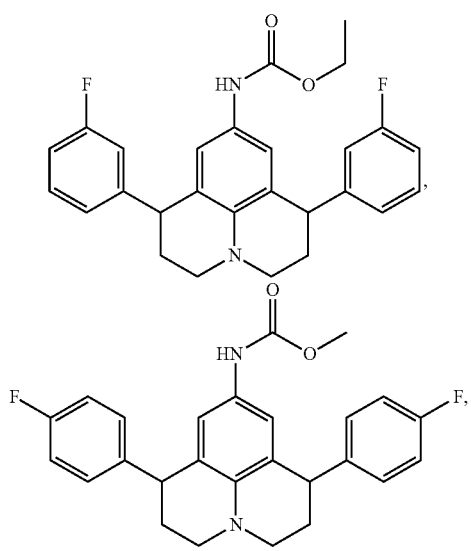

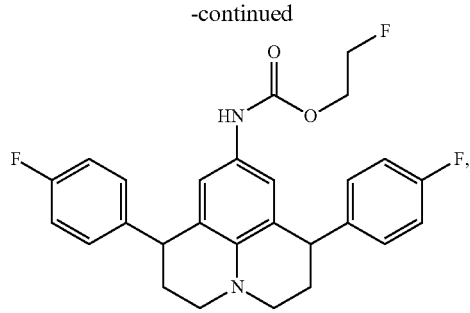

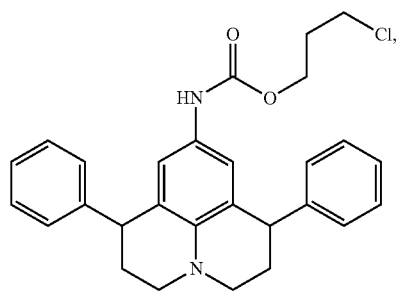

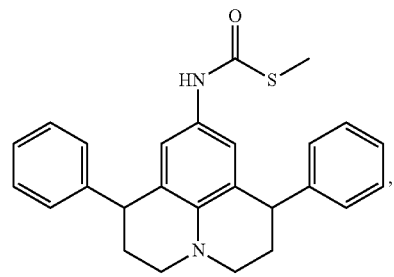

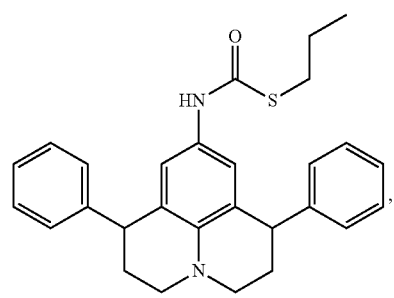

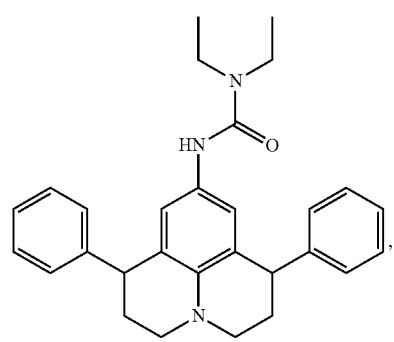

115
-continued
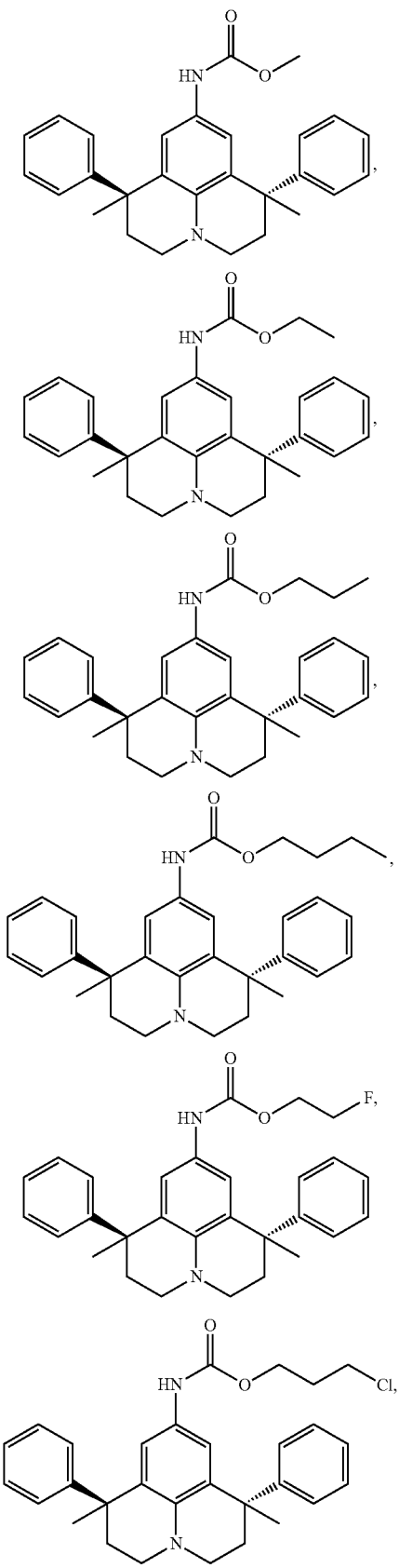
116
-continued
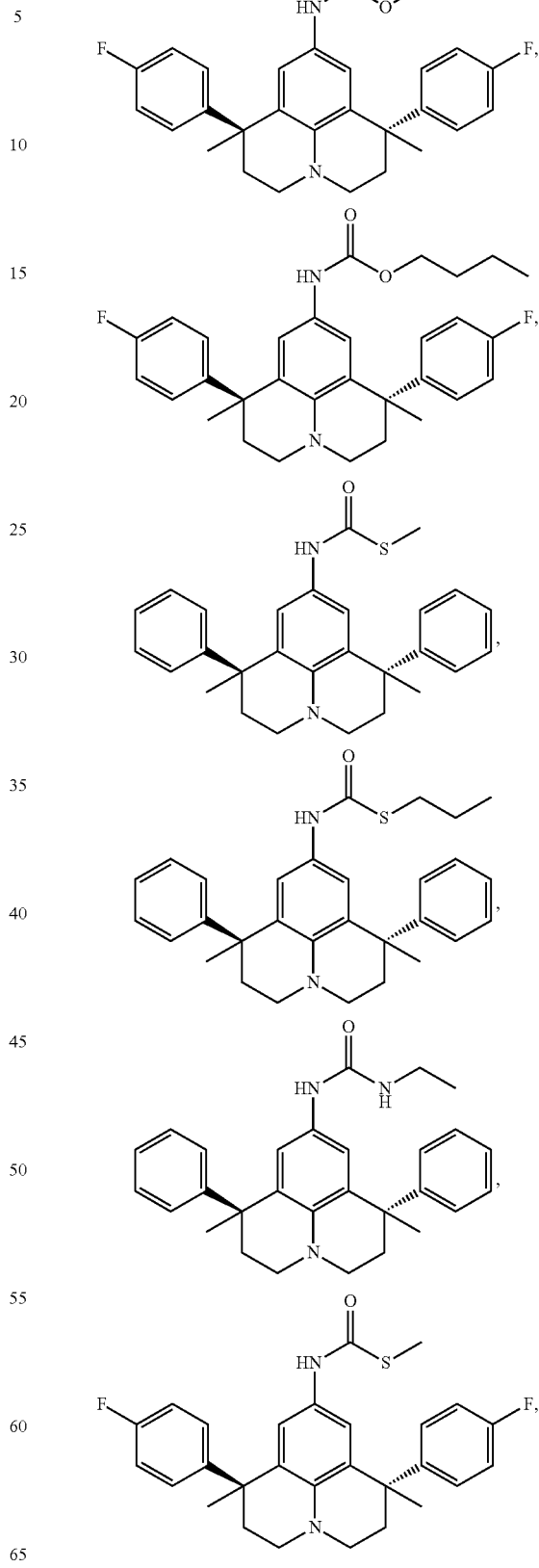

117
-continued
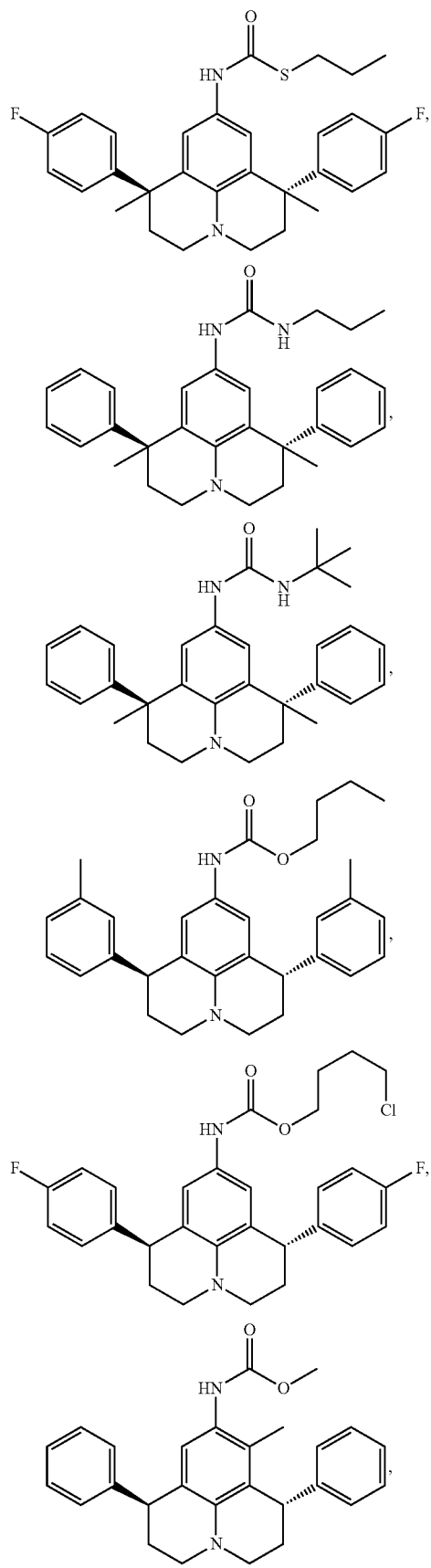
118
-continued
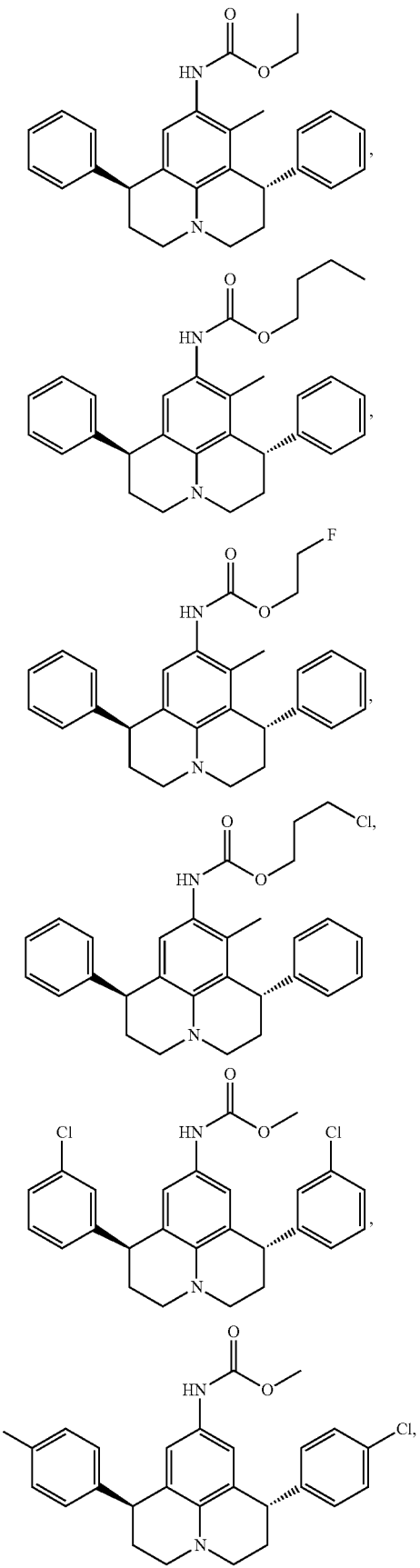

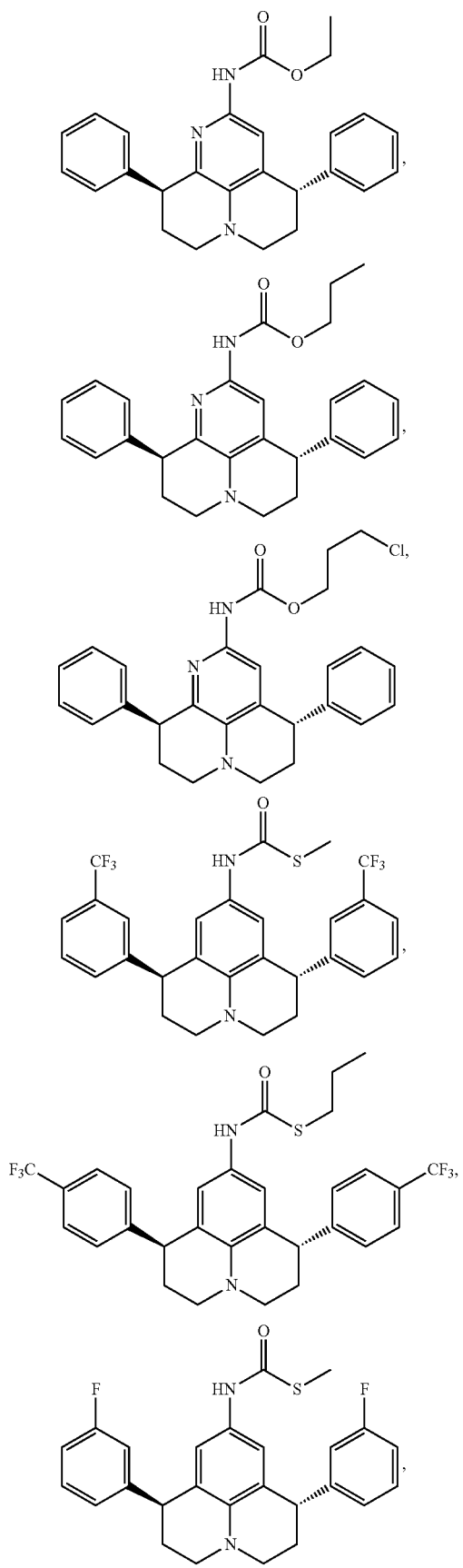
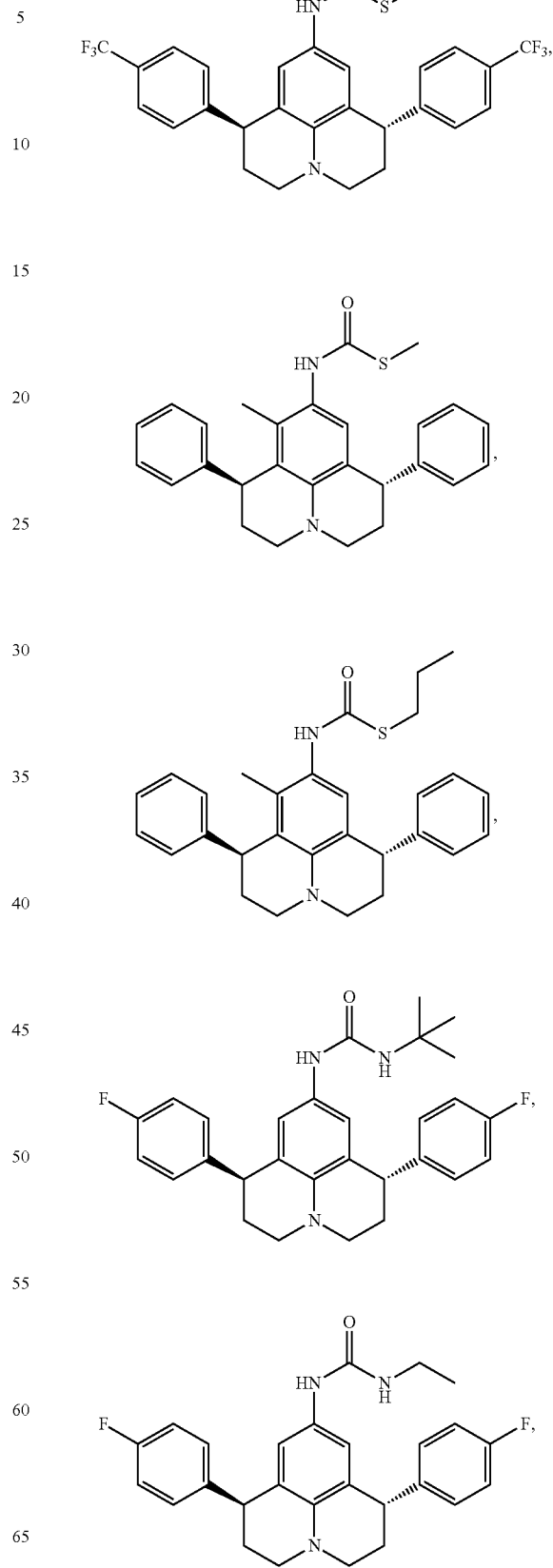

3. The method of claim 1, wherein the disease or condition is idiopathic pulmonary fibrosis.

4. The method of claim 1, wherein the disease or condition is ocular wound healing.

5. The method of claim 1, wherein the disease or condition is retinal edema.

6. The method of claim 1, wherein the disease or condition is diabetic retinopathy.

7. The method of claim 1, wherein the disease or condition is optic neuropathy.

8. The method of claim 1, wherein the disease or condition is glaucomatous retinopathy.

* * * * *

UNITED STATES PATENT AND TRADEMARK OFFICE
CERTIFICATE OF CORRECTION

PATENT NO.        : 8,431,702 B2
APPLICATION NO.   : 13/569418
DATED             : April 30, 2013
INVENTOR(S)       : Santosh C. Sinha et al.

It is certified that error appears in the above-identified patent and that said Letters Patent is hereby corrected as shown below:

On the title page, item (56), under "Other Publications", in column 2, line 6, delete "Boorg." and insert -- Bioorg. --, therefor.

On the title page, item (56), under "Other Publications", in column 2, line 7, delete "Boorg." and insert -- Bioorg. --, therefor.

On the title page, item (56), under "Other Publications", in column 2, line 8, delete "Boorg." and insert -- Bioorg. --, therefor.

On the title page, item (56), under "Other Publications", in column 2, line 10, delete "Boorg." and insert -- Bioorg. --, therefor.

On the title page, item (56), under "Other Publications", in column 2, line 11, delete "Boorg." and insert -- Bioorg. --, therefor.

On the title page, item (56), under "Other Publications", in column 2, line 14, delete "Phamacol." and insert -- Pharmacol. --, therefor.

On the title page, item (57), under "Abstract", in column 2, line 3, delete " 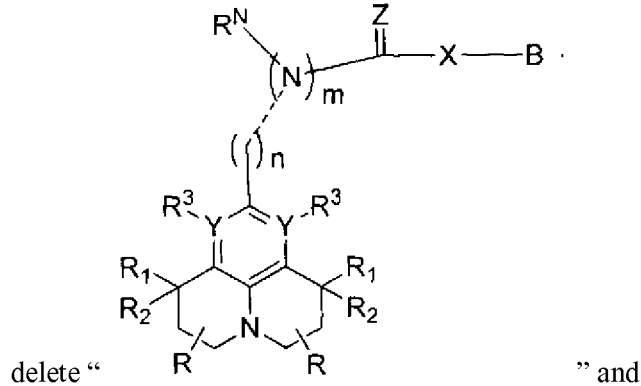 " and Signed and Sealed this
Eighth Day of October, 2013

Teresa Stanek Rea
*Deputy Director of the United States Patent and Trademark Office* insert -- 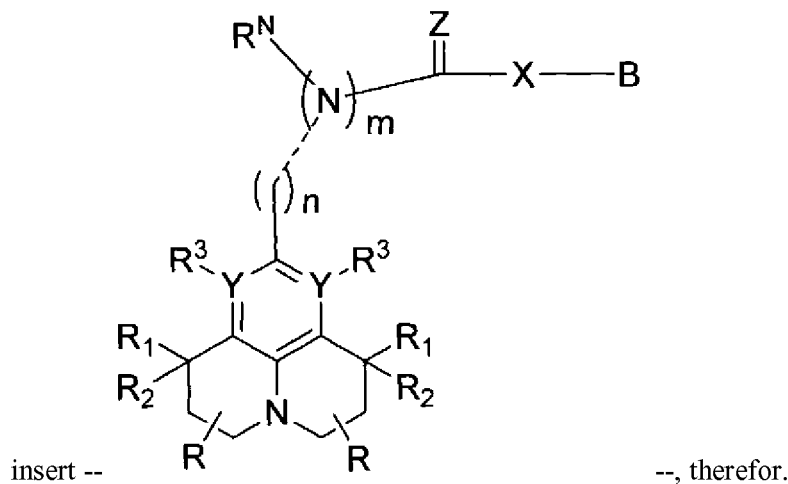 --, therefor.

In the Specification:

In column 1, line 12, after "2009," delete "to".

In column 1, line 15, after "entirety" insert -- . --.

In column 1, line 54, delete "sphingomeyeline" and insert -- sphingomyelin --, therefor.

In column 2, line 67, delete "aminocarbonxyl," and insert -- aminocarboxyl, --, therefor.

In column 4, lines 1-2, delete "aminocarbonxyl," and insert -- aminocarboxyl, --, therefor.

In column 5, line 27, delete "2d" and insert -- $2^{nd}$ --, therefor.

In column 6, line 21, delete "$R^{10}$-HI," and insert -- -$R^{10}$-HI, --, therefor.

In column 7, lines 35-40, delete " 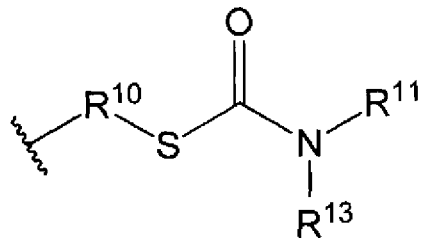 " and insert -- 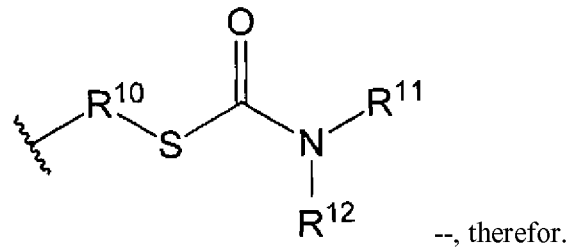 --, therefor.

In column 7, line 54, delete "coumarinone," and insert -- coumaranone, --, therefor.

In column 9, line 67, after "formula" insert -- : --.

In column 10, line 48, delete "aminocarbonxyl," and insert -- aminocarboxyl, --, therefor.

In column 10, lines 49-50, after "alkyl alkylcarbonyl," delete "formyl, oxycarbonyl, aminocarbonyl, aminocarbonxyl, alkylcarboxyl,".

CERTIFICATE OF CORRECTION (continued)
U.S. Pat. No. 8,431,702 B2

In column 10, line 67, after "formula" insert -- : --.

In column 11, line 15, after "wherein" insert -- : --.

In column 11, line 36, delete "aminocarbonxyl," and insert -- aminocarboxyl, --, therefor.

In column 11, line 54, after "by" insert -- : --.

In column 11, lines 55-65, delete " 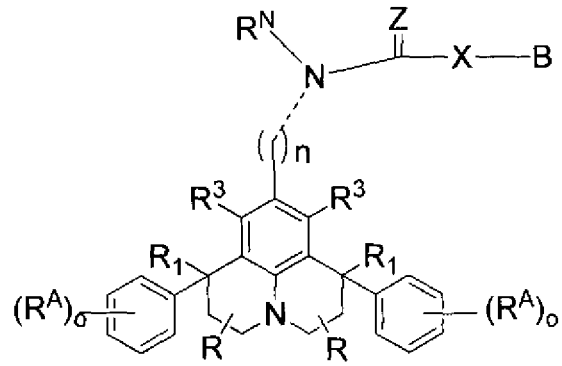 " and insert -- 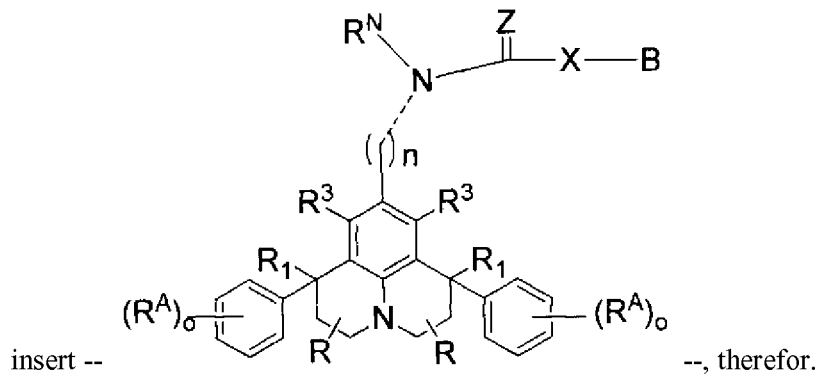 --, therefor.

In column 12, line 41, delete "—CH2F," and insert -- —CH$_2$F, --, therefor.

In column 12, line 45, delete "—C$_6$H$_{10}$Cl," and insert -- —C$_5$H$_{10}$Cl, --, therefor.

In column 12, line 47, delete "—C$_6$H$_{10}$Br," and insert -- —C$_5$H$_{10}$Br, --, therefor.

In column 12, line 49, delete "—C$_6$H$_{10}$I," and insert -- —C$_5$H$_{10}$I, --, therefor.

In column 13, lines 1-14, delete " 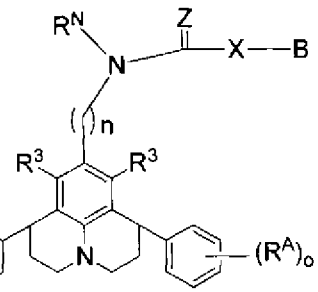 " and insert -- 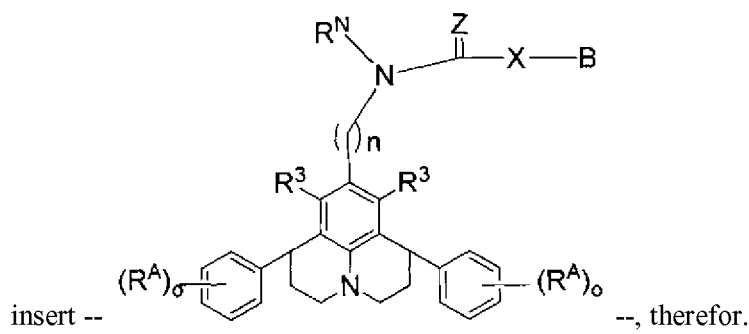 --, therefor.
In column 13, line 36, delete "coumarinone," and insert -- coumaranone, --, therefor.
In column 14, lines 1-14, after " 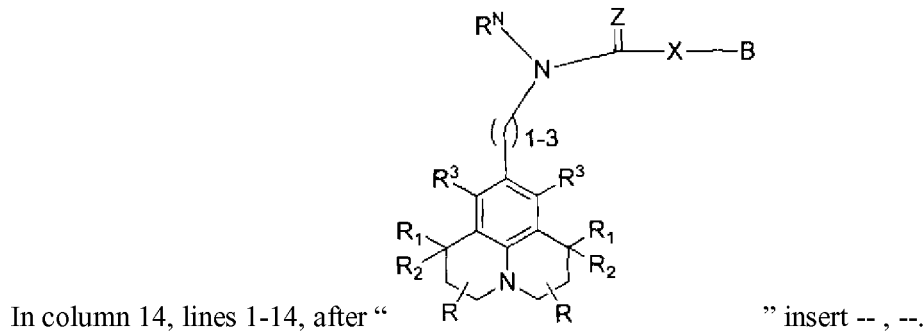 " insert -- , --.
In column 14, lines 55-65, delete " 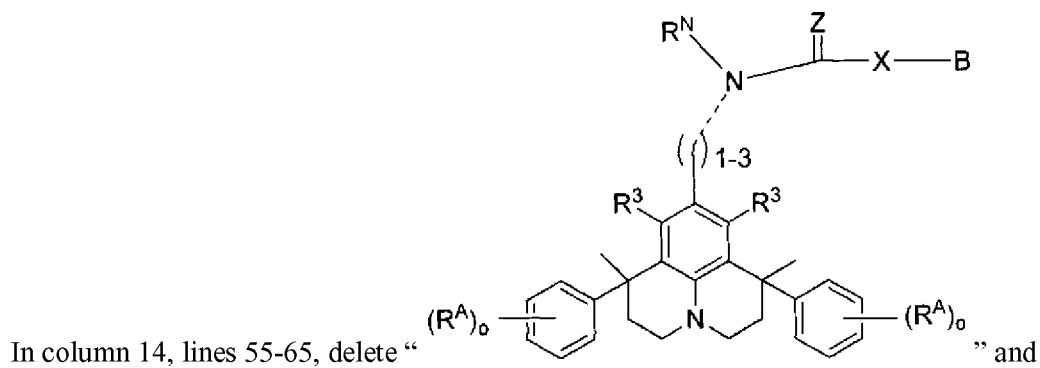 " and
insert -- 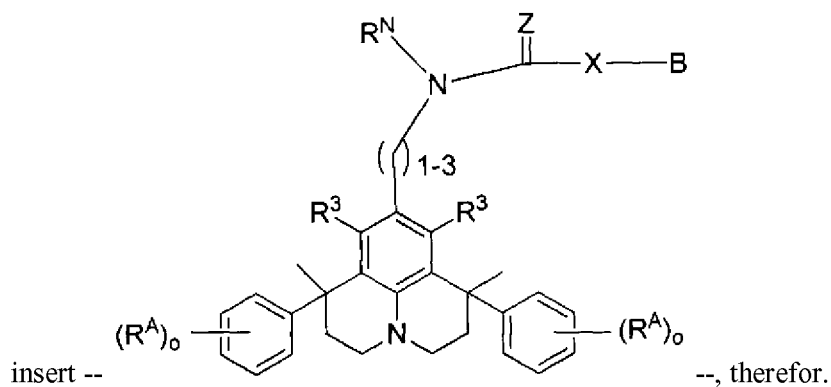 --, therefor.

In column 15, lines 1-10, delete " 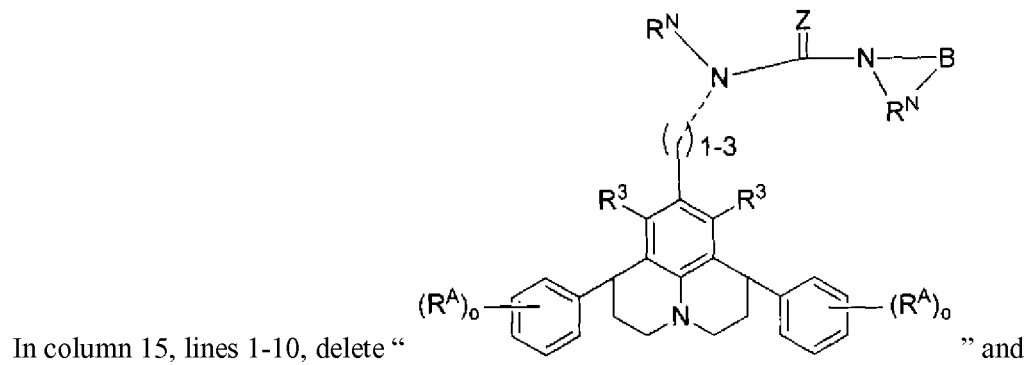 " and
insert -- 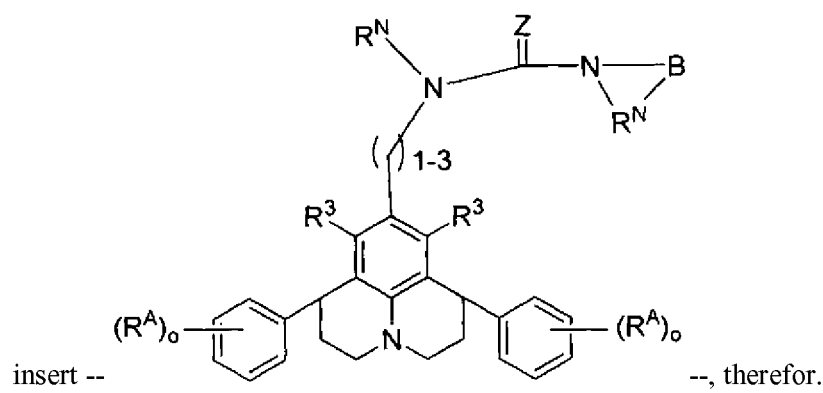 --, therefor.
In column 15, lines 15-24, delete " 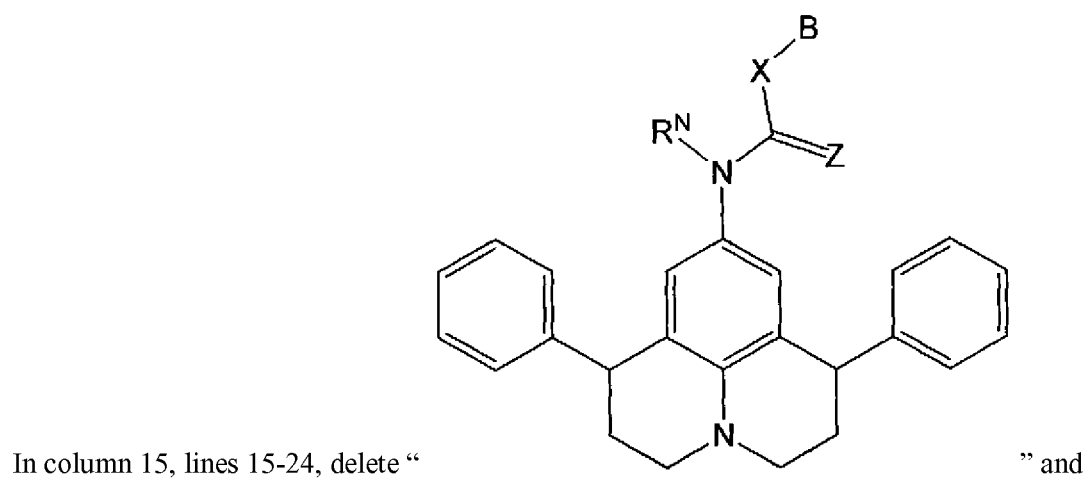 " and
insert -- 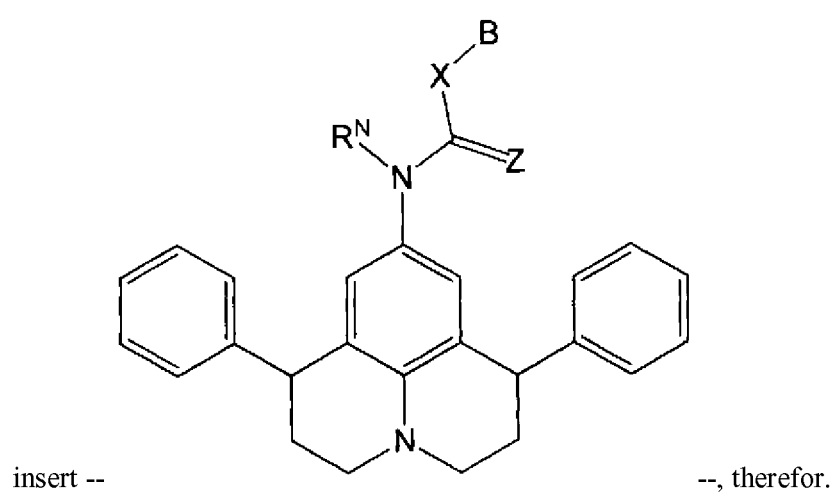 --, therefor.

In column 15, line 27, delete "wherein" and insert -- Wherein --, therefor.

In column 15, lines 42-43, delete "$N_{0-3}C_{0-5}$" and insert -- $N_{0-3}O_{0-5}$ --, therefor.

In column 15, line 63, delete "—CH2F," and insert -- —$CH_2F$, --, therefor.

In column 16, line 6, after "iodocyclohexyl" insert -- . --.

In column 18, line 2 (Including Structures), delete " 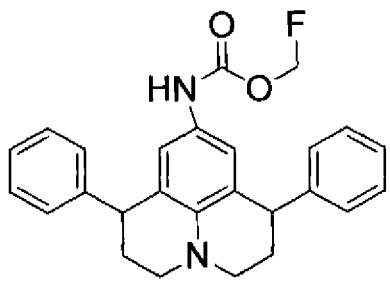 " and insert -- 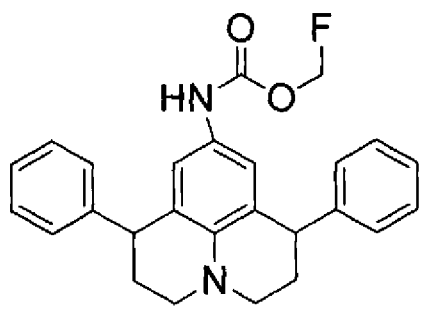 --, therefor.

In column 20, line 3 (Including Structures), delete " 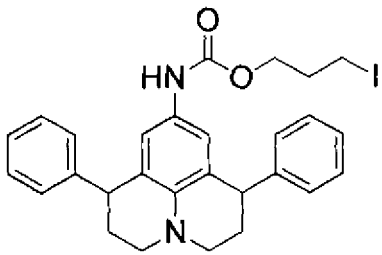 " and insert -- 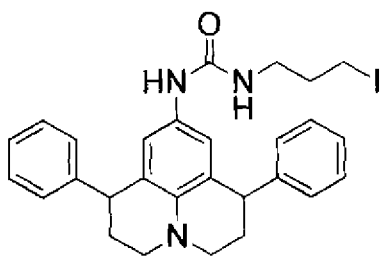 --, therefor.

In column 24, line 2 (Including Structures), delete " 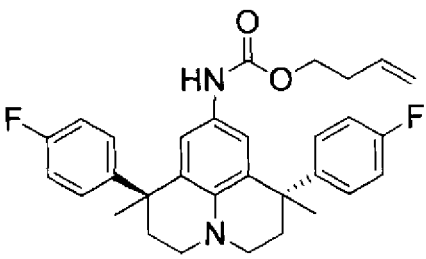 " and insert -- 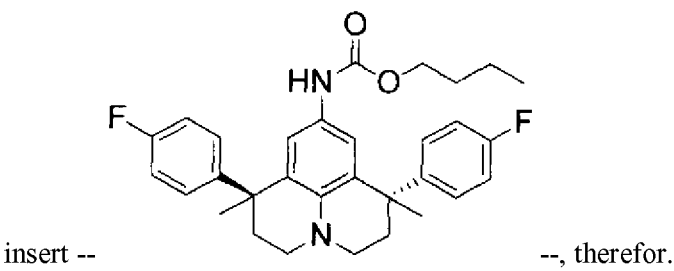 --, therefor.

In column 25, lines 46-55, delete " 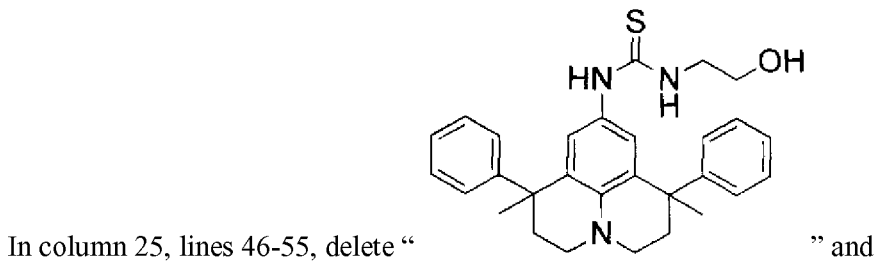 " and insert -- 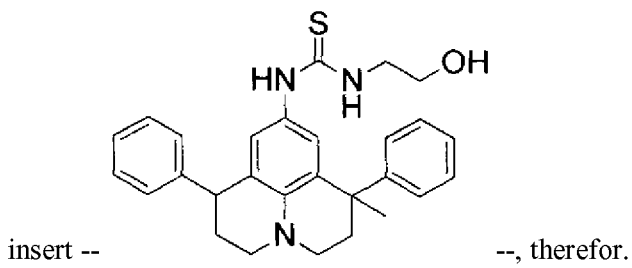 --, therefor.

In columns 35-36, line 37, delete " Seperation⟶ " and insert -- Separation⟶ --, therefor.

In column 37, line 50, delete "¹HNMR" and insert -- $^1$H NMR --, therefor.

In column 38, line 54, delete "ppm" and insert -- δ ppm --, therefor.

In column 45, line 4, delete "Hz" and insert -- Hz, --, therefor.

In column 47, line 31, delete "ppm" and insert -- δ ppm --, therefor.

In column 48, line 25, delete "ppm" and insert -- δ ppm --, therefor.

In column 49, line 7, delete " EDCl, CH$_2$Cl$_2$ DMP " and insert -- EDCl, CH$_2$Cl$_2$ DMAP --, therefor.

In column 49, line 60, delete "ppm" and insert -- δ ppm --, therefor.

In column 49, line 61, delete "ppm" and insert -- δ ppm --, therefor.

In column 52, line 5, delete "2 ylcarbamate" and insert -- 2-ylcarbamate --, therefor.

In column 53, line 4, delete "HcL" and insert -- HCl --, therefor.

In column 54, line 29, delete "Levenburg" and insert -- Levenberg --, therefor.

In column 54, line 30, delete "Table I" and insert -- Table 1 --, therefor.

CERTIFICATE OF CORRECTION (continued)
U.S. Pat. No. 8,431,702 B2

Page 8 of 8

In column 63-64, line 8, delete " 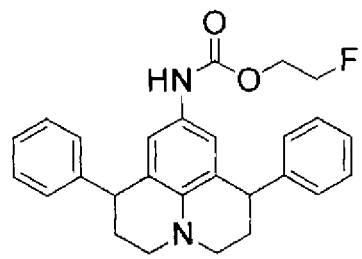 " and insert -- 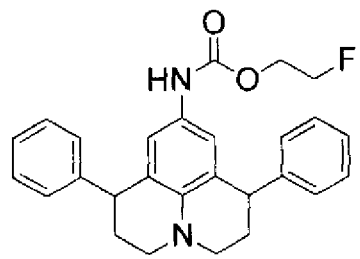 --, therefor.

In the Claims:

In column 113, lines 12-23, in claim 1, delete " 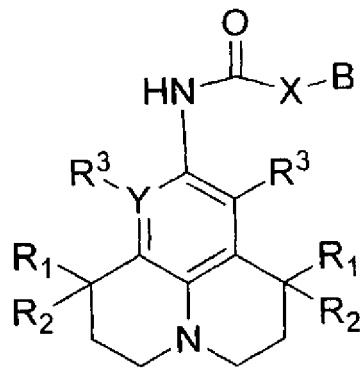 " and insert -- 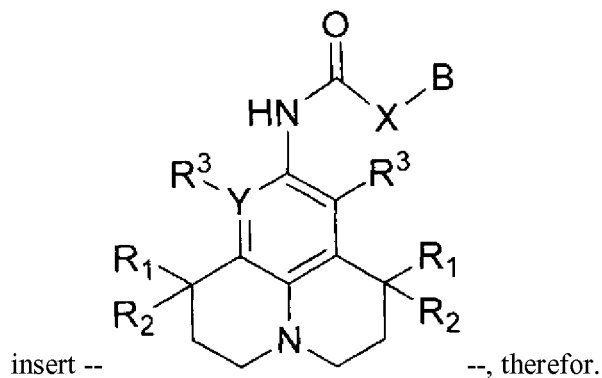 --, therefor.